United States Patent [19]

Senoo et al.

[11] Patent Number: 5,852,177
[45] Date of Patent: Dec. 22, 1998

[54] BASIC FIBROBLAST GROWTH FACTOR (BFGF) MUTEINS

[75] Inventors: Masaharu Senoo, Toyonaka; Reiko Sasada, Nagaokakyo; Tsutomu Kurokawa, Kawanishi; Koichi Igarashi, Kyoto, all of Japan

[73] Assignee: Takeda Chemical Industries, Ltd., Osaka, Japan

[21] Appl. No.: 301,460

[22] Filed: Jan. 24, 1989

Related U.S. Application Data

[63] Continuation-in-part of Ser. No. 161,123, Feb. 18, 1988, abandoned.

[30] Foreign Application Priority Data

| Feb. 24, 1987 | [JP] | Japan | 62-042218 |
|---|---|---|---|
| Feb. 25, 1987 | [JP] | Japan | 62-04344 |
| Apr. 2, 1987 | [JP] | Japan | 62-081977 |
| Jun. 12, 1987 | [JP] | Japan | 62-147511 |
| Aug. 11, 1987 | [JP] | Japan | 62-201510 |
| Nov. 17, 1987 | [JP] | Japan | 62-290283 |
| Jan. 26, 1988 | [JP] | Japan | 63-016260 |
| Aug. 19, 1988 | [JP] | Japan | 63-206968 |
| Sep. 20, 1988 | [JP] | Japan | 63-235842 |

[51] Int. Cl.$^6$ .................................................. C07K 14/50
[52] U.S. Cl. .................................... 530/399; 530/350
[58] Field of Search ........................... 530/399, 350

[56] References Cited

U.S. PATENT DOCUMENTS

| 4,956,455 | 9/1990 | Esch et al. | 530/399 |
|---|---|---|---|
| 4,959,314 | 9/1990 | Maik et al. | 435/69.7 |

FOREIGN PATENT DOCUMENTS

| 246753 | 4/1987 | European Pat. Off. |
|---|---|---|
| 237966 | 9/1987 | European Pat. Off. |
| 298723 | 1/1989 | European Pat. Off. |
| 275204 | 5/1990 | European Pat. Off. |
| 281822 | 7/1994 | European Pat. Off. |
| 288687 | 12/1994 | European Pat. Off. |
| WO-A-8607595 | 6/1986 | WIPO |
| WO-A-8701728 | 9/1986 | WIPO |
| 8703885 | 12/1986 | WIPO |

OTHER PUBLICATIONS

Senoo et al. Biochem. Biophys. Res. Commun. vol. 151, No. 2, pp. 701–708, 1988.

G. M. Fox et al. Journal of Biological Chemistry, vol. 263, No. 34, pp. 18452–18458, 1988.

Sommer, A., et al., Biochem. & Biophy. Res. Comm. 144, No. 2 1987.

Kurokawa et al. *FEBS Lett.* 213(1) pp. 189–194 (1987).

Eseh et al. *Proc. Natl. Acad Sci USA* 82:6507–6511 (1985).

Primary Examiner—Elizabeth C. Kemmerer
Attorney, Agent, or Firm—David G. Conlin; Ronald I. Eisenstein

[57] ABSTRACT

A mutein of basic fibroblast growth factors (bFGF) possesses fibroblast growth promoting activity, growth stimulating activity of capillary endothelial cells and angiogenic activity, has high stability and is low toxicity. And therefore, the present mutein is advantageously used as a healing accelerator for burns etc., a therapeutic drug for thrombosis etc., and a cell cultivation promoter.

13 Claims, 74 Drawing Sheets

Figure 1

```
MetProAlaLeuProGluAspGlySerGlyAlaPheProProGlyHisPheLysAsp         20
ATGCCAGCATTGCCCGAGGATGGCGGCAGCGGCGCCTTCCCGCCGGCCACTTCAAGGAC      60

ProLysArgLeuTyrCysLysAsnGlyGlyPheLeuArgIleHisProAspGlyArg         40
CCCAAGCGGGCTGTACTGCAAAAACGGGGGCTTCTTCCTGCGCATCCACCCCGACGGCCGA   120

ValAspGlyValArgGluLysSerAspProHisIleLysLeuGlnLeuAlaGluGlu         60
GTTGACGGGGTCCGGGAGAAGAGCGACCCTCACATCAAGCTACAACTTCAAGCAGAAGAG   180

ArgGlyValValSerIleLysGlyValCysAlaAlaAsnArgTyrLeuAlaMetLysGluAsp   80
AGAGGAGTTGTGTCTATCAAAGGAGTGTGCTAACCGTTACCTGGCTATGAAGGAAGAT     240

GlyArgLeuLeuAlaSerLysCysValThrAspGluCysPhePheGluArgLeuGlu       100
GGAAGATTACTGGCTTCTAAATGTGTTACGGATGAGTGTTTCTTTTTTGAACGATTGGAA   300

SerAsnAsnTyrAsnThrTyrArgSerArgLysTyrThrSerTrpTyrValAlaLeuLys    120
TCTAATAACTACAATACTTACCGGTCAAGGAAATACACCAGTTGGTATGTGGCACTGAAA   360

ArgThrGlyGlnTyrLysLeuGlySerLysThrGlyProGlyGlnLysAlaIleLeuPhe    140
CGAACTGGGCAGTATAAACTTGGATCCAAAACAGGACCTGGGCAGAAAGCTATACTTTTT   420

LeuProMetSerAlaLysSertrm                                         147
CTTCCAATGTCTGCTAAGAGCTGA                                         444
```

Figure 2

```
                    Ser
(1)   5'-CGTTCTTGCTGTAGAGCCGCT-3'
                   (RsaI)

Ser
(2)   5'-AACGATTAGCGCTCACTCC-3'
                 HaeII

Ser
(3)   5'-GTAACAGACTTAGAAGCTAGT-3'
                       AluI

Ser
(4)   5'-TCGAAGAAGAAAGACTCATCC-3'
                     HinfI
```

Figure 3

```
MetProAlaLeuProGluAspGlyGlySerGlyAlaPheProProGlyHisPheLysAsp      20
ATGCCAGCATTGCCCGAGGATGGGGGCAGCGGGGCCTTCCCGCCCGGCCACTTCAAGGAC     60

ProLysArgLeuTyrSerLysAsnGlyGlyPheGlyPheLeuArgIleHisProAspGlyArg  40
CCCAAGCGGCTCTACAGCAAGAACGGGGGCTTCGGCTTTCTGCGCATCCACCCCGACGGCCGA 120

ValAspGlyValArgGluLysSerAspProHisIleLysLeuGlnLeuGlnAlaGluGlu     60
GTTGACGGGGTCCGGGAGAAGAGCGACCCTCACATCAAGCTACAACTTCAAGCAGAAGAG    180

ArgGlyValValSerIleLysGlyValCysAlaAsnArgTyrLeuAlaMetLysGluAsp     80
AGAGGAGTTGTCTCTATCAAAGGAGTGTGTGCTAACCGTTACCTGGCTATGAAGGAAGAT    240

GlyArgLeuLeuAlaSerLysCysValThrAspGluCysPhePheGluArgLeuGlu       100
GGAAGATTACTGGCTTCTAAATGTGTTACGGATGAGTGTTTCTTTTTTGAACGATTGGAA    300

SerAsnAsnTyrAsnThrThrTyrLysSerArgLysTyrThrSerTrpTyrValAlaLeuLys 120
TCTAATAACTACAATACAACTTACAAGAGCAGAAAATACACCAGTTGGTATGTGGCACTGAAA 360

ArgThrGlyGlnTyrLysLeuGlySerThrGlyProGlyGlnLysAlaIleLeuPhe       140
CGAACTGGGCAGTATAAACTTGGATCCACAGGACCTGGGCAGAAAGCTATACTTTTT       420

LeuProMetSerAlaLysSertrm                                        147
CTTCCAATGTCTGCTAAGAGCTGA                                        444
```

Figure 4

```
MetProAlaLeuProGluAspGlyGlySerGlyAlaPheProProGlyHisPheLysAsp        2
ATGCCAGCATTGCCCGAGGATGGTGGCAGCGGGGCCTTCCCGCCACTTCAAGGAC           60

ProLysArgLeuTyrCysLysAsnGlyGlyPhePheLeuArgIleHisProAspGlyArg        4
CCCAAGCGGCTGTACTGCAAAAACGGGGGCTTCTTCCTGCGCATCCACCCCGACGGCCGA      12 0

ValAspGlyValArgGluLysSerAspProHisIleLysLeuGlnLeuGlnLeuGlnLeuGluGlu   6
GTTGACGGGGTCCGGGAGAAGAGCGACCCTCACATCAAGCTACAACTTCAAGCAGAAGAG     180

ArgGlyValValSerIleLysGlyValSer AlaAsnArgTyrLeuAlaMetLysGluAsp        8
AGAGGAGTTGTGTCTATCAAAGGAGTGAGC GCTAATCGTTACCTGGCTATGAAGGAAGAT    240

GlyArgLeuLeuAlaSerLysCysValThrAspGluCysPhePheGluArgLeuGlu          10
GGAAGATTACTGGCTTCTAAATGTGTTACGGATGAGTGTTTCTTTTTTGAACGATTGGAA    300

SerAsnAsnTyrAsnThrTyrArgSerArgLysTyrThrSerTrpTyrValAlaLeuLys        12
TCTAATAACTACAATACTTACCGGTCAAGGAAATACACCAGTTGGTATGTGGCACTGAAA   360

ArgThrGlyGlnTyrLysLeuLeuGlySerLysThrGlyProGlyGlnLysAlaIleLeuPhe     14
CGAACTGGGCAGTATAAACTTGGATCCAAAAACAGGACCTGGGCAGAAAGCTATACTTTTT   42 0

LeuProMetSerAlaLysSertrm                                            14
CTTCCAATGTCTGCTAAGAGCTGA                                          44 4
```

Figure 5

```
           MetProAlaLeuProGluAspGlyGlySerGlyAlaPheProProGlyHisPheLysAsp     20
           ATGCCAGCATTGCCCGAGGATGGCGGCAGCGGGGCCTTCCCGCCACTTCAAGGAC              60

ProLysArgLeuTyrCysLysAsnGlyGlyPheLeuArgIleHisProAspGlyArg            40
           CCCAAGCGGCTGTACTGCAAAAACGGGGGCTTCCTTCGCATCCACCCCGACGGCCGA          120

ValAspGlyValArgGluLysSerAspProHisIleLysLeuGlnLeuGlnAlaGluGlu         60
           GTTGACGGGGTCCGGGAGAAGAGCGACCCTCACATCAAGCTACAACTCAAGCAGAAGAG        180

ArgGlyValValSerIleLysGlyValCysAlaAsnArgTyrLeuAlaMetLysGluAsp         80
           AGAGGAGTTGTGTCTATCAAAGGAGTGTGCTAACCGTTACCTGGCTATGAAGGAAGAT        240

GlyArgLeuLeuAlaSerLysSerValThrAspGluCysPhePheGluArgLeuGlu           100
           GGAAGATTACTAGCTTCTAAGTCTGTTACGGATGAGTGTTTCTTTTTGAACGATTGGAA       300

SerAsnAsnTyrAsnThrTyrArgSerArgLysTyrThrSerTrpTyrValAlaLeuLys       120
           TCTAATAACTACAATACTTACCGGTCAAGGAAATACACCAGTTGGTATGTGGCACTGAAA      360

ArgThrGlyGlnTyrLysLeuGlySerLysThrGlyProGlyGlnLysAlaIleLeuPhe       140
           CGAACTGGGCAGTATAAACTTGGATCCAAAACAGGACCTGGGCAGAAAGCTATACTTTTT      420

LeuProMetSerAlaLysSertrm                                           147
           CTTCCAATGTCTGCTAAGAGCTGA                                           444
```

Figure 6

```
MetProAlaLeuProGluAspGlyGlySerGlyAlaPheProProGlyHisPheLysAsp    20
ATGCCAGCATTGCCCGAGGATGGCGGCAGCGGGGCGGCCTTCCCGCCCGGCCACTTCAAGGAC  60

ProLysArgLeuTyrCysLysAsnGlyGlyPhePheLeuArgIleHisProAspGlyArg    40
CCCAAGCGGCTGTACTGCAAAAACGGGGGCTTCTTCCTGCGCATCCACCCCGACGGCCGA   120

ValAspGlyValArgGluLysSerAspProHisIleLysLeuGlnLeuGlnAlaGluGlu    60
GTTGACGGGGTCCGGGAGAAGAGCGACCCTCACATCAAGCTACAACTTCAAGCAGAAGAG   180

ArgGlyValValSerIleLysGlyValCysAlaAsnArgTyrLeuAlaMetLysGluAsp    80
AGAGGAGTTGTGTCTATCAAAGGAGTGTGTGCTAACCGGTTACCTGGCTATGAAGGAAGAT  240

GlyArgLeuLeuAlaSerLysCysValThrAspGlu|SerPhePhePheGluArgLeuGlu  100
GGAAGATTACTGGCTTCTAAATGTGTTACGGATGAG|TCT|TTCTTCTTCGAACGATTGGAA 300

SerAsnAsnTyrAsnThrTyrArgSerArgLysTyrThrSerTrpTyrValAlaLeuLys   120
TCTAATAACTACAATACTTACCGGTCAAGGAAATACACCAGTTGGTATGTGGCACTGAAA   360

ArgThrGlyGlnTyrLysLeuGlySerLysThrGlyProGlyGlnLysAlaIleLeuPhe   140
CGAACTGGGCAGTATAAACTTGGATCCAAAACAGGACCTGGGCAGAAAGCTATACTTTTT   420

LeuProMetSerAlaLysSertrm                                       147
CTTCCAATGTCTGCTAAGAGCTGA                                       444
```

Figure 11

```
MetProAlaLeuProGluAspGlySerGlyAlaPheProProGlyHisPheLysAsp      20
ATGCCAGCATTGCCGAGGATGGCGGCAGCGGCGGCCTTCCCGCCCGGCCACTTCAAGGAC   60

ProLysArgLeuTyrCysLysAsnGlyGlyPheLeuArgIleHisProAspGlyArg      40
CCCAAGCGGCTGTACTGCAAAAACGGGGGCTTCTTCCTGCGCATCCACCCCGACGGCCGA  120

ValAspGlyValArgGluLysSerAspProHisIleLysLeuGlnLeuAlaGluGlu      60
GTTGACGGGGTCCGGGAGAAGAGCGACCCTCACATCAAGCTACAACTTCAAGCAGAAGAG  180

ArgGlyValValSerIleLysGlyValSer AlaAsnArgTyrLeuAlaMetLysGluAsp  80
AGAGGAGTTGTGTCTATCAAAGGAGTGAGC TAATCGTTACCTGGCTATGAAGGAAGAT   240

GlyArgLeuLeuAlaSerLys Ser ValThrAspGluCysPhePheGluArgLeuGlu   100
GGAAGATTACTAGCTTCTAAG TCT GTTACGGATGAGTGTTTCTTTTTGAACGATTGGAA  300

SerAsnAsnTyrAsnThrTyrArgSerArgLysTyrThrSerTrpTyrValAlaLeuLys  120
TCTAATAACTACAATACTTACCGGTCAAGGAAATACACCAGTTGGTATGTGGCACTGAAA  360

ArgThrGlyGlnTyrLysLeuGlySerLysThrGlyProGlyGlnLysAlaIleLeuPhe  140
CGAACTGGGCAGTATAAACTTGGATCCAAAACAGGACCTGGGCAGAAAGCTATACTTTTT  420

LeuProMetSerAlaLysSertrm                                      147
CTTCCAATGTCTGCTAAGAGCTGA                                      444
```

Figure 13

```
MetProAlaLeuProGluAspGlyGlySerGlyAlaPheProProGlyHisPheLysAsp              20
ATGCCAGCATTGCCCGAGGATGGGGGCAGCGGCGCCTTCCCGCCGGCCACTTCAAGGAC              60

ProLysArgLeuTyr Ser LysAsnGlyGlyPhePheLeuArgIleHisProAspGlyArg            40
CCCAAGCGGCTCTAC AGC AAGAACGGGGGCTTCTTCCTGCGCATCCACCCCGACGGCCGA           120

ValAspGlyValArgGluLysSerAspProHisIleLysLeuGlnAlaGluGlu                    60
GTTGACGGGGTCCGGGAGAAGAGCGACCCTCACATCAAGCTACAACTTCAAGCAGAAGAG            180

ArgGlyValValSerIleLysGlyValSer Ala AlaAsnArgTyrLeuAlaMetLysGluAsp         80
AGAGGAGTTGTGTCTATCAAAGGAGTG AGC GCTAATCGTTACCTGGCTATGAAGGAAGAT           240

GlyArgLeuLeuAlaSerLys Ser ValThrAspGluCysPhePheGluArgLeuGlu              100
GGAAGATTACTAGCTTCTAAG TCT GTTACGGATGAGTGTTTCTTTTTGAACGATTGGAA            300

SerAsnAsnTyrAsnThrTyrArgSerArgLysTyrThrSerTrpTyrValAlaLeuLys             120
TCTAATAACTACAATACTTACCGGTCAAGGAAATACACCAGTTGGTATGTGGCACTGAAA            360

ArgThrGlyGlnTyrLysLeuLeuGlySerLysThrGlyProGlyGlnLysAlaIleLeuPhe          140
CGAACTGGGCAGTATAAACTTGGATCCAAAACAGGACCTGGGCAGAAAGCTATACTTTTT            420

LeuProMetSerAlaLysSertrm                                                 147
CTTCCAATGTCTGCTAAGAGCTGA                                                 444
```

Figure 15

```
MetProAlaLeuProGluAspGlyGlySerGlyAlaPheProProGlyHisPheLysAsp                    20
ATGCCAGCATTGCCCGAGGATGGGGGCAGCGGGGCCTTCCCGCCGGGCCACTTCAAGGAC                    60

ProLysArgLeuTyr|Ser|LysAsnGlyGlyPhePheLeuArgIleHisProAspGlyArg                  40
CCCAAGCGGCTCTAC|AGC|AAGAACGGGGGCTTCTTCCTGCGCATCCACCCCGACGGCCGA                 120

ValAspGlyValArgGluLysSerAspProHisIleLysLeuGlnLeuGlnAlaGluGlu                    60
GTTGACGGGGTCCGGGAGAAGAGCGACCCTCACATCAAGCTACAACTTCAAGCAGAAGAG                   180

ArgGlyValValSerIleLysGlyVal|Ser|AlaAsnArgTyrLeuAlaMetLysGluAsp                  80
AGAGGAGTTGTGTCTATCAAAGGAGTG|AGC|GCTAATCGTTACCTGGCTATGAAGGAAGAT                 240

GlyArgLeuLeuAlaSerLysSer|Ser|PhePheGluArgLeuGlu                                100
GGAAGATTACTAGCTTCTAAG|ICI|GTCTTCTTCGAACGATTGGAA                                300

SerAsnAsnTyrAsnThrTyrArgSerArgLysTyrThrSerTrpTyrValAlaLeuLys                   120
TCTAATAACTACAATACTTACCGGTCAAGGAAATACACCAGTTGGTATGTGGCACTGAAA                  360

ArgThrGlyGlnTyrLysLeuLeuGlySerLysThrGlyProGlyGlnLysAlaIleLeuPhe               140
CGAACTGGGCAGTATAAACTTGGATCCAAAACAGGACCTGGGCAGAAAGCTATACTTTTT                  420

LeuProMetSerAlaLysSertrm                                                      147
CTTCCAATGTCTGCTAAGAGCTGA                                                     444
```

Figure 17

```
MetProAlaLeuProGluAspGlyGlySerGlyAlaPheProProGlyHisPheLysAsp        20
ATGCCAGCATTGCCCGAGGATGGCGGCAGCGGGGCCTTCCCGCCGGCCACTTCAAGGAC         60

ProLysArgLeuTyr|Ser|LysAsnGlyGlyPhePheLeuArgIleHisProAspGlyArg      40
CCCAAGCGGCTCTAC AGC AAGAACGGGGGCTTCTTCCTGCGCATCCACCCCGACGGCCGA     120

ValAspGlyValArgGluLysSerAspProHisIleLysLeuGlnLeuGlnAlaGluGlu        60
GTTGACGGGGTCCGGGAGAAGAGCGACCCTCACATCAAGCTACAACTTCAAGCAGAAGAG      180

ArgGlyValValSerIleLysGlyVal|SerAlaAsnArgTyrLeuAlaMetLysGluAsp       80
AGAGGAGTTGTCTATCAAAGGAGTG AGC GCTAATCGTTACCTGGCTATGAAGGAAGAT      240

GlyArgLeuLeuAlaSerLysCysValThrAspGluCysPhePheGluArgLeuGlu          100
GGAAGATTACTGGCTTCTAAATGTGTTACGGATGAGTGTTTCTTTTTTGAACGATTGGAA      300

SerAsnAsnTyrAsnThrTyrArgSerArgLysTyrThrSerTrpTyrValAlaLeuLys       120
TCTAATAACTACAATACTTACCGGTCAAGGAAATACACCAGTTGGTATGTGGCACTGAAA      360

ArgThrGlyGlnTyrLysLeuGlySerLysThrGlyProGlyGlnLysAlaIleLeuPhe       140
CGAACTGGGCAGTATAAACTTGGATCCAAAACAGGACCTGGGCAGAAAGCTATACTTTTT      420

LeuProMetSerAlaLysSertrm                                           147
CTTCCAATGTCTGCTAAGAGCTGA                                           444
```

Figure 19

```
MetProAlaLeuProGluAspGlyGlySerGlyAlaPheProProGlyHisPheLysAsp      20
ATGCCAGCATTGCCCGAGGATGGGGGCAGCGGGGCCTTCCCGCCCACTTCAAGGAC          60

ProLysArgLeuTyrCysLysAsnGlyGlyPhePheLeuArgIleHisProAspGlyArg      40
CCCAAGCGGCTGTACTGCAAAAACGGGGGCTTCTTCCTGCGCATCCACCCCGACGGCCGA     120

ValAspGlyValArgGluLysSerAspProHisIleLysLeuGlnLeuGlnAlaGluGlu      60
GTTGACGGGGTCCGGGAGAAGAGCGACCCTCACATCAAGCTACAACTTCAAGCAGAAGAG    180

ArgGlyValValSerIleLysGlyVal SerAlaAsnArgTyrLeuAlaMetLysGluAsp     80
AGAGGAGTTGTCTCTATCAAAGGAGTG AGG GCTAATCGTTACCTGGCTATGAAGGAAGAT   240

GlyArgLeuAlaSerLysCysValThrAspGlu Ser PhePhePheGluArgLeuGlu      100
GGAAGATTACTGGCTTCTAAATGTGTTACGGATGAG TCT TCTTCTTCGAACGATTGGAA   300

SerAsnAsnTyrAsnThrTyrArgSerArgLysTyrThrSerTrpTyrValAlaLeuLys     120
TCTAATAACTACAATACTTACCGGTCAAGGAAATACACCAGTTGGTATGTGGCACTGAAA   360

ArgThrGlyGlnTyrLysLeuLeuGlyProGlyGlnLysAlaIleLeuPhe              140
CGAACTGGGCAGTATAAACTTGGATCCAAAACAGGACCTGGGCAGAAAAGCTATACTTTTT  420

LeuProMetSerAlaLysSertrm                                         147
CTTCCAATGTCTGCTAAGAGCTGA                                        444
```

Figure 21

```
MetProAlaLeuProGluAspGlyGlySerGlyAlaPheProProGlyHisPheLysAsp         20
ATGCCAGCATTGCCCGAGGATGGCGGCAGCGGGGCCTTCCCGCCGGGCCACTTCAAGGAC         60

ProLysArgLeuTyr|Ser|LysAsnGlyGlyPheGlyPheLeuArgIleHisProAspGlyArg     40
CCCAAGCGGCTCTAC|AGC|AAGAACGGGGGCTTCGGCTTCCTGCGCATCCACCCCGACGGCCGA    120

ValAspGlyValValArgGluLysSerAspProHisIleLysLeuGlnLeuAlaGluGlu         60
GTTGACGGGGTCCGGGAGAAGAGCGACCCTCACATCAAGCTACAACTTGCAGAAGAG            180

ArgGlyValValSerIleLysGlyValCysAlaAsnArgTyrLeuAlaMetLysGluAsp         80
AGAGGAGTTGTGTCTATCAAAGGAGTGTGTGCTAACCGGTTACCTGGCTATGAAGGAAGAT        240

GlyArgLeuLeuAlaSerLys|Ser|ValThrAspGluCysPhePheGluArgLeuGlu         100
GGAAGATTACTAGCTTCTAAG|TCT|GTTACGGATGAGTGTTTCTTTTTTGAACGATTGGAA       300

SerAsnAsnTyrAsnThrTyrArgLysTyrThrSerTrpTyrValAlaLeuLys              120
TCTAATAACTACAATACATACCGGTCAAGGAAATACACCAGTTGGTATGTGGCACTGAAA        360

ArgThrGlyGlnTyrLysLeuGlySerLysThrGlyProGlyGlnLysAlaIleLeuPhe        140
CGAACTGGGCAGTATAAACTTGGATCCAAAAACAGGACCTGGGCAGAAAGCTATACTTTT        420

LeuProMetSerAlaLysSertrm                                            147
CTTCCAATGTCTGCTAAGAGCTGA                                            444
```

Figure 23

```
  MetProAlaLeuProGluAspGlyGlySerGlyAlaPheProProGlyHisPheLysAsp      20
  ATGCCAGCATTGCCCGAGGATGGCGGCAGCGGGGCCTTCCCGCCCGGCCACTTCAAGGAC      60

ProLysArgLeuTyrSerLysAsnGlyGlyPhePheLeuArgIleHisProAspGlyArg      40
  CCCAAGCGGCTCTACAGCAAGAACGGGGGCTTCTTCCTGCGCATCCACCCCGACGGCCGA     120

ValAspGlyValArgGluLysLeuSerAspProHisIleLysLeuGlnLeuGlnAlaGluGlu    60
  GTTGACGGGGTCCGGGAGAAGAGCGACCCTCACATCAAGCTACAACTTCAAGCAGAAGAG     180

ArgGlyValValSerIleLysGlyValCysAlaAsnArgTyrLeuAlaMetLysGluAsp      80
  AGAGGAGTTGTGTCTATCAAAGGAGTGTGTGCTAACCGTTACCTGGCTATGAAGGAAGAT     240

GlyArgLeuLeuAlaSerLysCysValThrAspGluSerPhePhePheGluArgLeuGlu     100
  GGAAGATTACTGGCTTCTAAATGTGTTACGGATGAGTCTTTCTTCTTCGAACGATTGGAA     300

SerAsnAsnTyrAsnThrTyrArgSerArgLysTyrThrSerTrpTyrValAlaLeuLys     120
  TCTAATAACTACAATACTTACCGGTCAAGGAAATACACCAGTTGGTATGTGGCACTGAAA     360

ArgThrGlyGlnTyrLysLeuLeuGlySerLysThrGlyProGlyGlnLysAlaIleLeuPhe   140
  CGAACTGGGCAGTATAAACTTGGATCCAAAACAGGACCTGGGCAGAAAAGCTATACTTTTT   420

LeuProMetSerAlaLysSerᵣₘ                                         147
  CTTCCAATGTCTGCTAAGAGCTGA                                        444
```

Figure 25

```
              MetProAlaLeuProGluAspGlyGlySerGlyAlaPheProProGlyHisPheLysAsp    20
              ATGCCAGCATTGCCCGAGGATGGGGGCAGCGGGCCCTTCCCGCCCACTTCAAGGAC            60

ProLysArgLeuTyrCysLysAsnGlyGlyPhePheLeuArgIleHisProAspGlyArg       40
              CCCAAGCGGCTGTACTGCAAAAACGGGGGCTTCTTCCTGCATCCAGACGGCCGA              120

ValAspGlyValArgGluLysSerAspProHisIleLysLeuGlnLeuAlaGluGlu          60
              GTTGACGGGGTCCGGGAGAAGAGCGACCCTCACATCAAGCTACAACTTGCAGAAGAG          180

ArgGlyValValSerIleLysGlyValCysAlaAsnArgTyrLeuAlaMetLysGluAsp       80
              AGAGGAGTTGTCTATCAAAGGAGTGTGCTAACCGTTACCTGGCTATGAAGGAAGAT          240

GlyArgLeuLeuAlaSerLys[Ser]ValThrAspGlu[Ser]PhePheGluArgLeuGlu     100
              GGAAGATTACTAGCTTCTAAG TCT GTTACGGATGAGT TCT TTCTTCTTCGAACGATTGGAA    300

SerAsnAsnTyrAsnThrTyrArgSerArgLysTyrThrSerTrpTyrValAlaLeuLys     120
              TCTAATAACTACAATACTTACCGGTCAAGGAAATACACCAGTTGGTATGTGGCACTGAAA      360

ArgThrGlyGlnTyrLysLeuGlySerLysThrGlyProGlyLeuGlnLysAlaIleLeuPhe   140
              CGAACTGGGCAGTATAAACTTGGATCCAAAACAGGACCTGGGCAGAAAGCTATACTTTT        420

LeuProMetSerAlaLysSertrm                                          147
              CTTCCAATGTCTGCTAAGAGCTGA                                           444
```

Figure 27

```
MetProAlaLeuProGluAspGlySerGlyAlaPheProProGlyHisPheLysAsp                      20
ATGCCAGCATTGCCCGAGGATGGGAGCGGGGCAGCCTTCCCGCCCGGCCACTTCAAGGAC                   60

ProLysArgLeuTyrCysLysAsnGlyGlyPhePheLeuArgIleHisProAspGlyArg                   40
CCCAAGCGGCTGTACTGCAAAAACGGGGGCTTCTTCCTGCGCATCCACCCCGACGGCCGA                  120

ValAspGlyValArgGluLysSerAspProHisIleLysLeuGlnLeuGlnAlaGluGlu                   60
GTTGACGGGGTCCGGGAGAAGAGCGACCCTCACATCAAGCTACAACTTCAAGCAGAAGAG                  180

ArgGlyValValSerIleLysGlyValSerAlaAsnArgTyrLeuAlaMetLysGluAsp                   80
AGAGGAGTTGTGTCTATCAAGGAGGTGAGCGCTAATCGTTACCTGGCTATGAAGGAAGAT                  240

GlyArgLeuLeuAlaSerLysSerValThrAspGluPhePheGluArgLeuGluGlu                     100
GGAAGATTACTAGCTTCTAAGTCTGTTACGGATGAGTCTTTCTTCGAACGATTGGAA                     300

SerAsnAsnTyrAsnThrTyrArgSerArgLysTyrThrSerTrpTyrValAlaLeuLys                  120
TCTAATAACTACAATACTTACCGGTCAAGGAAATACACCAGTTGGTATGTGGCACTGAAA                  360

ArgThrGlnTyrLysLeuGlyProGlyGlnLysAlaIleLeuPhe                                 140
CGAACTCAGTACAAACTTGGATCCAAAACAGGACCTGGGCAGAAAGCTATACTTTTT                     420

LeuProMetSerAlaLysSertrm                                                      147
CTTCCAATGTCTGCTAAGAGCTGA                                                      444
```

Figure 29

```
MetProAlaLeuProGluProGlyAspGlySerGlyAlaPheProProGlyHisPheLysAsp       20
ATGCCAGCATTGCCCGAGCCAGGAGATGGCGGCAGCGGCGCCTTCCCGCCCGGCCACTTCAAGGAC    60

ProLysArgLeuTyr Ser LysAsnGlyGlyPheLeuArgIleHisProAspGlyArg           40
CCCAAGCGGCTCTAC AGC AAGAACGGGGGCTTCCTTCGCATCCACCCCGACGGCCGA           120

ValAspGlyValArgGluLysSerAspProHisIleLysLeuLeuGlnAlaGluGlu             60
GTTGACGGGGTCCGGGAGAAGAGCGACCCTCACATCAAGCTACAACTTCAAGCAGAAGAG         180

ArgGlyValValSerIleLysLysGlyVal Ser AlaAsnArgTyrLeuAlaMetLysGluAsp     80
AGAGGAGTTGTGTCTATCAAAGGAGTG AGC GCTAATCGTTACCTGGCTATGAAGGAAGAT        240

GlyArgLeuLeuAlaSerLysCysValThrAspGluSer PhePheGluArgLeuGlu           100
GGAAGATTACTGGCTTCTAAATGTGTTACGGATGAG TCT TTCTTCGAACGATTGGAA          300

SerAsnAsnTyrAsnThrThrTyrArgSerArgLysTyrThrSerTrpTyrValAlaAlaLeuLys   120
TCTAATAACTACAATACTACATACCGGTCAAGGAAATACACCAGTTGGTATGTGGCACTGAAA      360

ArgThrGlyGlnTyrLysLeuGlySerLysThrGlyProGlyGlnLysAlaIleLeuPhe         140
CGAACTGGGCAGTATAAACTTGGATCCAAAACAGGACCTGGGCAGAAAGCTATACTTTTT         420

LeuProMetSerAlaLysSertrm                                             147
CTTCCAATGTCTGCTAAGAGCTGA                                             444
```

Figure 31

```
MetProAlaLeuProGluProAspGlySerGlyAlaPheProProGlyHisPheLysAsp         20
ATGCCAGCATTGCCCGAGCCAGAGGATGGGTCAGGGGCAGCCTTCCCGCCCGGCCACTTCAAGGAC    60

ProLysArgLeuTyr[Ser]LysAsnGlyGlyPhePheLeuArgIleHisProAspGlyArg        40
CCCAAGCGGCTCTAC AGC AAGAACGGGGGCTTCTTCCTTCGGCATCCACCCCGACGGCCGA       120

ValAspGlyValArgGluLysSerAspProHisIleLysLeuGlnLeuGlnAlaGluGlu          60
GTTGACGGGGTCCGGGAGAAGAGCGACCCTCACATCAAGCTACAACTTCAAGCAGAAGAG         180

ArgGlyValValSerIleLysGlyValCysAlaAsnArgTyrLeuAlaMetLysGluAsp          80
AGAGGAGTTGTGTCTATCAAAGGAGTGTGTGCTAACCGTTACCTGGCTATGAAGGAAGAT        240

GlyArgLeuLeuAlaSerLys[Ser]ValThrAspGlu[Ser]PhePheGluArgLeuGlu        100
GGAAGATTACTAGCTTCTAAG TCT GTTACGGATGAG TCT TTCTTCTTCGAACGATTGGAA     300

SerAsnAsnTyrAsnThrTyrArgSerArgLysTyrThrSerTrpTyrValAlaLeuLys         120
TCTAATAACTACAATACTTACCGGTCAAGGAAATACACCAGTTGGTATGTGGCACTGAAA        360

ArgThrGlyGlnTyrLysLeuLeuGlySerLysThrGlyProGlyGlnLysAlaIleLeuPhe      140
CGAACTGGGCAGTATAAACTTGGATCCAAAACAGGACCTGGGCAGAAAGCTATACTTTTT        420

LeuProMetSerAlaLysSertrm                                             147
CTTCCAATGTCTGCTAAGAGCTGA                                             444
```

Figure 38

```
              Met Thr
(1)  5'-CGCCATGGTGCCATCCTC-3'
           NcoI

MeT
(2)  5'-CGGGCATGAATTCGCCGCT-3'
                EcoRI trm
(3)  5'-TAACACCTTAAGAAGCCAG-3'
              AflII Asn
(4)  5'-CCGGACTCCGTTAACTCGG-3'
               HpaI Gln
(5)  5'-CTTCTCCTGGACTCCGTCAAC-3'
             (HpaII)

Arg
(6)  5'-CGGACTCCTCTAACTCGGC-3'
              (HpaI)

Leu Ser
(7)  5'-TCTTCTCCAGGGATCCGTT-3'
                   BamHI
```

Figure 39

```
            MetProAlaLeuProGluAspGlyThrMet GlyAlaPheProProGlyHisPheLysAsp      20
            ATGCCAGCATTGCCCGAGGATGGCACCATG GGGGCCTTCCCGCCGGGCCACTTCAAGGAC      60

ProLysArgLeuTyrCysLysLysAsnGlyGlyPheLeuArgIleHisProAspGlyArg         40
            CCCAAGCGGCTGTACTGCAAAAACGGGGGCTTCTTCCTGCGCATCCACCCCGACGGCCGA       120

ValAspGlyValArgGluLysSerAspProHisIleLysLeuGlnLeuGlnAlaGluGlu        60
            GTTGACGGGGTCCGGGAGAAGAGCGACCCTCACATCAAGCTACAACTTCAAGCAGAAGAG       180

ArgGlyValValSerIleLysGlyValCysAlaAsnArgTyrLeuAlaMetLysGluAsp        80
            AGAGGAGTTGTGTCTATCAAAGGAGTGTGCTAACCGTTACCTGGCTATGAAGGAAGAT         240

GlyArgLeuLeuAlaSerLysCysValThrAspGluCysPhePheGluArgLeuGlu          100
            GGAAGATTACTGGCTTCTAAATGTGTTACGGATGAGTGTTTCTTTTTGAACGATTGGAA       300

SerAsnAsnTyrAsnThrTyrArgSerArgLysTyrThrSerTrpTyrValAlaLeuLys       120
            TCTAATAACTACAATACTTACCGGTCAAGGAAATACACCAGTTGGTATGTGGCACTGAAA      360

ArgThrGlyGlnTyrLysLeuGlyProGlySerLysThrGlyGlnLysAlaIleLeuPhe       140
            CGAACTGGGCAGTATAAACTTGGGATCCAAAACAGGACCTGGGCAGAAAGCTATACTTTT      420

LeuProMetSerAlaLysSertrm                                           147
            CTTCCAATGTCTGCTAAGAGCTGA                                           444
```

Figure 40

```
                                                      MetProGlyHisPheLysAsp       7
                                 GAATTCACTTCAAGGAC   27
                                      ATG CCG GGC CAC TTC AAG GAC

ProLysArgLeuTyrCysLysLysAsnGlyGlyPhePheLeuArgIleHisProAspGlyArg    27
CCCAAGCGGCTGTACTGCAAAAACGGGGGCTTCTTCCTGCGCATCCACCCCGACGGCCGA      87

ValAspGlyValArgGluLysSerAspProHisIleLysLeuGlnLeuGlnAlaGluGlu      47
GTTGACGGGGTCCGGGAGAAGAGCGACCCCTCACATCAAGCTACAACTTCAAGCAGAAGAG   147

ArgGlyValValSerIleLysGlyValCysAlaAsnArgTyrLeuAlaMetLysGluAsp      67
AGAGGAGTTGTGTCTATCAAAGGAGTGTGTGCTAACCGTTACCTGGCTATGAAGGAAGAT   207

GlyArgLeuLeuAlaSerLysCysValThrAspGluCysPhePheGluArgLeuGluGlu      87
GGAAGATTACTGGCTTCTAAATGTGTTACGGATGAGTGTTTCTTTGAACGATTGGAA       267

SerAsnAsnTyrAsnThrTyrArgSerArgLysTyrThrSerTrpTyrValAlaLeuLys    107
TCTAATAACTACAATACTTACCGGTCAAGGAAATACACCAGTTGGTATGTGCACTGAAA    327

ArgThrGlyGlnTyrLysLeuGlySerLysThrGlyProGlyGlnLysAlaIleLeuPhe   127
CGAACTGGGCAGTATAAACTTGGATCCAAAACAGGACCTGGGCAGAAAGCTATACTTTTT  387

LeuProMetSerAlaLysSerTrm                                        134
CTTCCAATGTCTGCTAAGAGCTGA                                        411
```

Figure 41

```
MetProAlaLeuProGluAspGlyGlySerGlyAlaPheProProGlyHisPheLysAsp      20
ATGCCAGCATTGCCCGAGGATGGCGGCAGCGGCGCCTTCCCCGGCCACTTCAAGGAC        60

ProLysArgLeuTyrCysLysAsnGlyGlyPhePheLeuArgIleHisProAspGlyArg     40
CCCAAGCGGCTGTACTGCAAAAACGGGGGCTTCTTCCTGCGCATCCACCCCGACGGCCGA    120

ValAspGlyValArgGluLysSerAspProHisIleLysLeuGlnLeuGlnAlaGluGlu      60
GTTGACGGGGTCCGGGAGAAGAGCGACCCTCACATCAAGCTACAACTTCAAGCAGAAGAG    180

ArgGlyValValSerIleLysGlyValCysAlaAsnArgTyrLeuAlaMetLysGluAsp      80
AGAGGAGTTGTGTCTATCAAAGGAGTGTGTGCTAACCGTTACCTGGCTATGAAGGAAGAT    240

GlyArgLeuLeuAlaSer[trm]                                          86
GGAAGATTACTGGCTTCT TAA                                           300
                  GGTGTTACGGATGAGTGTTTCTTTTTGAACGATTGGAA

TCTAATAACTACAATACTTACCGGTCAAGGAAATACACCAGTTGGTATGTGGCACTGAAA    360

CGAACTGGGCAGTATAAACTTGGATCCAAAACAGGACCTGGGCAGAAAGCTATACTTTTT    420

CTTCCAATGTCTGCTAAGAGCTGA                                        444
```

Figure 42

```
MetProAlaLeuProGluAspGlyGlySerGlyAlaPheProProGlyHisPheLysAsp     20
ATGCCAGCCATTGCCCGAGGATGGCGGCAGCGGGGCCTTCCCGCCCGGCCACTTCAAGGAC    60

ProLysArgLeuTyrCysLysAsnGlyGlyPhePheLeuArgIleHisProAspGlyArg     40
CCCAAGCGGCTGTACTGCAAAAACGGGGGCTTCTTCCTGCGCATCCACCCCGACGGCCGA   120

ValAsnGlyValArgGluLysSerAspProHisIleLysLeuGlnLeuGlnAlaGluGlu     60
GTTAACGGAGTCCGGGAGAAGAGCGACCCCTCACATCAAGCTACAACTTCAAGCAGAAGAG   180

ArgGlyValValSerIleLysGlyValCysAlaAsnArgTyrLeuAlaMetLysGluAsp     80
AGAGGAGTTGTGTCTATCAAAGGAGTGTGTGCTAACCGTTACCTGGCTATGAAGGAAGAT   240

GlyArgLeuLeuAlaSerLysCysValThrAspGluCysPhePheGluArgLeuGlu      100
GGAAGATTACTGGCTTCTAAATGTGTTACGGATGAGTGTTTCTTTTTGAACGATTGGAA    300

SerAsnAsnTyrAsnThrTyrArgSerArgLysTyrThrSerTrpTyrValAlaLeuLys   120
TCTAATAACTACAATACTTACCGGTCAAGGAAATACACCAGTTGGTATGTGGCACTGAAA   360

ArgThrGlyGlnTyrLysLeuGlyProLysThrGlyProGlyGlnLysAlaIleLeuPhe   140
CGAACTGGGCAGTATAAACTTGGATCCAAAACAGGACCTGGGCAGAAAGCTATACTTTTT   420

LeuProMetSerAlaLysSertrm                                        147
CTTCCAATGTCTGCTAAGAGCTGA                                        444
```

Figure 43

```
MetProAlaLeuProGluProGluAspGlyGlySerGlyAlaPheProProGlyHisPheLysAsp          20
ATGCCAGCATTGCCCGAGCCGGAGGATGGCGGCAGCGGGGCCTTCCCGCCGGGCCACTTCAAGGAC          60

ProLysArgLeuTyrCysLysAsnGlyGlyPhePheLeuArgIleHisProAspGlyArg                40
CCCAAGCGGCTGTACTGCAAAAACGGGGGCTTCTTCCTGCGCATCCACCCCGACGGCCGA              120

ValAspGlyValGlnGluGlyLysSerAspProHisIleLysLeuGlnLeuGlnAlaGluGlu             60
GTTGACGGAGTCCAGGAGGGAAAGAGCGACCCTCACATCAAGCTACAACTTCAAGCAGAAGAG            180

ArgGlyValValSerIleLysGlyValCysAlaAsnArgTyrLeuAlaMetLysGluAsp                80
AGAGGAGTTGTCTCTATCAAAGGAGTGTGTGCTAACCGTTACCTGGCTATGAAGGAAGAT              240

GlyArgLeuLeuAlaSerLysCysValThrAspGluCysPhePheGluArgLeuGlu                  100
GGAAGATTACTGGCTTCTAAATGTGTTACGGATGAGTGTTTCTTTTTTGAACGATTGGAA              300

SerAsnAsnTyrAsnThrTyrArgSerArgLysTyrThrSerTrpTyrValAlaLeuLys               120
TCTAATAACTACAATACTTACCGGTCAAGGAAATACACCAGTTGGTATGTGGCACTGAAA              360

ArgThrGlyGlnTyrLysLeuGlySerLysThrGlyProGlyGlnLysAlaIleLeuPhe               140
CGAACTGGCCAGTATAAACTTGGATCCAAAACAGGACCTGGGCAGAAAGCTATACTTTTT              420

LeuProMetSerAlaLysSertrm                                                   147
CTTCCAATGTCTGCTAAGAGCTGA                                                   444
```

Figure 44

```
MetProAlaLeuProGluAspGlyGlySerGlyAlaPheProProGlyHisPheLysAsp         20
ATGCCAGCCATTGCCCGAGGATGGCGGCAGCGGCGCCTTCCCGCCCGGCCACTTCAAGGAC        60

ProLysArgLeuTyrCysLysAsnGlyGlyPhePheLeuArgIleHisProAspGlyArg         40
CCCAAGCGGCTGTACTGCAAAAACGGGGGCTTCTTCCTGCGCATCCACCCCGACGGCCGA       120

ValArgGlyValArgGluLysSerAspProHisIleLysLeuGlnLeuGlnAlaGluGlu         60
GTTAGAGGAGTCCGGGAGAAGAGCGACCCTCACATCAAGCTACAACTTCAAGCAGAAGAG       180

ArgGlyValValSerIleLysGlyValCysAlaAsnArgTyrLeuAlaMetLysGluAsp         80
AGAGGAGTTGTCTCTATCAAAGGAGTGTGCGCTAACCGTTACCTGGCTATGAAGGAAGAT       240

GlyArgLeuLeuAlaSerLysCysValThrAspGluCysPhePheGluArgLeuGluLys       100
GGAAGACTTCTGGCTTCTAAATGTGTTACGGATGAGTGTTTCTTTTTTGAACGATTGGAA       300

SerAsnAsnTyrAsnThrTyrArgSerArgLysTyrThrSerTrpTyrValAlaLeuLys       120
TCTAATAACTACAATACTTACCGGTCAAGGAAATACACCAGTTGGTATGTGGCACTGAAA       360

ArgThrGlyGlnTyrLysLeuGlySerLysThrGlyProGlyGlnLysAlaIleLeuPhe       140
CGAACTGGGCAGTATAAACTTGGATCCAAAACAGGACCTGGGCAGAAAGCTATACTTTTT       420

LeuProMetSerAlaLysSertrm                                           147
CTTCCAATGTCTGCTAAGAGCTGA                                           444
```

Figure 48

```
                    Met GlyAlaPheProProGlyHisPheLysAsp
         GAATTC    ATG GGCGCCTTCCCGGCCCGGCCACTTCAAGGAC
```

ProLysArgLeuTyrCysLysAsnGlyGlyPhePheLeuArgIleHisProAspGlyArg
CCCAAGCGGCTGTACTGCAAAAACGGGGGGCTTCTTCCTGCGCATCCACCCCGACGGCGA

ValAspGlyValArgGluLysSerAspProHisIleLysLeuGlnLeuAlaGluGluGlu
GTTGACGGGGTCCGGGAGAAGAGCGACCCTCACATCAAGCTACAACTTCAAGCAGAAGAG

ArgGlyValValSerIleLysGlyValCysAlaAsnArgTyrLeuAlaMetLysGluAsp
AGAGGAGTTGTGTCTATCAAAGGAGTGTGTGCTAACCGTTACCTGGCTATGAAGGAAGAT

GlyArgLeuLeuAlaSerLysCysValThrAspGluCysPhePheGluArgLeuGlu
GGAAGATTACTGGCTTCTAAATGTGTTACGGATGAGTGTTTCTTTTTTGAACGATTGGAA

SerAsnAsnTyrAsnThrTyrArgSerArgLysTyrThrThrSerTrpTyrValAlaLeuLys
TCTAATAACTACAATACTTACCGGTCAAGGAAATACACCAGTTGGTATGTGGCACTGAAA

ArgThrGlyGlnTyrLysLeuGlySerLysThrGlyProGlyGlnLysAlaIleLeuPhe
CGAACTGGGCAGTATAAACTTGGATCCAAAACAGGACCTGGGCAGAAAGCTATACTTTT

LeuProMetSerAlaLysSertrm
CTTCCAATGTCTGCTAAGAGCTGA

Figure 54

```
MetProAlaLeuProGluAspGlyGlySerGlyAlaPheProProGlyHisPheLysAsp         20
ATGCCAGCATTGCCCGAGGATGGGGGCAGCGGGGCCTTCCCGCCCGGCCACTTCAAGGAC         60

ProLysArgLeuTyrCysLysAsnGlyGlyPheLeuArgIleHisProAspGlyArg            40
CCCAAGCGGCTGTACTGCAAAAACGGGGGCTTCTTGCGCATCCACCCCGACGGCCGA           120

Val Asn Gly Ser Leu  GluLysSerAspProHisIleLysLeuGlnAlaGluGlu         60
GTT AAC GGA TCC CTG  GAGAAGAGCGACCCTCACATCAAGCTACAACTTCAAGCAGAAGAG  180

ArgGlyValValSerIleLysGlyValCysAlaAsnArgTyrLeuAlaMetLysGluAsp         80
AGAGGAGTTGTGTCTATCAAAGGAGTGTGTGCTAACCGTTACCTGGCTATGAAGGAAGAT       240

GlyArgLeuLeuAlaSerLysCysValThrAspGluCysPhePheGluArgLeuGlu          100
GGAAGATTACTGGCTTCTAAATGTGTTACGGATGAGTGTTTCTTTTTGAACGATTGGAA        300

SerAsnAsnTyrAsnThrTyrArgSerArgLysTyrThrSerTrpTyrValAlaLeuLys       120
TCTAATAACTACAATACTTACCGGTCAAGGAAATACACCAGTTGGTATGTGGCACTGAAA      360

ArgThrGlyGlnTyrLysLeuGlySerLysThrGlyProGlyGlnLysLysAlaIleLeuPhe    140
CGAACTGGGCAGTATAAACTTGGATCCAAAACAGGACCTGGGCAGAAAGCTATACTTTTT      420

LeuProMetSerAlaLysSertrm                                            147
CTTCCAATGTCTGCTAAGAGCTGA                                            444
```

Figure 57

MetAspGlyValArgGluLysSerAspProHisIleLysLeuGlnLeuGlnAlaGluGlu
ATGGACGGGGTCCGGGAGAAGAGCGACCCTCACATCAAGCTACAACTTCAAGCAGAAGAG

ArgGlyValValSerIleLysGlyValCysAlaAsnArgTyrLeuAlaMetLysGluAsp
AGAGGAGTTGTGTCTATCAAAGGAGTGTGTGCTAACCGTTACCTGGCTATGAAGGAAGAT

GlyArgLeuLeuAlaSerLysCysValThrAspGluCysPhePheGluArgLeuGlu
GGAAGATTACTGGCTTCTAAATGTGTTACGGATGAGTGTTTCTTTTTGAACGATTGGAA

SerAsnAsnTyrAsnThrTyrArgSerArgLysTyrThrSerTrpTyrValAlaLeuLys
TCTAATAACTACAATACTTACCGGTCAAGGAAATACACCAGTTGGTATGTGGCACTGAAA

ArgThrGlyGlnTyrLysLeuGlyGlyProGlyGlnLysAlaIleLeuPhe
CGAACTGGGCAGTATAAACTTGGATCCAAAACAGGACCTGGGCAGAAAGCTATACTTTTT

LeuProMetSerAlaLysSertrm
CTTCCAATGTCTGCTAAGAGCTGA

GAATTC

Figure 59

```
MetProAlaLeuProGluAspGlyGlySerGlyAlaPheProProGlyHisPheLysAsp    20
ATGCCAGCATTGCCCGAGGATGGGGGCAGCGGCGCCTTCCCGCCGGGCCACTTCAAGGAC    60

ProLysArgLeuTyrCysLysAsnGlyGlyPhePheLeuArgIleHisProAspGlyArg    40
CCCAAGCGGCTGTACTGCAAAAACGGGGGCTTCTTCCTGCGCATCCACCCCGACGGCCGA   120

ValAspGlyValArgGluLysSerAspProHisIleLysLeuGlnLeuAlaGluGlu       60
GTTGACGGGGTCCGGGAGAAGAGCGACCCTCACATCAAGCTACAACTTGCAGAAGAG      180

ArgGlyValValSerIleLysGlyValCysAlaAsnArgTyrLeuAlaMetLysGluAsp    80
AGAGGAGTTGTGTCTATCAAAGGAGTGTGTGCTAACCGTTACCTGGCTATGAAGGAAGAT  240

GlyArgLeuLeuAlaSerLysCysValThrAspGluCysPhePheGluArgLeuGlu      100
GGAAGATTACTGGCTTCTAAATGTGTTACGGATGAGTGTTTCTTTTGAACGATTGGAA    300

SerAsnAsnTyrAsnThrTyrArgSerArgLysTyrThrSerTrpTyrValAlaLeuLys   120
TCTAATAACTACAATACTTACCGGTCAAGGAAATACACCAGTTGGTATGTGGCACTGAAA  360

ArgThrGlyGlnTyrLysLeuGlySer trm                                 129
CGAACTGGGCAGTATAAACTTGGATCC TAG                                 390
```

Figure 62

```
MetProAlaLeuProGluAspGlyGlySerGlyAlaPheProProGlyHisPheLysAsp     20
ATGCCAGCATTGCCCGAGGATGGGGGCAGCGGGGCGTTCCCGCCACTTCAAGGAC          60

ProLysArgLeuTyrCysLysAsnGlyGlyPheGlyPheLeuArgIleHisProAspGlyArg   40
CCCAAGCGGCTGTACTGCAAAAACGGGGGCTTCGGCTTCCTGCGCATCCACCCCGACGGCCGA 120

ValAspGlyValValArgGluLeuLysSerAspProHisIleLysLeuGlnLeuAlaGluGlu   60
GTTGACGGGGTCGTCCGGGAGAAGAGCGACCCTCACATCAAGCTACAACTTCAAGCAGAAGAG 180

ArgGlyValValSerIleLysGlyValCysAlaAsnArgTyrLeuAlaMetLysGluAsp      80
AGAGGAGTTGTGTCTATCAAAGGAGTGTGCTAACCGTTACCTGGCTATGAAGGAAGAT      240

GlyArgLeuLeuAlaSerLysCysValThrAspGluCysPhePheGluArgLeuGlu        100
GGAAGATTACTGGCTTCTAAATGTGTTACGGATGAGTGTTTCTTTTTTGAACGATTGGAA    300

SertrmⅡ
TCCTAGCTAGCTAG
```

Figure 63

```
          MetProAlaLeuProGluAspGlyGlySerGlyAlaPheProProGlyHisPheLysAsp      20
          ATGCCAGCATTGCCCGAGGATGGCGGCAGCGGCGCCTTCCCGCCCGGCCACTTCAAGGAC         60

ProLysArgLeuTyrCysLysAsnGlyGlyPheLeuArgIleHisProAspGlyArg           40
          CCCAAGCGGCTGTACTGCAAAAACGGGGGCTTCCTGCGCATCCACCCCGACGGCCGA           120

ValAspGlyValArgGluLeuLysSerAspProHisIleLysLeuGlnLeuAlaGluGlu        60
          GTTGACGGGGTCCGGGAGAAGAGCGACCCCTCACATCAAGCTACAACTTCAAGCAGAAGAG       180

ArgGlyValValSerIleLysGlyValCysAlaAsnArgTyrLeuAlaMetLysGluAsp        80
          AGAGGAGTTGTGTCTATCAAAGGAGTGTGCTAACCGTTACCTGGCTATGAAGGAAGAT         240

GlyArgLeuLeuAlaSerLysCysPhePheGluArgLeuGlu                         100
          GGAAGATTACTGGCTTCTAAATGTGTTACGGATGAGTGTTTTTTTTGAACGATTGGAA          300

SerAsnAsnTyrAsn trm
          TCTAATAACTACAACTAGCTAGCTAG
```

Figure 64

```
MetProAlaLeuProGluAspGlyGlySerGlyAlaPheProProGlyHisPheLysAsp      20
ATGCCAGCATTGCCCGAGGATGGGGGCAGCGGGGCCTTCCCGCCCGGCCACTTCAAGGAC     60

ProLysArgLeuTyrCysLysLysAsnGlyGlyPheLeuArgIleHisProAspGlyArg     40
CCCAAGCGGCTGTACTGCAAAAACGGGGGCTTCCTGCGCATCCACCCCGACGGCCGA      120

ValAspGlyValArgGluLysSerAspProHisIleLysLeuGlnLeuGlnAlaGluGlu     60
GTTGACGGGGTCCGGGAGAAGAGCGACCCTCACATCAAGCTACAACTTCAAGCAGAAGAG    180

ArgGlyValValSerIleLysGlyValCysAlaAsnArgTyrLeuAlaMetLysGluAsp     80
AGAGGAGTTGTGTCTATCAAAGGAGTGTGTGCTAACCGTTACCTGGCTATGAAGGAAGAT    240

GlyArgLeuLeuAlaSerLysCysValThrAspGluCysPhePheGluArgLeuGlu       100
GGAAGATTACTGGCTTCTAAATGTGTTACGGATGAGTGTTTCTTTTTTGAACGATTGGAA    300

SerAsnAsnTyrAsnThrTyrArgSerArgLysTyrThrSer trm
TCTAATAACTACAATACTTACCGGTCAAGGAAATACACCAGCTAGCTAGCTAG
```

Figure 65

```
MetProAlaLeuProGluAspGlyGlySerGlyAlaPheProProGlyHisPheLysAsp      20
ATGCCAGCATTGCCCGAGGATGGGGGCAGCGGGGCCTTCCCGCCCGGCCACTTCAAGGAC      60

ProLysArgLeuTyrCysLysAsnGlyGlyPhePheLeuArgIleHisProAspGlyArg      40
CCCAAGCGGCTGTACTGCAAAAACGGGGGCTTCTTCCTGCGCATCCACCCCGACGGGCGA    120

ValAspGlyValValArgGluLysSerAspProHisIleLysLeuGlnLeuGlnAlaGluGlu  60
GTTGACGGGGTCCGGGAGAAGAGCGACCCTCACATCAAGCTACAACTTCAAGCAGAAGAG    180

ArgGlyValValSerIleLysGlyValCysAlaAsnArgTyrLeuAlaMetLysGluAsp     80
AGAGGAGTTGTGTCTATCAAAGGAGTGTGTGCTAACCGTTACCTGGCTATGAAGGAAGAT    240

GlyArgLeuLeuAlaSerLysCysValThrAspGluCysPhePheGluArgLeuGlu       100
GGAAGATTACTGGCTTCTAAATGTGTTACGGATGAGTGTTTCTTTTTTGAACGATTGGAA    300

SerAsnAsnTyrAsnThrTyrArgSerArgLysTyrThrSerTrpTyrValAlatrm
TCTAATAACTACAATACTTACCGGTCAAGGAAATACACCAGTTGGTATGTGGCCTAGCTAGCTAG
```

Figure 66

```
MetProAlaLeuProGluAspGlyGlySerGlyAlaPheProProGlyHisPheLysAsp                    20
ATGCCAGCATTGCCCGAGGATGGCGGCAGCGGGGCCTTCCCGCCGGCCACTTCAAGGAC                     60

ProLysArgLeuTyrCysLysLysAsnGlyGlyPheLeuArgIleHisProAspGlyArg                    40
CCCAAGCGGCTGTACTGCAAAAACGGGGGCTTCTTCCTGCGCATCCACCCCGACGGCCGA                   120

ValAspGlyValArgGluLysSerAspProHisIleLeuLeuGlnLeuAlaGluGlu                       60
GTTGACGGGGTCCGGGAGAAGAGCGACCCTCACATCAAGCTACAACTTCAAGCAGAAGAG                   180

ArgGlyValValSerIleLeuLysGlyValCysAlaAsnArgTyrLeuAlaMetLysGluAsp                 80
AGAGGAGTTGTGTCTATCAAAGGAGTGTGTGCTAACCGTTACCTGGCTATGAAGGAAGAT                   240

GlyArgLeuLeuAlaSerLysCysValThrAspGluCysPhePheGluArgLeuGlu                      100
GGAAGATTACTGGCTTCTAAATGTGTTACGGATGAGTGTTTCTTTTTTGAACGATTGGAA                   300

SerAsnAsnTyrAsnThrTyrArgSerArgLysTyrThrSerTrpTyrValAlaLeuLys                   120
TCTAATAACTACAATACTTACCGGTTCAAGGAAATACACCAGTTGGTATGTGGCACTGAAA                  360

ArgThrGlytrm
CGAACTGGCTAGCTAGCTAG
```

Figure 67

```
    MetProAlaLeuProGluAspGlyGlySerGlyAlaPheProProGlyHisPheLysAsp      20
    ATGCCAGCATTGCCCGAGGATGGCGGCAGCGGGGCCTTCCCGCCGGGCCACTTCAAGGAC      60

ProLysArgLeuTyrCysLysLysAsnGlyGlyPheLeuArgIleHisProAspGlyArg      40
    CCCAAGCGGCTGTACTGCAAAAACGGGGGCTTCCTGCGCATCCACCCCGACGGCCGA       120

ValAspGlyValValArgGluLysSerAspProHisIleLysLeuGlnLeuAlaGluGlu      60
    GTTGACGGGGTCGGGAGAGAGCGACCCTCACATCAAGCTACAACTTCAAGCAGAAGAG      180

ArgGlyValValSerIleLysGlyValCysAlaAsnArgTyrLeuAlaMetLysGluAsp      80
    AGAGGAGTTGTGTCTATCAAAGGAGTGTGCTAACCGTTACCTGGCTATGAAGGAAGAT     240

GlyArgLeuLeuAlaSerLysCysValThrAspGluCysPhePhePheGluArgLeuGlu     100
    GGAAGATTACTGGCTTCTAAATGTGTTACGGATGAGTGTTTCTTTTTTGAACGATTGGAA    300

SerAsnAsnTyrAsnThrTyrArgSerArgLysTyrThrSerTrpTyrValAlaLeuLys    120
    TCTAATAACTACAATACTTACCGGTCAAGGAAATACACCAGTTGGTATGTGGCACTGAAA   360

ArgThrGlyGlnTyrLysLeuGlySer trm
    CGAACTGGGCAGTATAAACTTGGATCCTAGCTAGCTAG
```

Figure 68

```
      MetProAlaLeuProGluProAspGlyGlySerGlyAlaPheProProGlyHisPheLysAsp              20
      ATGCCAGCATTGCCCGAGCCAGAGGATGGGCGGGGCCAGCGGCGCCTTCCCGCCACTTCAAGGAC             60

ProLysArgLeuTyrCysLysAsnGlyGlyPhePheLeuArgIleHisProAspGlyArg                  40
      CCCAAGCGGCTGTACTGCAAAAACGGGGGCTTCTTCCTGCGCATCCACCCCGACGGCCGA                  120

ValAspGlyValArgGluLysSerAspProHisIleLysLeuGlnLeuGlnAlaGluGlu                  60
      GTTGACGGGGTCCGGGAGAAGAGCGACCCTCACATCAAGCTACAACTTCAAGCAGAAGAG                  180

ArgGlyValValSerIleLysGlyValCysAlaAsnArgTyrLeuAlaMetLysGluAsp                  80
      AGAGGAGTTGTCTCTATCAAAGGAGTGTGTGCTAACCGTTACCTGGCTATGAAGGAAGAT                  240

GlyArgLeuLeuAlaSerLysCysValThrAspGluCysPhePheGluArgLeuGlu                    100
      GGAAGATTACTGGCTTCTAAATGTGTTACGGATGAGTGTTTCTTTTTTGAACGATTGGAA                  300

SerAsnAsnTyrAsnThrTyrArgSerArgLysTyrThrSerTrpTyrValAlaLeuLys                 120
      TCTAATAACTACAATACTTACCGGTCAAGGAAATACACCAGTTGGTATGTGGCACTGAAA                  360

ArgThrGlyGlnTyrLysLeuGlyProGlyGlnLysAlaSertrm
      CGAACTGGGCAGTATAAACTTGGATCCAAAACAGGACCTGGGCAGAAAAGCTAGCTAG
```

Figure 71

```
MetProAlaLeuProGluAspGlyGlySerGlyAlaPheProProGlyHisPheLysAsp   20
ATGCCAGCATTGCCCGAGGATGGGGGCAGCGGGGCCTTCCCGCCCGGCCACTTCAAGGAC   60

ProLysArgLeuTyrCysLysAsnGlyGlyPhePheLeuArgIleHisProAspGlyArg   40
CCCAAGCGGCTGTACTGCAAAAACGGGGGCTTCTTCCTGCGGCATCCACCCCGACGGCCGA  120

ValAspGlyValArgGluLysLeuLeuGlnLeuAlaGluGlu                    60
GTTGACGGGGTCCGGGAGAAGAGACCCTCACATCAAGCTACAACTTCAAGCAGAAGAG    180

ArgGlyValValSerIleLysGlyValSerAlaAsnArgTyrLeuAlaMetLysGluAsp   80
AGAGGAGTTGTGTCTATCAAAGGAGTGAGC GCTAATCGTTACCTGGCTATGAAGGAAGAT  240

GlyArgLeuLeuAlaSerLys Ser ValThrAspGluCysPhePheGluArgLeuGlu   100
GGAAGATTACTAGCTTCTAAA TCT GTTACGGATGAGTGTTTCTTTTTGAACGATTGGAA   300

SerAsnAsnTyrAsnThrTyrArgSerArgLysTyrThrSerTrpTyrValAlaLeuLys  120
TCTAATAACTACAATACTTACCGGTCAAGGAAATACACCAGTTGGTATGTGGCACTGAAA  360

ArgThrGlyGlnTyrLysLeuGlySertrm
CGAACTGGGCAGTATAAACTTGGATCCTAGCTAGCTAG
```

Figure 72

```
                                                                                      20
MetProAlaLeuProGluAspGlyGlySerGlyAlaPheProProGlyHisPheLysAsp
ATGCCAGCATTGCCCGAGGATGGCGGCAGCGGGGCCTTCCCGCCCGGCCACTTCAAGGAC                         60

40
ProLysArgLeuTyrCysLysAsnGlyGlyPhePheLeuArgIleHisProAspGlyArg
CCCAAGCGGCTGTACTGCAAAAACGGGGGCTTCTTCCTGCGCATCCACCCCGACGGCCGA                        120

60
ValAspGlyValArgGluLysSerAspProHisIleLysLeuGlnLeuAlaGluGluGlu
GTTGACGGGGTCCGGGAGAAGAGCGACCCTCACATCAAGCTACAACTTCAAGCAGAAGAG                        180

80
ArgGlyValValSerIleLysGlyValSerAlaAsnArgTyrLeuAlaMetLysGluAsp
AGAGGAGTTGTGTCTATCAAAGGAGTGAGCGCTAATCGTTACCTGGCTATGAAGGAAGAT                        240

100
GlyArgLeuLeuAlaSerLysSerValThrAspGluCysPhePheGluArgLeuGlu
GGAAGATTACTAGCTTCTAAATCTGTTACGGATGAGTGTTTCTTTTTTGAACGATTGGAA                        300

120
SerAsnAsnTyrAsnThrTyrArgSerArgLysTyrThrSerTrpTyrValAlaLeuLys
TCTAATAACTACAATACTTACCGGTCAAGGAAATACACCAGTTGGTATGTGGCACTGAAA                        360

ArgThrGlyGlnTyrLysLeuGlySerLysThrGlyProGlyGlnLysAlaSertrm
CGAACTGGGCAGTATAAACTTGGATCCAAAACAGGACCTGGGCAGAAAAGCTAGCTAG
```

BASIC FIBROBLAST GROWTH FACTOR (BFGF) MUTEINS

This application is a Continuation-in-part application of U.S. patent application Ser. No. 161,123, filed Feb. 18, 1988 now abandoned.

The present invention relates to muteins of basic fibroblast growth factors (hereinafter also briefly referred to as bFGF), a recombinant DNA segment having a base sequence which codes for a mutein of bFGF and its use.

bFGF is a basic polypeptide hormone having a molecular weight of about 17,000 secreted mainly by the pituitary gland, and was first separated as a factor exhibiting strong growth promoting action on fibroblasts such as BALB/c3T3 [D. Gospodarowicz; Nature, 249, 123 (1974)]. Thereafter, however, it was proven that it exhibits growth promoting action on almost all cells deriving from mesoblast [D. Gospodarowicz et al.; National Cancer Institute Monograph, 48, 109 (1978)]. Specifically, the angiogenic action of bFGF, together with its cell growth promoting action, suggests a potential for the application thereof as a therapeutic drug for traumas and as a preventive and therapeutic drug for thrombosis, arteriosclerosis, etc.

Bovine bFGF was described in the Proceedings of the National Academy of Sciences of the United States of America, Vol. 82, pp. 6507 (1985). In Science, 233, 545 (1986), the bovine bFGF-constituent amino acids deduced from a clone which was produced by cloning cDNA of human bFGF were discussed.

Biochemical and Biophysical Research Communications, Vol. 135, p. 541 (1986) stated that human bFGF was extracted from human brain.

European Molecular Biology Organization (EMBO) Journal, Vol 5, p. 2523 (1986) and PCT International Publication No. WO/87/101728, state that human bFGF-constituent amino acids were deductively specified on the basis of a clone which was produced by cloning cDNA of human bFGF using bovine bFGF as a probe.

In addition, FEBS Letters, 213, 189 (1987), describes the production of human bFGF by cultivation of a transformant obtained by cloning cDNA of human bFGF.

Comparing human bFGF and bovine bFGF indicate that the human one has Thr for the 112-position, while the bovine one, Ser; the human one Ser for the 128-position, while the bovine one has Pro. (In this case, the N-terminal Pro is determined as the 1st amino acid).

The present inventors determined that modifications in the amino acid sequence improved stability, productivity in a cell and cell proliferating activity per molecule of bFGF, and, in addition, its unidentified bioactivities were potentiated.

In addition, biologically active proteins microbiologically produced by DNA recombination technique contain cysteine residues, which are not essential to their activities but which may form undesirable intermolecular or intramolecular linkages.

In the course of a production of bFGF by recombinant DNA technique, heterogeneous conformations were found in *Escherichia coli* extract containing a high concentration of bFGF. These conformations are thought to have been produced due to random intra-or inter-molecular disulfide bridging, and cause difficulties in bFGF purification and reduce its recovery.

The present inventors decided it would be useful if one could modify microbiologically produced bioactive proteins such as recombinant bFGF so that, their activities are not affected adversely, but their capabilities of forming such intermolecular bridges and intramolecular linkages as will result in the formation of undesirable tertiary structures (e.g., conformations which lower the activity of the protein) are reduced or eliminated.

bFGF is known to induce cellular changes like those found in malignant cells when expressed in excess in animal cells or expressed in the presence of the signal peptide of a foreign protein as an adduct thereto [R. Sasada, Molecular and Cellular Biology, 8, 588 (1988); S. Rogelj, Nature, 331, 173 (1988)].

It is desired that a bFGF mutein having none of the above-mentioned undesirable properties will be produced. This is particularly advantageous with respect to using bFGF in pharmaceuticals.

The present inventors investigated various bFGF muteins, and determined that amino acid-lacking muteins can be useful.

The present inventors constructed modified bFGF muteins by DNA recombination and site-directed mutagenesis, and made investigations to improve their stability, upgrade their intracellular productivities and activities, and determine changes in their bioactivities; as a result of this research, the present inventors created muteins which met their objectives. The present inventors made further investigations based on this finding, and completed the present invention.

The present invention involves:

(1) muteins of a basic fibroblast growth factor (bFGF),
(2) a recombinant DNA segment having a base sequence which codes for the above-mentioned muteins (1),
(3) a transformant harboring a vector containing a recombinant DNA segment having the base sequence which codes for the above-mentioned muteins (1), and
(4) a method for producing the above-mentioned muteins (1) which comprises cultivating a transformant harboring a vector containing a recombinant DNA segment having the base sequence which codes for the said muteins in a culture medium to produce and accumulate in the culture broth.

In the preferred embodiment, the present invention involves:

(a) a mutein of bFGF which lacks 7 to 46 amino acid residues from the carboxyl terminal,
(b) a mutein as claimed in claim 1, wherein at least one constituent amino acid may be replaced by another amino acid and at least one amino acid may be added to the amino terminal,
(c) a DNA segment having a base sequence which codes for the above-mentioned mutein (a) or (b),
(d) a transformant harboring a vector containing a recombinant DNA segment having a base sequence which codes for the above-mentioned mutein (a) or (b), and
(e) a method of producing the above-mentioned mutein (a) or (b), characterized in that a transformant harboring a vector containing a recombinant DNA segment having a base sequence which codes for said mutein is cultivated in a culture medium to produce and accumulate said mutein in the culture broth.

Mutein (a) above may undergo both the above-mentioned replacement and addition.

For bFGF, any bFGF can be included, as long as it derives from a warm-blooded mammal.

Typical examples thereof include human, bovine and murine bFGFs.

Polypeptides which include the amino acid sequence represented as follows:

Phe-Phe-Leu-Arg-Ile-His-Pro-Asp-Gly-Arg-Val-Asp-Gly-Val-Arg-Glu-Lys-Ser-Asp-Pro  [I]

are preferable.

More preferably, the polypeptides are represented by the formula:

Pro — Ala — Leu — Pro — Glu — Asp — Gly — Gly — Gly — Ala — Phe — Pro — Pro — Gly — His — Phe —  [III]
Lys — Asp — Pro — Lys — Arg — Leu — Tyr — Cys — Lys — Asn — Gly — Gly — Phe — Phe — Leu — Arg —
Ile — His — Pro — Asp — Gly — Arg — Val — Asp — Gly — Val — Arg — Glu — Lys — Ser — Asp — Pro —
His — Val — Lys — Leu — Gln — Leu — Gln — Ala — Glu — Glu — Arg — Gly — Val — Val — Ser — Ile —
Lys — Gly — Val — Cys — Ala — Asn — Arg — Tyr — Leu — Ala — Met — Lys — Glu — Asp — Gly — Arg —
Leu — Leu — Ala — Ser — Lys — Cys — Val — Thr — Glu — Glu — Cys — Phe — Phe — Phe — Glu — Arg —
Leu — Glu — Ser — Asn — Asn — Tyr — Asn — Thr — Tyr — Arg — Ser — Arg — Lys — Tyr — Ser — Ser —
Trp — Tyr — Val — Ala — Leu — Lys — Arg — Thr — Gly — Gln — Tyr — Lys — Leu — Gly — Ser — Lys —
Thr — Gly — Pro — Gly — Gln — Lys — Ala — Ile — Leu — Phe — Leu — Pro — Met — Ser — Ala — Lys —
Ser in which X represents Thr or Ser; when X is Thr, Y represents Ser, and when X is Ser, Y represents Pro Polypeptides containing the amino acid sequence:

are even more preferable.

The muteins of the present invention essentially have the amino acid sequence of the original peptide or protein; but variations include an addition of amino acid(s), deletion of constituent amino acid(s) and substitution of constituent amino acid(s) by other amino acid(s), and the present muteins possess at least one of the activities of fibroblast growth promoting activity, growth stimulating activity of capillary endothelial cells and angiogenic activity.

Such addition of amino acid includes addition of at least one amino acid.

Such deletion of constituent amino acid includes deletion of at least one bFGF-constituent amino acid.

Such substitution of constituent amino acid by other amino acids includes substitution of at least one bFGF-constituent amino acid by other amino acid.

The at least one amino acid in the mutein which has at least one amino acid added to bFGF excludes methionine deriving from initiation codon used for peptide expression and signal peptide.

The number of added amino acids is at least 1, but it may be any one, as long as bFGF characteristics are not lost. Preferably the amino acids added should include some or all of the amino acid sequences of proteins which have homology with bFGF and which exhibit activities similar to those of bFGF.

As examples of such added amino acids, mention may be made of a part or all of the amino acid sequences of proteins such as acidic fibroblast growth factors (aFGF), interleukin 1-α (IL1-α), interleukin 1-β(IL1-β), and a protein which is coded by int-2 in oncogenes.

Such aFGFs include those deriving from humans and those deriving from bovines. Such IL1-αs and IL1-βs include those deriving from humans.

Amino acid sequences of such bovine aFGFs include:

NH$_2$ — Phe — Asn — Leu — Pro — Leu — Gly — Asn — Tyr — Lys — Lys — Pro — Lys — Leu — Leu —
Tyr — Cys — Ser — Asn — Gly — Gly — Tyr — Phe — Leu — Arg — Ile — Leu — Pro — Asp — Gly — Thr —
Val — Asp — Gly — Thr — Lys — Asp — Arg — Ser — Asp — Gln — His — Ile — Gln — Leu — Gln — Leu —
Cys — Ala — Glu — Ser — Ile — Gly — Glu — Val — Tyr — Ile — Lys — Ser — Thr — Glu — Thr — Gly —
Gln — Phe — Leu — Ala — Met — Asp — Thr — Asp — Gly — Leu — Leu — Tyr — Gly — Ser — Gln — Thr —
Pro — Asn — Glu — Glu — Cys — Leu — Phe — Leu — Glu — Arg — Leu — Glu — Glu — Asn — His —
Tyr — Asn — Thr — Tyr — Ile — Ser — Lys — Lys — His — Ala — Glu — Lys — His — Trp — Phe — Val —
Gly — Leu — Lys — Lys — Asn — Gly — Arg — Ser — Lys — Leu — Gly — Pro — Arg — Thr — His — Phe —
Gly — Gln — Lys — Ala — Ile — Leu — Phe — Leu — Pro — Leu — Pro — Val — Ser — Ser — Asp — COOH

Amino acid sequences of human IL1-α include:

NH$_2$ — Met — Ala — Lys — Val — Pro — Asp — Met — Phe — Glu — Asp — Leu — Lys — Asn — Cys —

-continued

Tyr—Ser—Glu—Asn—Glu—Glu—Asp—Ser—Ser—Ser—Ile—Asp—His—Leu—Ser—Leu—
Asn—Gln—Lys—Ser—Phe—Tyr—His—Val—Ser—Tyr—Gly—Pro—Leu—His—Glu—Gly—
Cys—Met—Asp—Gln—Ser—Val—Ser—Leu—Ser—Ile—Ser—Glu—Thr—Ser—Lys—Thr—
Ser—Lys—Leu—Thr—Phe—Lys—Glu—Ser—Met—Val—Val—Ala—Thr—Asn—Gly—
Lys—Val—Leu—Lys—Lys—Arg—Arg—Leu—Ser—Leu—Ser—Gln—Ser—Ile—Thr—Asp—
Asp—Asp—Leu—Glu—Ala—Ile—Ala—Asn—Asp—Ser—Glu—Glu—Ile—Ile—|Lys|—
                                                              |Asn|
Pro—'Arg—Ser—Ala—Pro—Phe—Ser—Phe—Leu—Ser—Asn—Val—Lys—Tyr—Asn—Phe—
Met—Arg—Ile—Ile—Lys—Tyr—Glu—Phe—Ile—Leu—Asn—Asp—Ala—Leu—Asn—Gln—
Ser—Ile—Ile—Arg—Ala—Asn—Asp—Gln—Tyr—Leu—Thr—Ala—Ala—Ala—Leu—His—
Asn—Leu—Asp—Glu—Ala—Val—Lys—Phe—Asp—Met—Gly—Ala—Tyr—Lys—Ser—Ser—
Lys—Asp—Asp—Ala—Lys—Ile—Thr—Val—Ile—Leu—Arg—Ile—Ser—Lys—Thr—Gln—
Leu—Tyr—Val—Thr—Ala—Gln—Asp—Glu—Asp—Gln—Pro—Val—Leu—Leu—Lys—Glu—
Met—Pro—Glu—Ile—Pro—Lys—Thr—Ile—Thr—Gly—Ser—Glu—Thr—Asn—Leu—Leu—
Phe—Phe—Trp—Glu—Thr—His—Gly—Thr—Lys—Asn—Tyr—Phe—Thr—Ser—Val—Ala—
His—Pro—Asn—Leu—Phe—Ile—Ala—Thr—Lys—Gln—Asp—Tyr—Trp—Val—Cys—Leu—
Ala—Gly—Gly—Pro—Pro—Ser—Ile—Thr—Asp—Phe—Gln—Ile—Leu—Glu—Asn—Gln—
Ala—COOH

Amino acid sequences of human IL1-β include:

NH$_2$—Met—Ala—Glu—Val—Pro—Glu—Leu—Ala—Ser—Glu—Met—Met—Ala—Tyr—
Tyr—Ser—Gly—Asn—Glu—Asp—Asp—Leu—Phe—Phe—Glu—Ala—Asp—Gly—Pro—Lys—
Gln—Met—Lys—Cys—Ser—Phe—Gln—Asp—Leu—Asp—Leu—Cys—Pro—Leu—Asp—
Gly—Gly—Ile—Gln—Leu—Arg—Ile—Ser—Asp—His—His—Tyr—Ser—Lys—Gly—Phe—
Arg—Gln—Ala—Ala—Ser—Val—Val—Val—Ala—Met—Asp—Lys—Leu—Arg—Lys—Met—
Leu—Val—Pro—Cys—Pro—Gln—Thr—Phe—Gln—Glu—Asn—Asp—Leu—Ser—Thr—Phe—
Phe—Pro—Phe—Ile—Phe—Glu—Glu—Glu—Pro—Ile—Phe—Phe—Asp—Thr—Trp—Asp—
Asn—Glu—Ala—Tyr—Val—His—Asp—Ala—Pro—Val—Arg—Ser—Leu—Asn—Cys—Thr—
Leu—Arg—Asp—Ser—Gln—Gln—Lys—Ser—Leu—Val—Met—Ser—Gly—Pro—Tyr—Glu—
Leu—Lys—Ala—Leu—His—Leu—Gln—Gly—Gln—Asp—Met—Glu—Gln—Gln—Val—Val—
Phe—Ser—Met—Ser—Phe—Val—Gln—Gly—Glu—Glu—Ser—Asn—Asp—Lys—Ile—Pro—
Val—Ala—Leu—Gly—Leu—Lys—Glu—Lys—Asn—Leu—Tyr—Leu—Ser—Cys—Val—Leu—
Lys—Asp—Asp—Lys—Pro—Thr—Leu—Gln—Leu—Glu—Ser—Val—Asp—Pro—Lys—Asn—
Tyr—Pro—Lys—Lys—Lys—Met—Glu—Lys—Arg—Phe—Val—Phe—Asn—Lys—Ile—Glu—
Ile—Asn—Asn—Lys—Leu—Glu—Phe—Glu—Ser—Ala—Gln—Phe—Pro—Asn—Trp—Tyr—
Ile—Ser—Thr—Ser—Gln—Ala—Glu—Asn—Met—Pro—Val—Phe—Leu—Gly—Gly—Thr—
Lys—Gly—Gly—Gln—Asp—Ile—Thr—Asp—Phe—Thr—Met—Gln—Phe—Val—Ser—Ser—
COOH

Amino acid sequences encoded to int-2 include:

NH$_2$—Met—Gly—Leu—Ile—Trp—Leu—Leu—Leu—Leu—Ser—Leu—Leu—Glu—Pro—Ser—
Trp—Pro—Thr—Thr—Gly—Pro—Gly—Thr—Arg—Leu—Arg—Arg—Asp—Ala—Gly—Gly—
Arg—Gly—Gly—Val—Tyr—Glu—His—Leu—Gly—Gly—Ala—Pro—Arg—Arg—Arg—Lys—
Leu—Tyr—Cys—Ala—Thr—Lys—Tyr—His—Leu—Gln—Leu—His—Pro—Ser—Gly—Arg—
Val—Asn—Gly—Ser—Leu—Glu—Asn—Ser—Ala—Tyr—Ser—Ile—Leu—Glu—Ile—Thr—
Ala—Val—Glu—Val—Gly—Val—Val—Ala—Ile—Lys—Gly—Leu—Phe—Ser—Gly—Arg—
Tyr—Leu—Ala—Met—Asn—Lys—Arg—Gly—Arg—Leu—Tyr—Ala—Ser—Asp—His—Tyr—
Asn—Ala—Glu—Cys—Glu—Phe—Val—Glu—Arg—Ile—His—Glu—Leu—Gly—Tyr—Asn—
Thr—Tyr—Ala—Ser—Arg—Leu—Tyr—Arg—Thr—Gly—Ser—Ser—Gly—Pro—Gly—Ala—
Gln—Arg—Gln—Pro—Gly—Ala—Gln—Arg—Pro—Trp—Tyr—Val—Ser—Val—Asn—Gly—
Lys—Gly—Arg—Pro—Arg—Arg—Gly—Phe—Lys—Thr—Arg—Arg—Thr—Gln—Lys—Ser—
Ser—Leu—Phe—Leu—Pro—Arg—Val—Leu—Gly—His—Lys—Asp—His—Glu—Met—Val—
Arg—Leu—Leu—Gln—Ser—Ser—Gln—Pro—Arg—Ala—Pro—Gly—Glu—Gly—Ser—Gln—
Pro—Arg—Gln—Arg—Arg—Gln—Lys—Lys—Gln—Ser—Pro—Gly—Asp—His—Gly—Lys—
Met—Glu—Thr—Leu—Ser—Thr—Arg—Ala—Thr—Pro—Ser—Thr—Gln—Leu—His—Thr—
Gly—Gly—Leu—Ala—Val—Ala—COOH

As for the number of deleted bFGF-constituent amino acids in the present mutein which lacks at least 1 bFGF-constituent amino acid, it may be any one, as long as any characteristic of bFGF is not lost.

Examples of such deleted constituent amino acids include: the deletion of amino acids from amino terminal or carboxyl terminal; the deletion of the 10 residues in the amino terminal of human bFGF:

Met-Pro-Ala-Leu-Pro-Glu-Asp-Gly-Gly-Ser the 14 residues in the amino terminal of human bFGF:

Met-Pro-Ala-Leu-Pro-Glu-Asp-Gly-Gly-Ser-Gly-Ala-Phe-Pro the 41 residues in the amino terminal of human bFGF:

1   2   3   4           41
Met—Pro—Ala—Leu— ... —Val or the 61 residues in the carboxyl terminal of human bFGF:

87  88         146  147
Lys—Cys— ... —Lys—Ser.

Muteins of the present invention which lacks 7 to 46 constituent amino acids of the original bFGF peptide or protein from the carboxyl terminal are preferred. As examples of the preferred amino acid sequences to be deleted include the amino acid sequences respectively starting at rhbFGF amino acid Nos. 102, 106, 115, 119, 124, 130, and 138. These amino acid sequences may be replaced by another amino acid.

The number of bFGF-constituent amino acids that may be substituted by other amino acids, it may be any number, as long as any characteristic of bFGF is not lost.

Examples of constituent amino acids which may be substituted include cysteine and other amino acids but cysteine is preferable. As the constituent amino acid other than cysteine which may be substituted for, examples include but are not limited to aspartic acid, arginine, glycine, serine, valine and so forth.

When the constituent amino acid before substitution is cysteine, the substituted amino acids are preferably, for example, neutral amino acids. As specific examples of such neutral amino acids, mention may be made of glycine, valine, alanine, leucine, isoleucine, tyrosine, phenylalanine, histidine, tryptophan, serine, threonine and methionine. Serine and threonine are preferable.

When the constituent amino acid before substitution is other than cysteine, the substituted amino acids are selected from amino acids which are different from the amino acid before substitution in a property such as hydrophilicity, hydrophobicity or electric charge.

When the constituent amino acid before substitution is aspartic acid, examples of the substituted amino acids include asparagine, threonine, valine, phenylalanine and arginine; asparagine and arginine are preferable.

When the constituent amino acid before substitution is arginine, examples of the substituted amino acids include glutamine, threonine, leucine, phenylalanine and aspartic acid; glutamine is preferable.

When the constituent amino acid before substitution is glycine, examples of the substituted amino acids include threonine, leucine, phenilalanine, serine, glutamic acid, and arginine; threonine is preferable.

When the constituent amino acid before substitution is serine, examples of the substituted amino acids include methionine, alanine, leucine, cysteine, glutamine, arginine and aspartic acid; methionine is preferable.

When the constituent amino acid before substitution is valine, examples of the substituted amino acids include serine, leucine, proline, glycine, lysine, and aspartic acid; serine is preferable.

When the constituent amino acid to be replaced is isoleucine, examples of the substituted amino acid include serine, glycine, valine, alanine, leucine, tyrosine, phenylalanine, histidine, tryptophan, and methionine; serine is preferred.

The constituent amino acid before substitution are preferably aspartic acid, arginine, glycine, serine and valine.

The substituted amino acid is preferably asparagine, glutamine, arginine, threonine, methionine, serine, and leucine.

The embodiment of the substitution in the mutein wherein there is a substitution of serine for cysteine (i.e. cysteine is replaced by serine) is most preferred.

In said substitution, there may be at least 2 substitutions, and two or three substitutions are preferred.

The muteins of the present invention include combination of 2 or 3 of the above-mentioned additions, deletions and substitutions.

In addition to conventional DNA recombination technique, site-directed mutagenesis is employed to produce the mutein of the present invention. This technique is well-known, and is described in Genetic Engineering, Lather, R. F. and Lecoq, J. P., Academic Press, pp. 31 to 50 (1983). Mutagenesis directed to oligonucleotide is described in Genetic Engineering: Principles and Methods, Smith, M. and Gillam, S., Plenum Press, Vol. 3, pp. 1 to 32 (1981).

The production of the structural gene which encodes the mutein of the present invention is, for example, carried out by:

(a) hybridizing with a mutagenic oligonucleotide primer a single-stranded DNA comprising 1 strand of the structural gene of bFGF, (b) elongating the primer using DNA polymerase to form a mutational heteroduplex, and (c) replicating this mutational heteroduplex.

The size of oligonucleotide primer used depends upon conditions necessary for stable hybridization of the primer to the gene region to which mutation is to be introduced. Limitations in currently available methods of oligonucleotide synthesis also affect which size is preferable. The factors to be considered in designing oligonucleotide intended for the use for mutagenesis directed by the oligonucleotide (e.g., the overall size of the nucleotide and the size of the mismatching portion at the mutation site) are well known and, for example, are described by Smith, M. and Gillam, S. in the above-mentioned literature. In general, the overall length of the oligonucleotide is adjusted to such length that stable and unique hybridization at the mutation site is optimized, and the extensions between the mutation site and the 5'- and 3'-terminals are provided with sufficient sizes to prevent mutation induced by the exonuclease activity of DNA polymerase.

The oligonucleotides used for mutagenesis in accordance with the present invention normally contain some 12 to 24 bases, preferably 14 to 20 bases, and more preferably 14 to 18 bases. These normally contain at least about 3 base 3'-terminal of the codons to be changed.

For the purpose of obtaining, for example, a mutein having an added amino acid, a mutagenic bFGF gene is produced by synthesizing the gene which encodes the amino acid sequence to be added, and, directly or after fragmentation by digestion with an appropriate restriction enzyme, inserting or adding it into an appropriate site in the bFGF gene using DNA ligase. When any suitable restriction enzyme recognition site is not present in the bFGF gene, restriction enzyme recognition sites may be produced by the above-mentioned site-directed mutagenesis.

For the purpose of obtaining, for example, a mutein lacking bFGF-constituent amino acids, a mutagenic bFGF gene may be produced in 3 different ways. In one of the 3 cases, the amino terminal of bFGF is deleted; in another case, a central region of bFGF is deleted; and in the remaining one case, the carboxyl terminal is deleted.

In the case of deletion of the amino terminal, a codon of the gene which encodes the carboxyl terminal of the amino acid sequence to be deleted is changed to the Met-encoding codon ATG by site-directed mutagenesis, and the codon has an appropriate restriction enzyme recognition site produced in the 5'-terminal side thereof to facilitate its ligation to the promoter.

In the case of deletion of a central region of the amino acid sequence, a unique restriction enzyme recognition site is produced, by site-directed mutagenesis, in each of the 5'-terminal and 3'-terminal sides of the gene which encodes the sequence to be deleted, and the relevant gene is cleaved off from the gene by enzymatic digestion, and this is followed by re-ligation of the remaining 2 gene fragments to construct the desired gene which encodes bFGF lacking the specified amino acids. It is of course necessary not to shift the reading frame due to the digestion with the restriction enzymes.

In the case of deletion of an amino acid sequence in the carboxyl terminal side, a codon of the gene which encodes amino-terminal amino acids of the sequence to be deleted is changed to a stop codon by site-directed mutagenesis.

For the purpose of obtaining a mutein which has had the constituent amino acid cysteine substituted, a mutagenic bFGF gene is produced by eliminating, for example, the Cys-expression codon or inducing site-directed mutagenesis in the Cys-expression codon TGC or TGT using a synthetic nucleotide primer which so changes the codon that it encodes a different amino acid. A primer is hybridized with a sense chain of the FGF gene, for example, to change cysteine (26-position) of human bFGF to serine. As an appropriate nucleotide primer, there may be mentioned, for example, 5'-CGTTCTT<u>GCT</u>GTAGAGCCGCT-3', in which the underlined triplet represents the changed codon.

As an appropriate primer in changing cysteine (70-position) to serine, there may be mentioned 5'-AACGATTAGC<u>GCT</u>CACTC-3', in which the underlined triplet represents the changed codon.

As an appropriate primer for changing cysteine (88-position) to serine, there may be mentioned 5'-GTAAC<u>AGA</u>CTTAGAAGCTAGT-3', in which the underlined triplet represents the changed codon.

As an appropriate primer for changing cysteine (93-position) to serine, there may be mentioned 5'-TCGAAGAAGAA<u>AGA</u>CTCATCC-3', in which the underlined triplet represents the changed codon.

In the case of Cys (26-position), cysteine changes to serine via T→A transpostition of the 1st base; in the case of Cys (70-position), cysteine changes to serine via T→A transposition of the 1st base and T→C transposition of the 2nd base; and in the case of Cys (88-position, 93-position), cysteine changes to serine via G→C transposition of the 2nd base.

It should be noted that, in producing bFGF mutein protein by site-directed mutagenesis, 2 or more variations may be induced in the DNA sequence, that is, the DNA codons corresponding to the amino acids have degenerated.

For the purpose of obtaining a mutein which has had a constituent amino acid other than cysteine substituted by another amino acid, a mutagenic bFGF gene is produced by changing a codon using an oligonucleotide primer in the same manner as with cysteine.

The design of oligonucleotide primer of course varies with which amino acid is to be changed and can be accomplished readily by the skilled artisan.

The primer is hybridized to a single-stranded phage resulting from cloning of a single strand of the bFGF gene, such as M13 [Yanish-Perror, C. Vieira, and J. Messing, Gene, 33, 103–119 (1985); Messing, J., Methods in Enzymology, 101, 20–78 (1983)], fd [R. Herrman et al., Molecular and General Genetics, 177, 231 (1980)] or φ×174 [M. Smith and S. Gillam, Genetic Engineering, Plenum Press, Vol.3, pp.1–32 (1981)]. It is noted that the phage is capable of carrying either the sense chain or antisense chain of the gene. When the phage carries an antisense chain, in addition to discrepancies from the relevant codon determining a triplet which has encoded another amino acid, the primer may have discrepancies due to codon degeneracy from the sense chain region containing the codon to which mutation is to be induced. Similarly, when the phage carries a sense chain, the primer may not be complementary to the sense chain region containing the codon to which mutation is to be induced, as well as appropriate discrepancies from the triplet which pairs to the codon to be deleted. The conditions used for hybridization are described by M. Smith and S. Gillam in the above-mentioned literature. Temperature is normally between about 0° C. and 70° C., more generally, between about 10° C. and 50° C. After hybridization, the primer is elongated on the phage DNA by reaction with *Escherichia coli* DNA polymerasa I, T4 DNA polymerase, reverse transcriptase or other appropriate DNA polymerase. The resulting dsDNA is converted to a closed circular dsDNA by treatment with DNA ligase such as T4 DNA ligase. The DNA molecules containing single-strand regions can be decomposed by S1 endonuclease treatment.

The resulting mutational heteroduplex is used to transform an infectable host organism or cell. In the replication of the heteroduplex by the host, progenies are produced from both chains. Following the replication, the mutant gene is isolated from a progeny of the mutant's chain, and is inserted in an appropriate vector, which is then used to transform an appropriate host organism or cell.

The phage DNA carrying the mutational gene is then isolated, and incorporated in a plasmid.

As examples of plasmids in which DNA is incorporated, mention may be made of plasmids deriving from *Escherichia coli* such as pBR322 [Gene, 2, 95 (1977)], pBR325 [Gene, 4, 121 (1978)], pUC12 [Gene, 19, 259 (1982)] and pUC13 [Gene, 19, 259 (1982)]; and plasmids deriving from *Bacillus subtilis* such as pUB110 [Biochemical and Biophysical Research Communication, 112, 678 (1983)]; but any other plasmid can also be used, as long as it is replicated and held in the host.

As methods of incorporation in plasmid, there may be mentioned, for example, the method described in Molecular Cloning, T. Maniatis et al., Cold Spring Harbor Laboratory, p. 239 (1982), etc.

The cloned gene is ligated downstream of a promoter in a suitable vehicle (vector) for expression to obtain an expression vector.

Vectors include the above-mentioned plasmids deriving from *Escherichia coli* (e.g., pBR322, pBR325, pUC12 and pUC13), plasmids deriving from *Bacillus subtilis* (e.g., pUB110, pTP5 and pC194), plasmids deriving from yeast (e.g., pSH19 and pSH15), bacteriophages such as λ phage, and animal viruses such as retrovirus and vaccinia virus.

The said gene may have ATG as a translation initiation codon at its 5'-terminal, and may also have TAA, TGA or TAG as a translation termination codon at its 3'-terminal. For the purpose of expression of the said gene, a promoter is ligated upstream thereof. Any promoter can be used for the present invention, as long as it appropriately corresponds to the host used for the gene expression, i.e. it promotes expression in that host.

When the host for transformation is a bacterium of the genus Escherichia, trp promoter, lac promoter, rec A promoter, λPL promoter, lpp promoter, T7 promoter, etc. are appropriate; when the host is a bacterium of the genus Bacillus, SP01 promoter, SP02 promoter, penP promoter etc. are appropriate; when the host is a yeast, PH05 promoter, PGK promoter, GAP promoter, ADH promoter, etc. are appropriate. Specifically, it is preferable that the host be a bacterium of the genus Escherichia, and the promoter be trp promoter or λPL promoter or T7 promoter.

When the host is an animal cell, appropriate promoters include promoters deriving from SV40 and retrovirus promoters; specifically, promoters deriving from SV40 are preferable.

Using the vector thus constructed, which contains a recombinant DNA segment having a mutein-encoding base sequence, a transformant is produced.

As hosts, there may be mentioned, for example, bacteria of the genus Escherichia, bacteria of the genus Bacillus, yeasts, animal cells, insect cells, etc.

As examples of said bacteria of the genus Escherichia, mention may be made of *Escherichia coli* K12DH1 [Proc. Natl. Acad. Sci. USA, 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)] and MM294 [Proc. Natl. Acad. Sci. USA, 73, 4174 (1976)].

As examples of said bacteria of the genus Bacillus, mention may be made of *Bacillus subtilis* MI114 [Gene, 24, 255 (1983)] and 207–21 [Journal of Biochemistry, 95, 87 (1984)].

As examples of said yeasts, mention may be made of *Saccharomyces cerevisiae* AH22R⁻, NA 87-11A and DKD-5D.

As examples of animal cells, mention may be made of simian cell COS-7, Vero, Chinese hamster ovary cell CHO, mouse L-cell and human FL-cell.

The transformation of the above-mentioned bacteria of the genus Escherichia is carried out in accordance with, for example, the methods described in Proc. Natl. Acad. Sci. USA, 69, 2110 (1972), Gene, 17, 107 (1982), etc.

The transformation of bacteria of the genus Bacillus is carried out in accordance with, for example, the methods described in Molecular and General Genetics, 168, 111 (1979) etc.

The transformation of yeasts is carried out in accordance with, for example, the method described in Proc. Natl. Acad. Sci. USA, 75, 1929 (1978).

The transformation of animal cells is carried out in accordance with, for example, the method described in Virology, 52, 456 (1973).

A transformant harboring a vector containing a recombinant DNA having a mutein-encoding base sequence is thus obtained.

The said transformant is cultured in a medium to allow it to produce such mutein.

In culturing a transformant whose host is a bacterium of the genus Escherichia or Bacillus, liquid medium is appropriate for the cultivation, in which carbon sources, nitrogen sources, minerals, and other substances essential to the growth of the said transformant are contained. Carbon sources, there may be mentioned, for example, glucose, dextrin, soluble starch, sucrose, etc.; as nitrogen sources, there may be mentioned, for example, inorganic or organic substances such as ammonium salts, nitrates, corn steep liquor, peptone, casein, meat extract, soybean cake and potato extract; as minerals, include, for example, calcium chloride, sodium dihydrogenphosphate and magnesium chloride. Yeasts extracts, vitamins, growth accelerators, etc. may also be added.

It is desirable that the pH of medium be about 6 to 8.

An example of appropriate medium for the cultivation of bacteria of the genus Escherichia, include M9 medium containing glucose and casamino acid [Miller, Journal of Experiments in Molecular Genetics, 431–433, Cold Spring Harbor Laboratory, New York (1972)]. Chemicals such as 3β-indolylacrylic acid may be added thereto, when it is necessary to increase promoter efficiency.

When the host is a bacterium of the genus Escherichia, cultivation is normally carried out at about 15° to 43° C. for about 3 to 24 hours, and, where necessary, aeration and/or agitation are added.

When the host is a bacterium of the genus Bacillus, cultivation is normally carried out at about 30° to 40° C. for about 6 to 24 hours, and, where necessary, aeration and/or agitation are added.

A medium for the cultivation of transformants whose host is a yeast, include, for example, Burkholder's minimum medium [Bostian, K. L. et al., Proc. Natl. Acad. Sci. USA, 77, 4505 (1980)]. It is preferable that the pH of the medium be adjusted to about 5 to 8. Cultivation is normally carried out at about 20° to 35° C. for about 24 to 72 hours, and, where necessary, aeration and/or agitation are added.

Media for the cultivation of transformants whose host is an animal cell, include, for example, MEM media containing about 5 to 20% fetal bovine serum [Science, 122, 501 (1952)], DMEM medium [Virology, 8, 396 (1959)], RPMI1640 medium [Journal of the American Medical Association, 199, 519 (1967)] and 199 medium [Proceeding of the Society for the Biological Medicine, 73, 1 (1950)]. It is preferable that pH be about 6 to 8. Cultivation is normally carried out at about 30° to 40° C. for about 15 to 60 hours, and, where necessary, aeration and/or agitation are added.

The separation and purification of muteins from the above-mentioned culture can be carried out by a number of methods, for example, the following methods can be used.

In extracting mutein from cultured bacterial, fungal or animal cells, there can be employed as appropriate, for example, the method in which bacterial, fungal or animal cells, after cultivation, are collected by a known method, and suspended in a buffer solution containing a protein denaturant such as guanidine hydrochloride to elute the desired protein out of the cells, and the method in which bacterial, fungal or animal cells, after disintegration by French press, ultrasonication, lysozyme treatment and/or freezing-thawing, are subjected to centrifugation to obtain mutein. Specifically, the method using in combination lysozyme treatment and ultrasonication is preferable.

The purification of mutein from the supernatant thus obtained can be carried out by methods of separation and purification in appropriate combination well known to the skilled artisan. Examples of such well-known methods of separation and purification include methods based on solubility such as salting-out and solvent precipitation; methods based mainly on the difference in molecular weight such as dialysis, ultrafiltration, gel filtration and SDS-polyacrylamide gel electrophoresis; methods based on the difference in electric charge such as ion-exchange chromatography; methods based on specific affinity such as affinity chromatography; methods based on the difference in hydrophobicity such as reverse phase high performance liquid chromatography; and methods based on the difference in isoelectric point such as isoelectric electrophoresis.

More specifically, by subjecting the above-mentioned supernatant to ion-exchange chromatography using DEAE cellulose etc. as carriers, impurities such as nucleic acids and acid protein can be removed. For example, it is efficient to pass the supernatant through a DEAE cellulose column equilibrated with a nearly neutral buffer solution such as Tris, and collect the fraction not adsorbed to the column. By further subjecting the collected fraction to ion-exchange chromatography using as a carrier CM cellulose or the like, it is possible to adsorb mutein to the carrier, and elute the mutein with a salt solution. These eluates may be lyophilized after dialysis.

Affinity chromatography using heparin-Sepharose can be suitably applied to purifying bFGF mutein in extracts. Thus, for instance, the bFGF mutein protein can be purified by applying the above eluate to a heparin-Sepharose column equilibrated with an almost neutral buffer (e.g. Tris or phosphate buffer), washing the column thoroughly and performing elution by linear gradient constructed with NaCl or the like.

Heparin columns (e.g. Shodex AF-pak HR-894, available from Showa Denko, Japan) developed for high performance liquid chromatography are particularly efficient.

In this case, bFGF mutein can be recovered as homogeneous product in the same manner as in the case of the heparin-Sepharose column mentioned above, namely by applying the sample to a heparin column with an about neutral buffer, washing the column thoroughly and conducting elution on a linear gradient constructed with NaCl, for instance.

The thus-obtained product can be made up into a dry powder form by dialysis and lyophilization. It is desirable to preserve the product with an added carrier (e.g. serum albumin) since the adsorption of the product on the vessel wall can be prevented thereby.

Furthermore, it is preferable to add a slight amount of a reducing agent in the course of purification or preservation, in order to prevent an oxidation of the product.

Examples of the reducing agent, include β-mercaptoethanol, dithiothreitol, glutathione, and so forth.

In this way, substantially pure bFGF mutein protein can be obtained. The substantially pure bFGF mutein protein according to this invention includes products whose bFGF mutein protein content is not less than 95% (w/w) and, more preferably, products whose bFGF mutein content is not less than 98% (w/w).

The mutein thus obtained possesses at least one of the activities of fibroblast growth promoting activity, growth stimulating activity of capillary endothelial cells and angiogenic acitivity, and some of the mutein thus obtained have high stability and are low in toxicity; therefore, it can be used as a healing accelerator for burns, wounds, postoperative tissues, etc., or as a therapeutic drug based on its angiogenic action for thrombosis, arteriosclerosis, etc. It can also be used as a reagent for acceleration of cell cultivation.

Especially, a mutein wherein at least one constituent cysteine is replaced by serine is preferred, because the mutein is remarkably stable.

The mutein according to the present invention, when used as a pharmaceutical, can be safely administered parenterally or orally to warm-blooded animals (e.g., humans, mice, rats, hamsters, rabbits, dogs and cats) directly in a powder form or after preparing as a pharmaceutical composition (e.g., injection, tablets, capsules, solutions and ointments) with other pharmacologically allowable carriers, excipients or diluents.

The preparation of injection is carried out in accordance with a routine method using, for example, a physiological saline solution or an aqueous solution containing glucose and other auxiliary agents. Pharmaceutical compositions such as tablets and capsules can also be prepared in accordance with routine methods. When prepared for use as a pharmaceutical, care should be taken that aseptic conditions are used and that the resultant product is sterile, low in pyrogens and endotoxins.

The mutein according to the present invention, when used as any of the above-mentioned pharmaceuticals, is, for example, administered to the above-mentioned warm-blooded animals in an appropriate amount selected in the range of from about 1 ng/kg body weight to 100 μg/kg body weight daily, taking note of the route of administration, symptoms, etc.

The mutein according to the present invention, when used as a reagent for accelerating cell cultivation, is preferably added to the medium so that it is contained therein in an amount of about 0.01 to 10 μg per 1 liter of medium, more preferably about 0.1 to 10 μg per 1 liter of medium.

The mutein of the present invention possesses excellent fibroblast growth promoting activities, vasoendothelial cell growth promoting activities and angiogenic activities, with high stability. In addition, replacement of the constituent amino acid cysteine by another amino acid improves stability. Furthermore, a mutein of bFGF which lacks 7 to 46 amino acid residues from the carboxyl terminal does not cause an adverse effect to cells of living body. The mutein of the present invention can therefore function well as a healing promoter for burns etc., therapeutic drug for thrombosis, arteriosclerosis etc., and cell cultivation promoter.

The abbreviations for bases, amino acids, etc., used in the present specification and the drawings, are based on the abbreviations specified by the IUPAC-IUB Commission on Biochemical Nomenclature or those used commonly in relevant fields, and instances thereof are listed below. When there is a possibility of the presence of an optical isomer in amino acids, the isomer is an L-body unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
Tdr: Thymidine
EDTA: Ethylenediaminetetraacetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine In the present specification and the drawings, in numbering the human bFGF wherein Met has been added to the N-terminal of the above-mentioned amino acid sequence [II] or [III] afore-mentioned, the Met is determined as the 1st amino acid, unless otherwise noted.

The following transformants which were produced in the Reference Examples or Examples mentioned below were deposited at the Institute for Fermentation, Osaka (IFO), 17–85, Juso-honmachi 2-Chome, Yodogawa-Ku, Osaka Japan and at the Fermentation Research Institute, Agency of Industrial Science and Technology, Ministry of International Trade and Industry (FRI), 1–3 Higashi 1-Chome, Tsukuba-shi, Ibaraki-ken 305, Japan under the accession numbers on the deposit dates shown in Table 1 (The deposit dates are indicated in parentheses). As to the deposit number of FRI, FERM BP number denotes the number of deposit under the Budapest Treaty; and in case both FERM P number and FERM BP number are described, it shows that the deposit under a number of FERM P has been converted to deposit under Budapest Treaty and the transformants have been stored at FRI under the number of FERM BP.

TABLE 1

| Transformants | IFO | | FRI |
|---|---|---|---|
| E. coli K12 DHI/pTB 627 [Reference Example 1] | IFO 14494 (March 13, 1986) | FERM P-8726 (April 2, 1986) | FERM BP-1280 |
| E. coli K12 MM294/pTB 669 [Reference Example 2] | IFO 14532 (August 11, 1986) | FERM P-8918 (August 21, 1986) | FERM BP-1281 |
| E. coli DH1/pTB 739 [Example 2] | IFO 14575 (February 18, 1987) | FERM P-9216 (February 25, 1987) | FERM BP-1641 |
| E. coli DH1/pTB 742 [Example 3] | IFO 14584 (March 24, 1987) | FERM P-9307 (March 30, 1987) | FERM BP-1642 |
| E. coli DH1/pTB 743 [Example 4] | IFO 14585 (March 24, 1987) | FERM P-9308 (March 30, 1987) | FERM BP-1643 |
| E. coli DH1/pTB 744 [Example 5] | IFO 14586 (March 24, 1987) | FERM P-9309 (March 30, 1987) | FERM BP-1644 |
| E. coli MM294/pTB 762 [Example 7] | IFO 14613 (May 27, 1987) | FERM P-9409 (June 11, 1987) | FERM BP-1645 |
| E. coli MM294/pTB 764 [Example 9] | IFO 14614 (May 27, 1987) | FERM P-9410 (June 11, 1987) | FERM BP-1646 |
| E. coli MM294/pTB 765 [Example 11] | IFO 14615 (May 27, 1987) | FERM P-9411 (June 11, 1987) | FERM BP-1647 |
| E. coli MM294/pTB 795 [Example 34] | IFO 14700 (January 14, 1988) | | FERM BP-1660 (January 20, 1988) |
| E. coli MM294/pTB 796 [Example 35] | IFO 14701 (January 14, 1988) | | FERM BP-1661 (January 20, 1988) |
| E. coli MM294/pTB 797 [Example 36] | IFO 14702 (January 14, 1988) | | FERM BP-1662 (January 20, 1988) |
| E. coli MM 294/pTB893 (Example 43) | IFO 14772 (August 12, 1988) | FERM BP-2009 (August 22, 1988) | |
| E. coli MM294/pTB898 (Example 43) | IFO 14773 (August 12, 1988) | FERM BP-2010 (August 22, 1988) | |
| E. Coli MM294/pTB899 (Example 43) | IFO 14774 (August 12, 1988) | FERM BP-2011 (August 22, 1988) | |
| E. coli MM294/pTB922 (Example 44) | IFO 14775 (August 12, 1988) | FERM BP-2012 (August 22, ,1988) | |
| E. coli MM294/pTB923 (Example 45) | IFO 14776 (August 12, 1988) | FERM BP-2013 (August 22, 1988) | |
| E. coli BL 21 (DE3) pLysS/pTB956 (Example 47) | IFO 14805 (December 16, 1988) | FERM BP-2202 (December 23, 1988) | |
| E. coli BL 21 (DE3) pLysS/pTB958 (Example 48) | IFO 14806 (December 16, 1988) | FERM BP-2203 (December 23, 1988) | |

The following hybridomas which were produced in the Example 35(3)(d) mentioned below were deposited at IFO since Aug. 17, 1987 under the accession numbers indicated below.

Mouse HbF 52 cell: IFO 50143

Mouse HbF 78 cell: IFO 50144

BRIEF DESCRIPTION OF THE DRAWINGS

FIG. 1 shows the base sequence which encodes human bFGF and the amino acid sequence deduced therefrom.

FIG. 2 shows the synthetic oligomers used as primers to mutate Cys-encoding codons to Ser-encoding codons.

FIG. 3 shows the base sequence which encodes the human bFGF mutein CS1, carried by the plasmid pTB739 obtained in Example 2, and the amino acid sequence of the human bFGF mutein CS1, encoded thereby. The mutated bases are underlined, and the region containing the converted amino acid is surrounded by the square.

FIG. 4 shows the base sequence which encodes the human bFGF mutein CS2, carried by the plasmid pTB742 obtained in Example 3, and the amino acid sequence of the human bFGF mutein CS2, encoded thereby. The mutated bases are underlined, and the region containing the converted amino acid is surrounded by the square.

FIG. 5 shows the base sequence which encodes the human bFGF mutein CS3, carried by the plasmid pTB743 obtained in Example 4, and the amino acid sequence of the human bFGF mutein CS3, encoded thereby. The mutated bases are underlined, and the region containing the converted amino acid is surrounded by the square.

FIG. 6 shows the base sequence which encodes the human bFGF mutein CS4, carried by the plasmid pTB744 obtained in Example 5, and the amino acid sequence of the human bFGF mutein CS4, encoded thereby. The mutated bases are underlined, and the region containing the converted amino acid is surrounded by the square.

FIG. 11 shows the base sequence which encodes the human bFGF mutein CS23, carried by the plasmid pTB762 obtained in Example 7, and the amino acid sequence of the human bFGF mutein CS23, encoded thereby. The mutated bases are underlined, and the regions containing either of the converted amino acids are surrounded by the squares.

FIG. 13 shows the base sequence which encodes the human bFGF mutein CS123, carried by the plasmid pTB764 obtained in Example 9, and the amino acid sequence of the human bFGF mutein CS123 encoded thereby. The mutated bases are underlined, and the regions containing any of the converted amino acids are surrounded by the squares.

FIG. 15 shows the base sequence which encodes the human bFGF mutein CS1234, carried by the plasmid pTB765 obtained in Example 11 and the amino acid sequence of the human bFGF mutein CS1234, coded thereby. The mutated bases are underlined, and the regions containing any of the converted amino acids are surrounded by the squares.

FIG. 17 shows the base sequence which encodes the human bFGF mutein CS12, carried by the plasmid pTB776 obtained in Example 15, and the amino acid sequence of the human bFGF mutein CS12, encoded thereby. The mutated bases are underlined, and the regions containing either of the converted amino acids are surrounded by the squares.

FIG. 19 shows the base sequence which encodes the human bFGF mutein CS24, carried by the plasmid pTB778 obtained in Example 16, and the amino acid sequence of the human bFGF mutein CS24, encoded thereby. The mutated bases are underlined, and the regions containing either of the converted amino acids are surrounded by the squares.

FIG. 21 shows the base sequence which encodes the human bFGF mutein CS13, carried by the plasmid pTB779 obtained in Example 17, and the amino acid sequence of the human bFGF mutein CS13, encoded thereby. The mutated bases are underlined, and the regions containing either of the converted amino acids are surrounded by the squares.

FIG. 23 shows the base sequence which encodes the human bFGF mutein CS14, carried by the plasmid pTB763 obtained in Example 18, and the amino acid sequence of the human bFGF mutein CS14, encoded thereby. The mutated bases are underlined, and the regions containing either of the converted amino acids are surrounded by the squares.

FIG. 25 shows the base sequence which encodes the human bFGF mutein CS34, carried by the plasmid pTB777 obtained in Example 19, and the amino acid sequence of the human bFGF mutein CS34, encoded thereby. The mutated bases are underlined, and the regions containing either of the converted amino acids are surrounded by the squares.

FIG. 27 shows the base sequence which encodes the human bFGF mutein CS234, carried by the plasmid pTB782 obtained in Example 20, and the amino acid sequence of the human bFGF mutein CS234, encoded thereby. The mutated bases are underlined, and the regions containing any of the converted amino acids are surrounded by the squares.

FIG. 29 shows the base sequence which encodes the human bFGF mutein CS124, carried by the plasmid pTB780 obtained in Example 21, and the amino acid sequence of the human bFGF mutein CS124, encoded thereby. The mutated bases are underlined, and the regions containing any of the converted amino acids are surrounded by the squares.

FIG. 31 shows the base sequence which encodes the human bFGF mutein CS134, carried by the plasmid pTB781 obtained in Example 22, and the amino acid sequence of the human bFGF mutein CS134, encoded thereby. The mutated bases are underlined, and the regions containing any of the converted amino acids are surrounded by the squares.

FIG. 38 shows the synthetic oligomers used as primers to prepare mutein-encoding DNAs.

FIG. 39 shows the base sequence of the phage M13-PN10 obtained in Example 27 and the amino acid sequence of mutein TM910 encoded thereby, the mutein TM910 being obtained in Example 32.

FIG. 40 shows the base sequence of the phage M13-PN14 obtained in Example 27 and the amino acid sequence of mutein N14 encoded thereby, the mutein N14 being obtained in Example 34.

FIG. 41 shows the base sequence of the phage M13-PC86 obtained in Example 27 and the amino acid sequence of mutein C86 encoded thereby, the mutein C86 being obtained in Example 35.

FIG. 42 shows the base sequence of the phage M13-PDN42 obtained in Example 27 and the amino acid sequence of mutein DN42 encoded thereby, the mutein DN42 being obtained in Example 36.

FIG. 43 shows the base sequence of the phage M13-PRQ45 obtained in Example 27 and the amino acid sequence of mutein RQ45 encoded thereby, the mutein RQ45 being obtained in Example 37.

FIG. 44 shows the base sequence of the phage M13-PNR42 obtained in Example 28 and the amino acid sequence of mutein NR42 encoded thereby, the mutein NR42 being obtained in Example 38.

FIG. 48 shows the base sequence which encodes the human bFGF mutein N10, carried by the plasmid pTB852 obtained in Example 33, and the amino acid sequence of the mutein N10 encoded thereby, the mutein N10 being ontained in Example 33. The mutated bases are underlined.

FIG. 54 shows the base sequence which encodes the human bFGF mutein FINT, carried by the plasmid pTB853 obtained in Example 39, and the amino acid sequence of the mutein FINT encoded thereby, the mutein FINT being obtained in Example 39. The mutated bases are underlined.

FIG. 57 shows the base sequence which encodes the human bFGF mutein N41 carried by the plasmid pTB855 obtained in Example 40, and the amino acid sequence of the mutein N41 encoded thereby, the mutein N41 being obtained in Example 40. The mutated bases are underlined.

FIG. 59 shows the base sequence which encodes the human bFGF mutein C129 carried by the plasmid pTB856 obtained in Example 41, and the amino acid sequence of the mutein C129 encoded thereby, the mutein C129 being obtained in Example 41. The mutated bases are underlined.

FIG. 62 shows the base sequence which encodes rhbFGF mutein CS102, carried by plasmids pTB905 and 893 obtained in Example 43, and the amino acid sequence of rhbFGF mutein C102, encoded thereby.

FIG. 63 shows the base sequence which encodes rhbFGF mutein C105, carried by plasmids pTB906 and 894 obtained in Example 43, and the amino acid sequence of rhbFGF mutein C105, encoded thereby.

FIG. 64 shows the base sequence which encodes rhbFGF mutein C114, carried by plasmids pTB907 and 895 obtained in Example 43, and the amino acid sequence of rhbFGF mutein C114, encoded thereby.

FIG. 65 shows the base sequence which encodes rhbFGF mutein C118, carried by plasmids pTB908 and 896 obtained in Example 43, and the amino acid sequence of rhbFGF mutein C118, encoded thereby.

FIG. 66 shows the base sequence which encodes rhbFGF mutein C123, carried by plasmids pTB909 and 897 obtained in Example 43, and the amino acid sequence of rhbFGF mutein C123, encoded thereby.

FIG. 67 shows the base sequence which encodes rhbFGF mutein C129, carried by plasmids pTB910 and 898 obtained in Example 43, and the amino acid sequence of rhbFGF mutein C129, encoded thereby.

FIG. 68 shows the base sequence which encodes rhbFGF mutein C137, carried by plasmids pTB911 and 899 obtained in Example 43, and the amino acid sequence of rhbFGF mutein C 137, encoded thereby.

FIG. 71 shows the base sequence which encodes rhbFGF mutein CS23C129, carried by plasmid pTB922 obtained in Example 44, and the amino acid sequence of rhbFGF mutein CS23C129, encoded thereby. The mutated bases are underlined, and each region containing a converted amino acid is surrounded by a square.

FIG. 72 shows the base sequence which encodes rhbFGF mutein CS23C137, carried by plasmid pTB923 obtained in Example 45, and the amino acid sequence of rhbFGF mutein CS23C137, encoded thereby. The mutated bases are underlined, and each region containing a converted amino acid is surrounded by a square.

REFERENCE EXAMPLE 1

Figure 7:
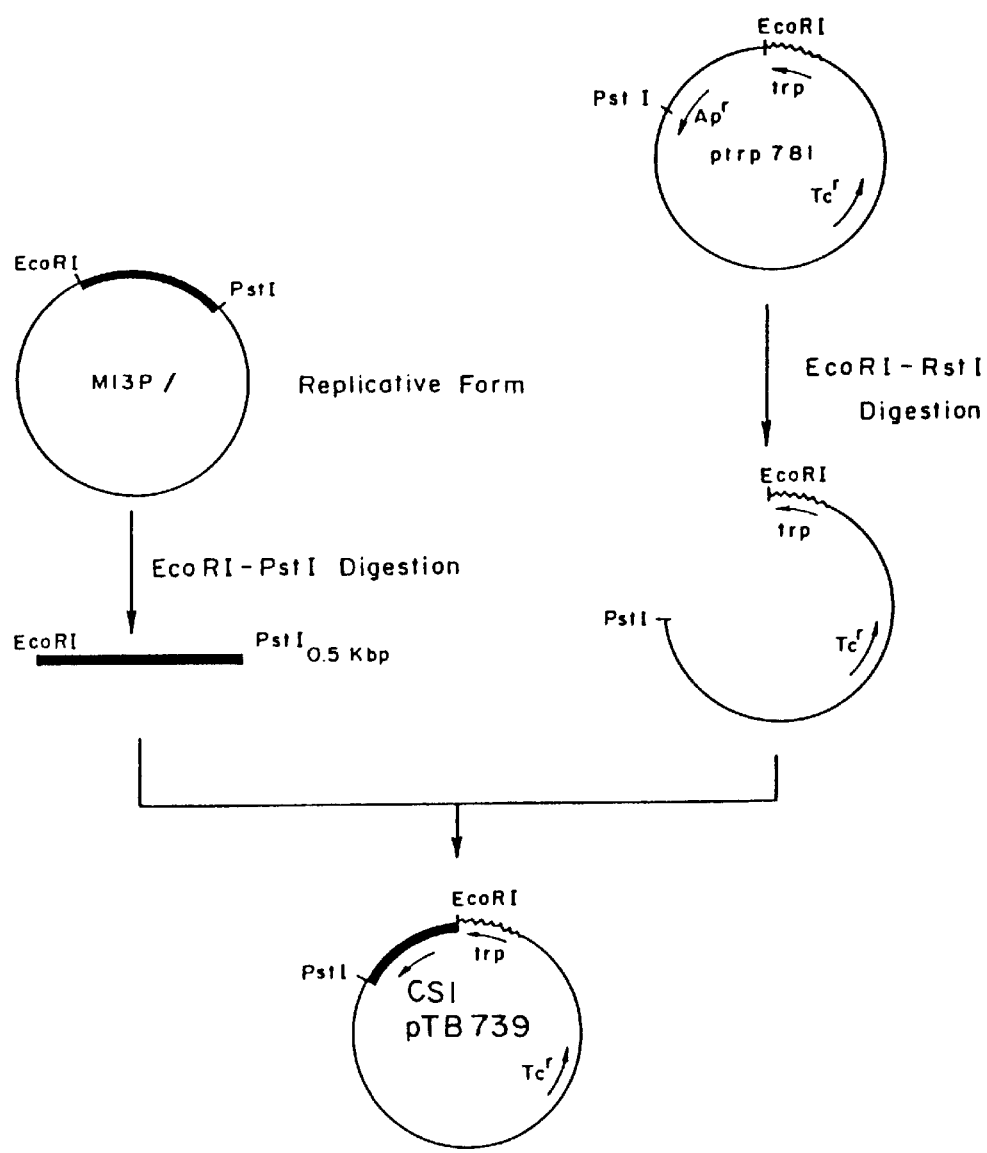
FIG. 7 shows the construction scheme of the plasmid pTB739 in Example 2 (1).

(Construction of Plasmid Containing Gene Encoding Human bFGF)

(1) Isolation of cDNA-Containing Plasmid:

A cDNA whose host is *Escherichia coli* x1776 and which was prepared by incorporating a primary culture cell mRNA deriving from human prepuce in pCD vector [refer to Okayama et al., Molecular and Cellular Biology, 3, 280 (1983)] was supplied by Dr. Okayama at the National Institute of Child Health and Human Development, Bethesda, USA. From this DNA was extracted a plasmid DNA by the alkali method [Birnboim, H. C. and Doly, J., Nucleic Acids Research, 1, 1513 (1979)], and this DNA was infected with *Escherichia coli* DH1 to produce about 2×10$^6$ clones of a cDNA library whose host is *Escherichia coli* DH1.

Said cDNA library using *Escherichia coli* DH1 was spread over 10 nitrocellulose filters (Millipore Inc., U.S.A. HATF filters) in an amount of about 5×10$^4$ clones/filter, whereafter a total of 20 replica filters in pairs were prepared using the above 10 filters as the master filters. *Escherichia coli* cells on the replica filters were lysed with a 0.5N NaOH solution, and the exposed denatured plasmid DNA was immobilized to the filters [Grunstein, M. and Hogness, D. S., Proc. Natl. Acad. Sci. USA, 72, 3961 (1975)].

Separately, based on the amino acid Nos. 13 to 20 (Pro-Pro-Gly-His-Phe-Lys-Asp-Pro) and amino acid Nos. 89 to 96 (Thr-Asp-Glu-Cys-Phe-Phe-Phe-Glu) on the amino acid sequence of bovine basic fibroblast growth factor as reported by F. Esch et al. [Proc. Natl. Acad. Sci. USA, 82, 6507 (1985)], the base sequences corresponding to these amino acid sequences were chemically synthesized. (For some codons, the 3rd letter was fixed arbitrarily. 5'GG A/G TC T/C TT A/G AA A/G TGGCCAGGAGG and 5'TC A/G AA A/G AA A/G AA A/G CA T/C TCGTCGGT, respectively. The underlined letters represent the fixed bases). For each of these oligonucleotides, reaction was carried out at 37° C. for 1 hour in 50 µl of a reaction liquid using T4 polynucleotide kinase (produced by Takara Shuzo Co., Ltd., Japan) [oligonucleotide 0.1 µg, 50 mM Tris-HCl pH 8.0, 0.10 mM MgCl$_2$, 10 mM mercaptoethanol, 50 µCi γ-$^{32}$P ATP (>5000 Ci/mmole), 3 units of T4 polynucleotide kinase] to label the 5'-terminal of the oligonucleotides with $^{32}$P.

Using as probes the 2 oligonucleotides labeled in the above method, these were independently associated to a replica filter to which the DNA had been immobilized. Association reaction was carried out at 35° C. for 16 hours in a solution of 5×SSPE [180 mM NaCl, 10 mM $NaH_2PO_4$, 1 mM EDTA (pH 7.4)], 5×Denhardt's solution, 0.1% SDS and 100 μg/ml denatured salmon sperm DNA, containing 10 μCi of the probe. After the reaction, the filter was washed with a 0.1% SDS solution of 5×SSC [0.15M NaCl, 0.015M sodium citrate] at room temperature for 30 minutes 3 times, and then at 45° C. for 30 minutes 2 times [T. Maniatis et al., Molecular Cloning, Cold Spring Harbor Laboratory, p. 309 (1982)].

Radioautograms were taken from the washed filters, and strains responding to both probes were searched for by overlapping the 2 radioautograms from each pair of replica filters. By this method, 1 strain responding to both probes [*Escherichia coli* K12 DH1/pTB627 (IFO 14494, FERM BP-1280)] was obtained from $5×10^5$ clones.

(2) From the strain obtained in (1) above [*Escherichia coli* K12 DH1/pTB627 (IFO 14494, FERM BP-1280)] was extracted and purified a plasmid DNA (pTB627) by the alkali method [Nucleic Acids Research, 1, 1513 (1979)].

REFERENCE EXAMPLE 2

(Expression in *Escherichia coli* of Gene which Encodes Human bFGF)

(1) Construction of the Plasmid pTB669 for Human bFGF Expression:

The plasmid pTB627 containing a human bFGF cDNA obtained in Reference Example 1 (2) above was cleaved using the restriction enzymes AvaI and BalI to obtain a 0.44 kb DNA fragment containing the region coding for human bFGF. To the BalI cleavage site (blunt end) of this DNA fragment was ligated the BglII linker pCAGATCTG using T4 DNA ligase, and a 0.44 kb AvaI-BglII DNA fragment was separated. To this 0.44 kb AvaI-BglII DNA fragment T4 DNA ligase was reacted to ligate together the BglII cleavage sites, and this was followed by DNA polymerase (Klenow fragment) reaction in the presence of dXTP to blunt the AvaI cleavage site. To this DNA fragment were ligated the synthetic oligonucleotides 5'AATTCTATGCCAGCATTGC3' and 5'GCAATGCTGGCATAG3' after phosphorylation, using T4 DNA ligase, and this was followed by cleavage using EcoRI-BglII to prepare an about 0.46 kb DNA fragment. Separately, the DNA of plasmid ptrp781 [Kurokawa, T. et al., Nucleic Acids Research, 11, 3077–3085 (1983)], which has trp promoter, was cleaved using PstI, and was blunted by T4 DNA polymerase reaction. After ligation of the BglII linker pCAGATCTG to the blunt end by T4 DNA ligase reaction, cleavage using EcoRI-BglII was carried out to separate an about 3.2 kb DNA fragment containing trp promoter, the tetracycline resistance gene and a plasmid replication initiation site. The above-mentioned 0.46 kb EcoRI-BglII DNA fragment containing the gene region encoding human bFGF and this 3.2 kb DNA fragment were ligated together by T4 DNA ligase reaction to construct the plasmid pTB669 for human bFGF expression.

Using this plasmid pTB669, *Escherichia coli* DH1 was transformed, whereby *Escherichia coli* DH1/pTB669, which harbors the plasmid pTB669, was obtained.

In addition, using pTB669, *Escherichia coli* K12 MM294 or C600 was transformed in the same manner as above, whereby *Escherichia coli* K12 MM294/pTB669 (IFO 14532, FERM BP-1281) and *E. coli* C600/pTB669 were respectively obtained.

(2) Preparation of Bacterial Cell Extracts:

Each of the above-mentioned transformants were cultured in an M9 medium containing 1% glucose, 0.4% casamino acid and 8 μg/ml tetracycline, and, when Klett value became about 200, 3β-indolylacrylic acid was added to a concentration of 25 μg/ml, and this was followed by 4 more hours of cultivation. After cultivation, bacterial cells were collected, and were suspended in a 10% sucrose solution containing a ½₀ amount of 20 mM Tris-HCl (pH 7.6). To this suspension were added phenylmethylsulfonyl fluoride (PMSF) to 1 mM, EDTA to 10 mM, NaCl to 0.1M, spermidine hydrochloride to 10 mM and lysozyme to 100 μg/ml (every figure shows the final concentration), and the mixture was left at 0° C. for 45 minutes, after which it was subjected to ultrasonication for 30 seconds. This solution was centrifuged at 18000 rpm (Sorval centrifuge, SS34 rotor) for 30 minutes to give a supernatant, which was used as a bacterial cell extract.

(3) Human bFGF Activity of Bacterial Cell Extracts:

Human bFGF activities are indicated by the weights of the standard sample of purified bovine brain FGF (produced by Takara Shuzo Co., Ltd.) in amounts equivalent to those of bacterial cell extracts in activity in growth promoting action on BALB/c3T3 cells.

Mouse BALB/c3T3 cells, in an amount of $2×10^3$ cells per well, were inoculated to a DMEM medium containing 5% calf serum on a Nunc 96-well microtiter plate (flat base) with each well containing 0.2 ml of the medium, and were cultured. Next day the medium was replaced with a DMEM medium containing 0.5% calf serum. After 3 days of cultivation, 10 μl of a bacterial cell extract, previously serially diluted in 5-fold steps with a DME medium containing 0.5% BSA, was added to each well, and was cultured. 20 hours later, 2 μl of $^3$H-Tdr (5 Ci/mmol, 0.5 mCi/ml RCC Amersham, UK) was added to each well. 6 hours later, cells were stripped by treatment with a phosphate-buffered solution (PBS) containing 0.2% trypsin-0.02% EDTA, and the cells were harvested onto a glass filter by means of a Titertech cell harvester, whereafter the amount of $^3$H-Tdr taken in the cells was determined using a scintillation counter. Using the same procedure, determinations were made of the activities of bovine brain FGF samples (produced by Takara Shuzo) of known weight. From the working curve thus obtained, calculations were made of the amounts of human bFGF in the bacterial cell extract samples. The results are shown in Table 2.

For control, the human bFGF productivity of the transformant *E. coli* DH1/ptrp781 obtained by transformation of *Escherichia coli* DH1 using the plasmid ptrp781 was determined.

TABLE 2

| Transformant | Human bFGF Productivities |
| --- | --- |
| | Human bFGF Productivity (per liter of culture medium) |
| *E. coli* DH1/pTB669 | 2.95 mg |
| *E. coli* MM294/pTB669 | 23.15 |
| *E. coli* C600/pTB669 | 8.15 |
| *E. coli* DH1/ptrp781 | <0.0005 |

EXAMPLE 1

(Production of Recombinant DNAs Containing Mutein-Encoding Base Sequence)

(1) Cloning of M13 Vector of Human bFGF Gene:

The plasmid pTB669 obtained in Reference Example 2 was digested with the restriction enzymes EcoRI and BamHI. The phage vector M13mp8 [J. Messing, Methods in Enzymology, 101, 20–78 (1983)] replicative-form (RF) DNA was digested with the restriction enzymes EcoRI and BamHI, and was mixed with the human bFGF DNA fragment deriving from the digested pTB669. The mixture was then ligated together by means of T4 DNA ligase; the ligated DNA was transformed into an infectable cell of the strain *Escherichia coli* JM105; the resulting transformant was inoculated onto a plate using Xga1 as an indicator [J. Messing et al., Nucleic Acids Research, 9, 309–321 (1981)]; the plaque containing the recombinant phage (white plaque) was picked up; the base sequence of the recombinated region was determined by the dideoxynucleotide synthetic chain termination method [J. Messing et al., Nucleic Acids Research, 9, 309 (1981)], whereby it was confirmed that human bFGF DNA had been accurately inserted.

From this M13-PO clone was purified a single-stranded phage DNA, which was then used as a template for site-directed mutagenesis using a synthetic oligonucleotide.

(2) Site-Specific Mutagenesis:

In the presence of 0.1 mM adenosine triphosphate (ATP), 50 mM Tris (hydroxymethyl)aminomethane hydrochloride (Tris-HCl, pH 8.0), 10 mM MgCl$_2$, 5 mM dithiothreitol (DTT) and 9 units of T4 kinase, in a total amount of 50 μl, 40 picomoles of the synthetic oligonucleotide:

5'>CGT TCT TGC TGT AGA GCC GCT<3'

[primer for changing Cys 26 to Ser (the recognition sequence for the restriction enzyme RsaI disappears.) (see FIG. 2)] was treated with T4 kinase at 37° C. for 1 hour. This kinase-treated primer (12 picomoles) was heated at 67° C. for 5 minutes, and at 42° C. for 25 minutes, in 50 μl of a mixture containing 50 mM NaCl, 1.0 mM Tris-HCl (pH 8.0), 10 mM MgCl$_2$ and 10 mM β-mercaptoethanol, whereby the primer was hybridized to 5 μg of the single-stranded (ss) M13-PO DNA. The annealed mixture was then cooled on ice, and it was added to 50 μl of a reaction mixture containing 0.5 mM deoxynucleotide triphosphate (dNTP), 80 mM Tris-HCl (pH 7.4), 8 mM MgCl$_2$, 100 mM NaCl, 9 units of DNA plymerase I Klenow fragment, 0.5 mM ATP and 2 units of T4 DNA ligase, and reaction was carried out at 37° C. for 3 hours, and at 25° C. for 2 hours, whereafter the reaction was stopped by adding 2 μl of 0.2 mM EDTA. The reaction product was used to transform infectable JM 105 cells; the transformant cells thus obtained were allowed to grow overnight, whereafter an ssDNA was isolated from the culture medium supernatant. Using this ssDNA as a template for the 2nd cycle of primer elongation, gel-purified RF-type DNA was transformed into infectable JM 105 cells; the resulting transformant cells were spread over an agar plate, and were cultured overnight to obtain phage plaques.

(3) Site-Directed Mutagenesis:

The procedure of the above term(2) was repeated but the synthetic oligonucleotide primer used was:

5'>AAC GAT TAG CGC TCA CTC C<3' which so changes the cysteine-70-encoding codon that the codon encodes serine. (A recognition sequence of the restriction enzyme HaeII was produced). (See FIG. 2).

(4) Site-Directed Mutagenesis:

The procedure of the above term (2) was repeated but the synthetic oligonucleotide primer used was:

5'>GTA ACA GAC TTA GAA GCT AGT<3' which so changes the cysteine-88-encoding codon that the codon encodes serine. (A recognition sequence for the restriction enzyme AluI was produced). (See FIG. 2).

(5) Site-Directed Mutagenesis:

The procedure of the above term (2) was repeated but the synthetic oligonucleotide primer used was:

5'>TCG AAG AAG AAA GAC TCA TCC<3' which so changes the cysteine-93-encoding codon that the codon encodes serine. (A recognition sequence for the restriction enzyme HinfI was produced). (See FIG. 2).

(6) Screening and Identification of Plaques Made Mutagenic:

Plates containing mutated M13-PO plaques [above term (1)] and 2 plates containing unmutated M13-PO phage plaques were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl having a pH-value of 7.5 and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with $10^5$ cpm/ml of an oligonucleotide primer. The filters were each washed in a buffer solution for washing containing 0.1% SDS and a reduced amount of SSC at 50° C. for 30 minutes. The filters were then first washed with a buffer solution containing 2×SSC; the control filters, which contained unmutated M13-PO plaques, were examined for radioactivity using a Geiger counter. While stepwise reducing SSC concentration, the control filters were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-PO plaques and 100 unmutated control plaques using a kinase-treated oligonucleotide probe. None of the control plaques hybridized to the probe, while 3 to 10 of the mutated M13-PO plaques hybridized to the probe.

One of the mutated M13-PO plaques was taken, and was inoculated to a JM105 culture medium. From the supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the TGC (Cys-26) codon had been changed to a TCT (Ser) codon; the TGT (Cys-70) codon, to an AGC (Ser) codon; the TGT (Cys-88) codon, to a TCT (Ser) codon; and the TGT (Cys-93) codon, to a TCT (Ser) codon.

Of the mutated M13-PO phages, the phage in which the codon Cys-26 had become a Ser-encoding codon was named M13-P1; the phage in which the codon Cys-70 had become a Ser-encoding codon, M13-P2; the phage in which the codon Cys-88, M13-P3; and the phage in which the codon Cys-93 had become a Ser-encoding codon, M13-P4.

EXAMPLE 2

(Expression in *Escherichia coli* of Gene which Encodes Human bFGF Mutein)

(1) Construction of the Plasmid pTB739 for Human bFGF Mutein Expression:

The M13-P1 replicative form (RF) obtained in Example 1 above was cleaved using the restriction enzymes EcoRI and PstI to obtain about 0.5 kb DNA fragment containing the region encoding human bFGF mutein.

Separately, the plasmid ptrp781 [Kurokawa, T. et al., Nucleic Acids Research, 11, 3077–3085 (1983)] DNA containing a trp promoter was cleaved using EcoRI-PstI to separate an about 3.2 kb DNA fragment containing a trp promoter, a tetracycline resistance gene and a plasmid replication initiation site. The above-mentioned 0.5 kb EcoRI-PstI DNA fragment containing the gene region encoding human bFGF mutein and this 3.2 kb DNA fragment were ligated together by T4 DNA ligase reaction to construct the plasmid pTB739 for human bFGF mutein expression (FIG. 7).

Using this plasmid pTB739, *Escherichia coli* DH1 was transformed, whereby the strain *Escherichia coli* DH1/pTB739 (IFO 14575, FERM BP-1641) was obtained, which harbors the plasmid pTB739 containing the mutein-encoding gene shown in FIG. 3.

(2) Preparation of Bacterial Cell Extract:

The above-mentioned transformant was cultured in an M9 medium containing 1% glucose, 0.4% casamino acid and 8 μg/ml tetracycline, and, when Klett value became about 200, 3β-indolylacrylic acid was added to a concentration of 25 μg/ml, and this was followed by cultivation for 4 more hours. After cultivation, bacterial cells were collected, and were suspended in a 10% sucrose solution containing a 1/20 amount of 20 mM Tris-HCl (pH 7.6). To this suspension were added phenylmethylsulfonyl fluoride (PMSF) to 1 mM, EDTA to 10 mM, NaCl to 0.1M, spermidine hydrochloride to 10 mM and lysozyme to 100 μg/ml (every figure shows the final concentration), and the mixture was left at 0° C. for 45 minutes, after which it was subjected to ultrasonication for 30 seconds. This solution was centrifuged at 18,000 rpm (Sorval centrifuge, SS34 rotor) for 30 minutes to give a supernatant, which was then used as a bacterial cell extract.

(3) Human bFGF Activity of the Bacterial Cell Extract:

Mouse BALB/c3T3 cells, in an amount of $2 \times 10^3$ cells per well, were inoculated to a DMEM medium containing 5% calf serum on Nunc 96-well microtiter plate (flat base) with each well containing 0.2 ml of the medium, and were cultured. Next day the medium was replaced with a DMEM medium containing 0.5% calf serum. After 3 days of cultivation, 10 μl of the bacterial cell extract, previously serially diluted in 5-fold steps with a DME medium containing 0.5% BSA, was added to each well, and was cultured. 20 hours later, 2 μl of $^3$H-Tdr (5 Ci/mmol, 0.5 mCi/ml RCC Amersham) was added to each well. 6 hours later, cells were stripped by treatment with a phosphate-buffered solution (PBS) containing 0.2% trypsin-0.02% EDTA, and the cells were harvested onto a glass filter by means of a Titertech cell harvester, whereafter the amount of $^3$H-Tdr taken in the cells was determined using a scintillation counter.

The bacterial cell extract from *E. coli* DH1/pTB739 thereby tested exhibited FGF activity.

The mutein CS1, in which Cys at the 26-position of human bFGF had been replaced by Ser, was thus obtained.

EXAMPLE 3

(Expression in *Escherichia coli* of Gene Encoding Human bFGF Mutein)

(1) Construction of the Plasmid pTB742 for Human bFGF Mutein Expression:

The M13-P2 replicative form (RF) obtained in Example 1 above was cleaved using the restriction enzymes EcoRI and PstI to obtain an about 0.5 kb DNA fragment containing a region which encodes a human bFGF mutein.

Figure 8:
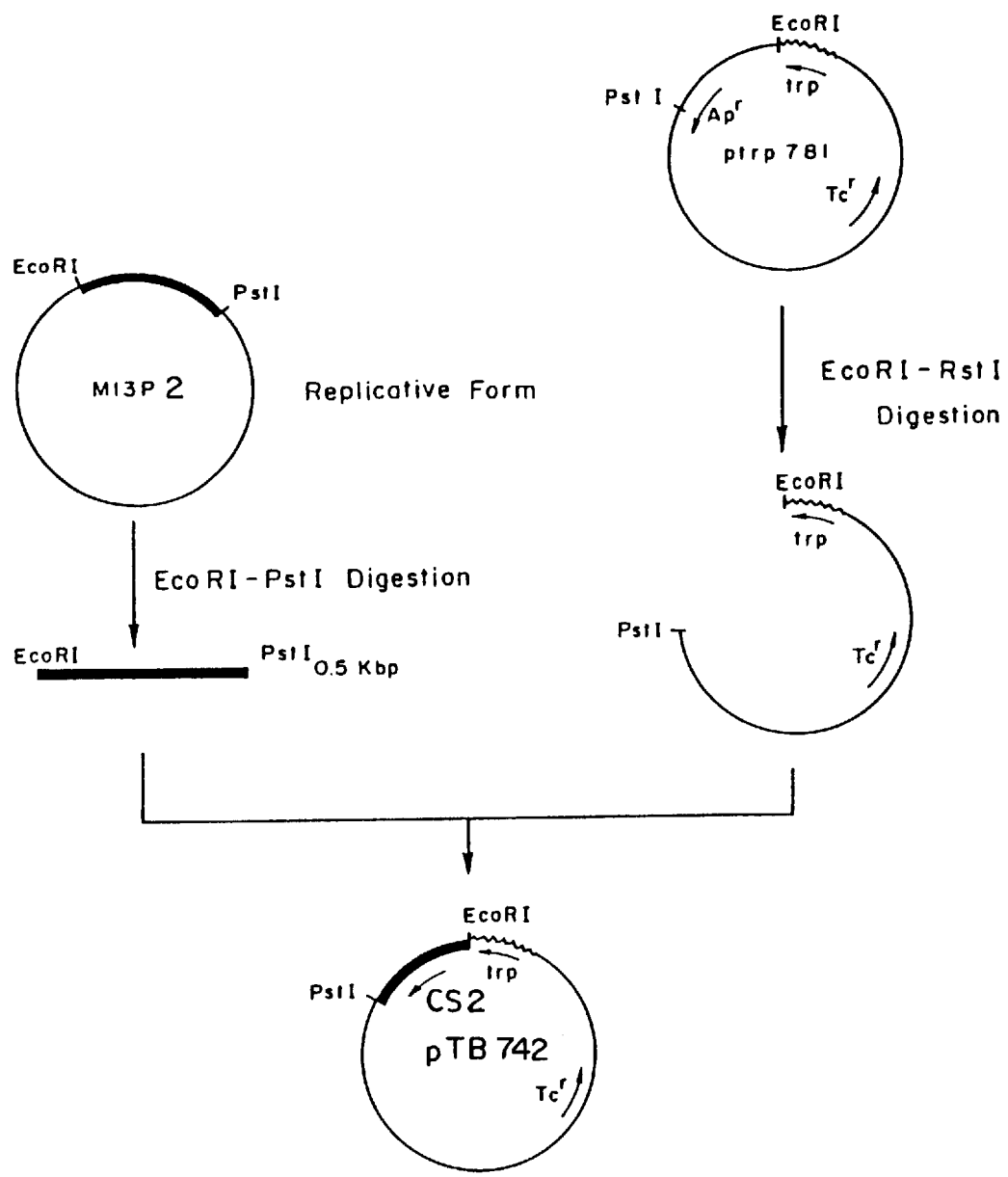
FIG. 8 shows the construction scheme of the plasmid pTB742 in Example 3 (1).

Separately, a plasmid ptrp781 DNA containing a trp promoter was cleaved using EcoRI-PstI to separate an about 3.2 kb DNA fragment containing a trp promoter, a tetracycline resistance gene and a plasmid replication initiation site. This 3.2 kb DNA fragment and the above-mentioned 0.5 kb EcoRI-PstI DNA fragment containing a gene region encoding a human bFGF mutein were ligated together by T4 DNA ligase reaction to construct the plasmid pTB742 for the expression of a human bFGF mutein (FIG. 8).

Using this plasmid pTB742, *Escherichia coli* DH1 was transformed, whereby the strain *Escherichia coli* DH1/pTB742 (IFO 14584, FERM BP-1642) was obtained, which harbors the plasmid pTB742 containing the mutein-encoding gene shown in FIG. 4.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity on the bacterial cell extract obtained in (2) above, by the method described in Example 2 (3).

The bacterial cell extract of *E. coli* DH1/pTB742 thereby tested exhibited FGF activity.

The mutein CS2, in which Cys at the 70-position of human bFGF had been replaced by Ser, was thus obtained.

EXAMPLE 4

(Expression in *Escherichia coli* of Gene Encoding Human bFGF Mutein)

(1) Construction of the Plasmid pTB743 for Human bFGF Mutein Expression:

The M13-P3 replicative form (RF) obtained in Example 1 above was cleaved using the restriction enzymes EcoRI and PstI to obtain an about 0.5 kb DNA fragment containing a region which encodes a human bFGF mutein.

Figure 9:
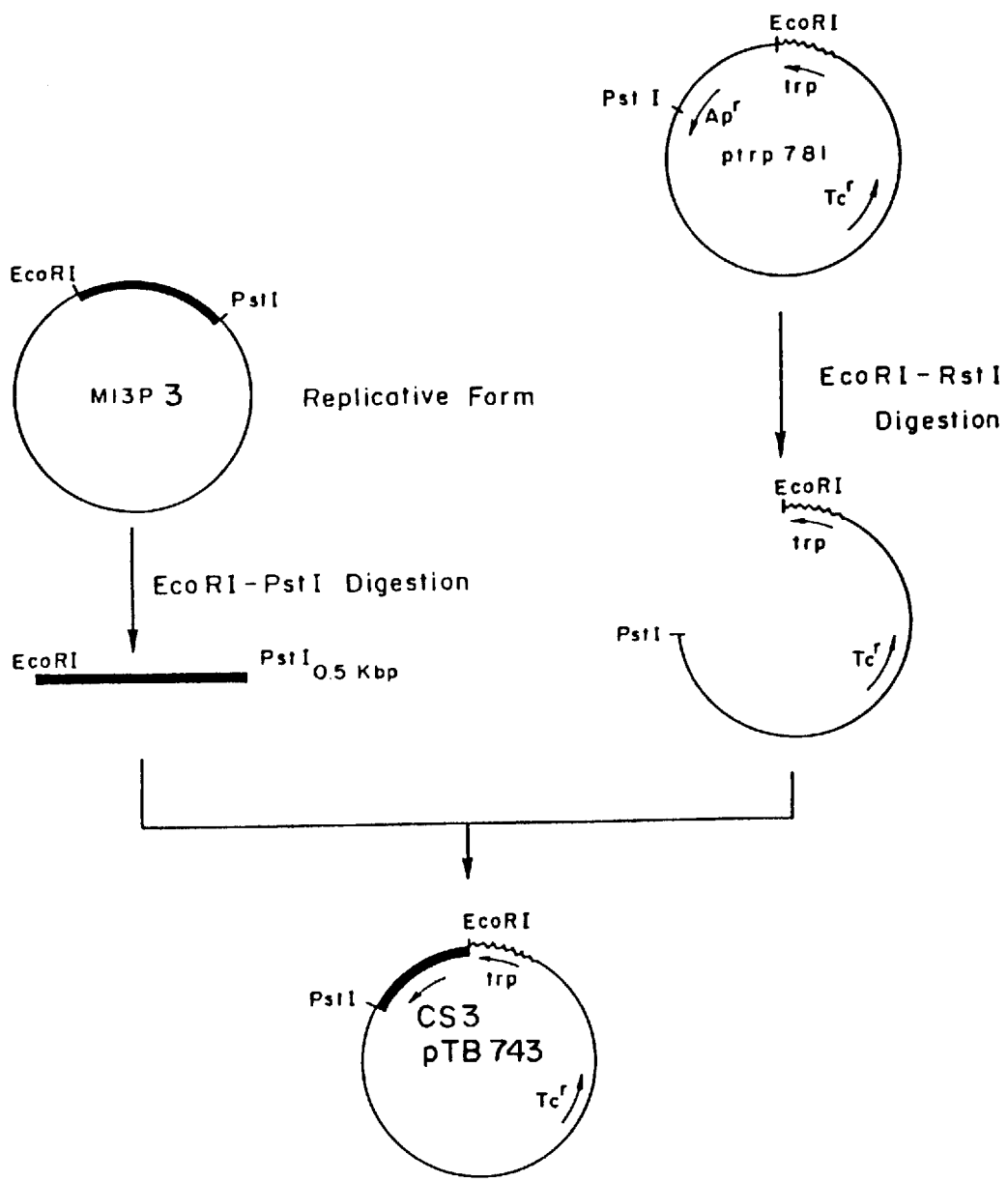
FIG. 9 shows the construction scheme of the plasmid pTB743 in Example 4 (1).

Separately, a plasmid ptrp781 DNA containing a trp promoter was cleaved using EcoRI-PstI to separate an about 3.2 kb DNA fragment containing a trp promoter, a tetracycline resistance gene and a plasmid replication initiation site. This 3.2 kb DNA fragment and the above-mentioned 0.5 kb EcoRI-PstI DNA fragment containing a gene region encoding a human bFGF mutein were ligated together by T4 DNA ligase reaction to construct the plasmid pTB743 for the expression of human bFGF mutein (FIG. 9).

Using this plasmid pTB743, *Escherichia coli* DH1 was transformed, whereby the strain *Escherichia coli* DH1/pTB743 (IFO 14585, FERM BP-1643) was obtained, which harbors the plasmid pTB743 containing the mutein-encoding gene shown in FIG. 5.

(2) Preparation of Bacterial Cell Extract:

The above-mentioned transformant was cultured in the manner described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract of *E. coli* DH1/pTB743 thereby tested exhibited FGF activity.

The mutein CS3, in which Cys at the 88-position of human bFGF had been replaced by Ser, was thus obtained.

EXAMPLE 5

(Expression in *Escherichia coli* of Gene which Encodes Human bFGF Mutein)

(1) Construction of the Plasmid pTB744 for Human bFGF Mutein Expression:

The M13-P4 replicative form (RF) obtained in Example 1 above was cleaved using the restriction enzymes EcoRI and PstI to obtain an about 0.5 kb DNA fragment containing a region which encodes a human bFGF mutein.

Figure 10:
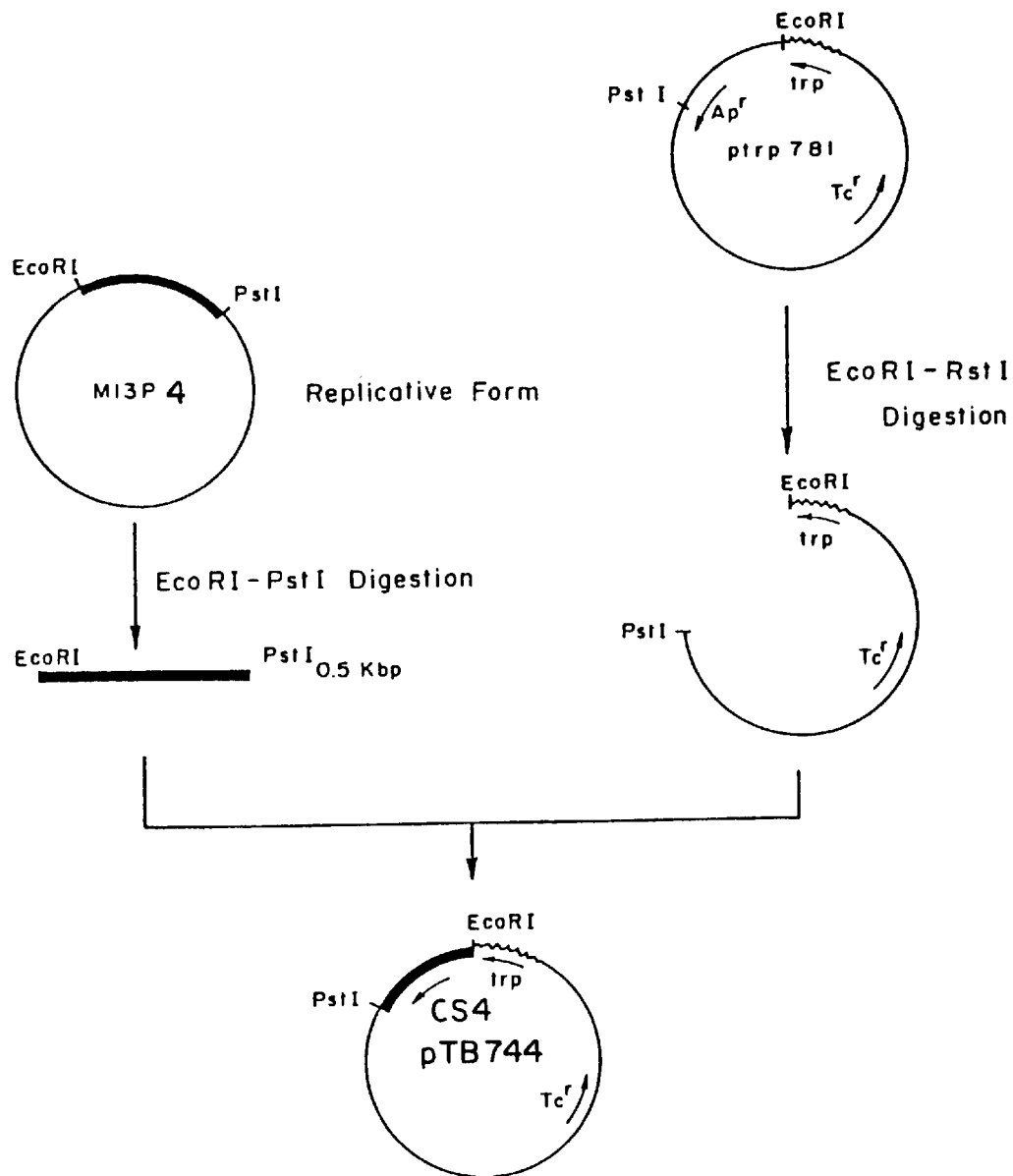
FIG. 10 shows the construction scheme of the plasmid pTB744 in Example 5 (1).

Separately, a plasmid ptrp781 DNA containing a trp promoter was cleaved using EcoRI-PstI to separate an about 3.2 kb DNA fragment containing a trp promoter, a tetracycline resistance gene and a plasmid replication initiation site. This 3.2 kb DNA fragment and the above-mentioned 0.5 kb EcoRI-PstI DNA fragment containing a gene region encoding a human bFGF mutein were ligated together by T4 DNA ligase reaction to construct the plasmid pTB744 for the expression of a human bFGF mutein (FIG. 10).

Using this plasmid pTB744, *Escherichia coli* DH1 was transformed, whereby the strain *Escherichia coli* DH1/pTB744 (IFO 14586, FERM BP-1644) was obtained, which harbors the plasmid pTB744 containing the mutein-encoding gene shown in FIG. 6.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* DH1/pTB744 thereby tested exhibited FGF activity.

The mutein CS4, in which Cys at the 93-position in human bFGF had been replaced by Ser was thus obtained.

EXAMPLE 6

(Screening and Identification of Plaques which were made Mutagenic)

Plates containing mutated M13-P2 phage plaques obtained in Example 1 and 2 plates containing unmutated M13-P2 phage plaques obtained in Example 1 were cooled to 4° C., and the plaque from each plate was transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl (pH 7.5) and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with $10^5$ cpm/ml of an oligonucleotide primer. The filters were each washed in a buffer solution for washing containing 0.1% SDS and a reduced amount of SSC at 50° C. for 30 minutes. The filters were then first washed with a buffer solution containing 2×SSC; the control filters, which contained unmutated M13-P2 plaques, were examined for radioactivity using a Geiger counter. While stepwise reducing SSC concentration, the control filters were washed until no detectable radioactivity remained on the filters. The minimum of the SSC concentrations was used 0.1×SSC. The filters were allowed to dry in air, and radioautographs were taken by 2 to 3 days of exposure at −70° C. Screening was carried out of 10,000 mutated M13-P2 plaques and 100 unmutated control plaques using a kinase-treated oligonucleotide probe. None of the control plaques hybridized to the probe, while 3 to 10 of the mutated M13-P2 plaques hybridized to the probe.

One of the mutated M13-P2 plaques was taken, and was inoculated to a JM105 culture medium. From the resulting supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the TGC (Cys-26) codon had been changed to a TCT (Ser) codon; the TGT (Cys-88) codon, to a TCT (Ser) codon; and the TGT (Cys-93) codon, to a TCT (Ser) codon.

Of the mutated M13-P2 phages, the phage in which the codons Cys-26 and -70 had become Ser-encoding codons was named M13-P12; the phage in which the codons Cys-70 and -88 had become Ser-encoding codons, M13-P23; and the phage in which the codons Cys-70 and -93 had become Ser-encoding codons, M13-P24.

EXAMPLE 7

(Expression in *Escherichia coli* of Gene Encoding Human bFGF Mutein)

Figure 12:
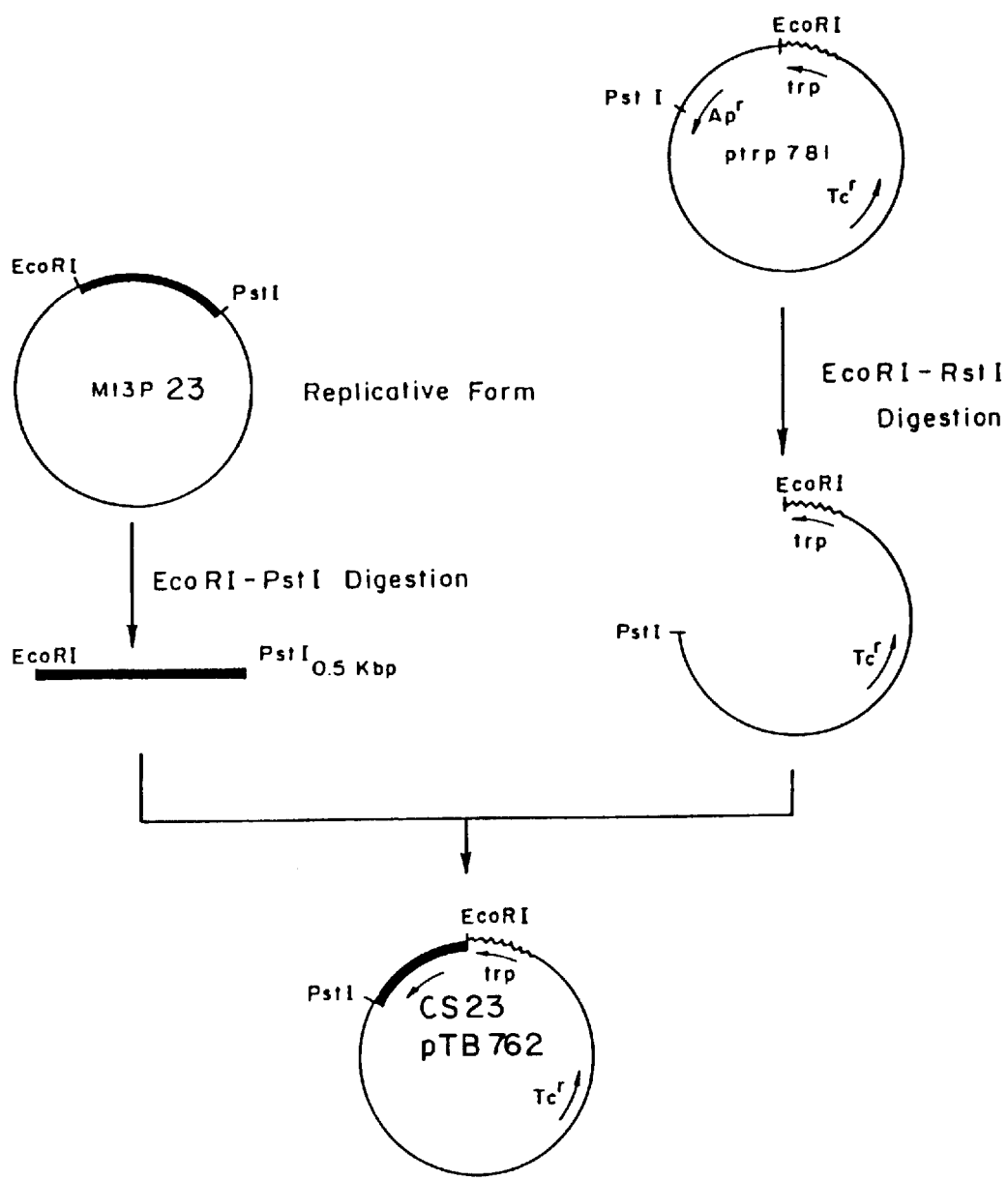
FIG. 12 shows the construction chart of the plasmid pTB762 in Example 7 (1).

(1) Construction of the Plasmid pTB762 for Human bFGF Mutein Expression:

The M13-P23 replicative form (RF) obtained in Example 6 above was treated in the manner described in Example 2 (1) to construct the plasmid pTB762 for human bFGF mutein expression (FIG. 12).

Using this plasmid pTB762, *Escherichia coli* MM294 was transformed, whereby the strain *Escherichia coli* MM294/pTB762 (IFO 14613, FERM BP-1645) was obtained, which harbors the plasmid pTB762 containing the mutein-encoding gene shown in FIG. 11.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB762 thereby tested exhibited FGF activity.

The mutein CS23, in which Cys at the 70-position and at the 88-position had been replaced by Ser, was thus obtained.

EXAMPLE 8

(Screening and Identification of Plaques made Mutagenic)

Plates containing mutated M13-P23 phage plaques obtained in Example 7 and 2 plates containing unmutated M13-P23 phage plaques obtained in Example 7 were cooled to 4° C., and the plaque from each plate was transferred to 2 round nitrocellulose filters by keeping a dry filter placed on the agar plate for 5 minutes in the case of te 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl (pH 7.5) and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with $10^5$ cpm/ml of an oligonucleotide primer. Each filter was washed in a buffer solution for washing containing 0.1% SDS and a reduced amount of SSC at 50° C. for 30 minutes. The filters were then first washed with a buffer solution containing 2×SSC; the control filters, which contained unmutated M13-P23 plaques, were examined for radioactivity using a Geiger counter. While stepwise reducing SSC concentration, the control filters, which contained unmutated M13-P23 plaques, were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-P23 plaques and 100 unmutated control plaques by means of a kinase-treated oligonucleotide probe. None of the control plaques hybridized to the probe, while 3 to 10 of the mutated M13-P23 plaques hybridized to the probe.

One of the mutated M13-P23 plaques was taken, and was inoculated to a JM105 culture medium. From the resulting supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the TGC (Cys-26) codon had been changed to a TCT (Ser) codon; and the TGT (Cys-93) codon, to a TCT (Ser) codon.

Of the mutated M13-P23 phages, the phage in which the codons Cys-26, -70 and -88 had become Ser-encoding codons was named M13-P123; and the phage in which the codons Cys-70, -88 and -93 had become Ser-encoding codons, M13-P234.

EXAMPLE 9

(Expression in *Escherichia coli* of Gene Encoding Human bFGF Mutein)

Figure 14:
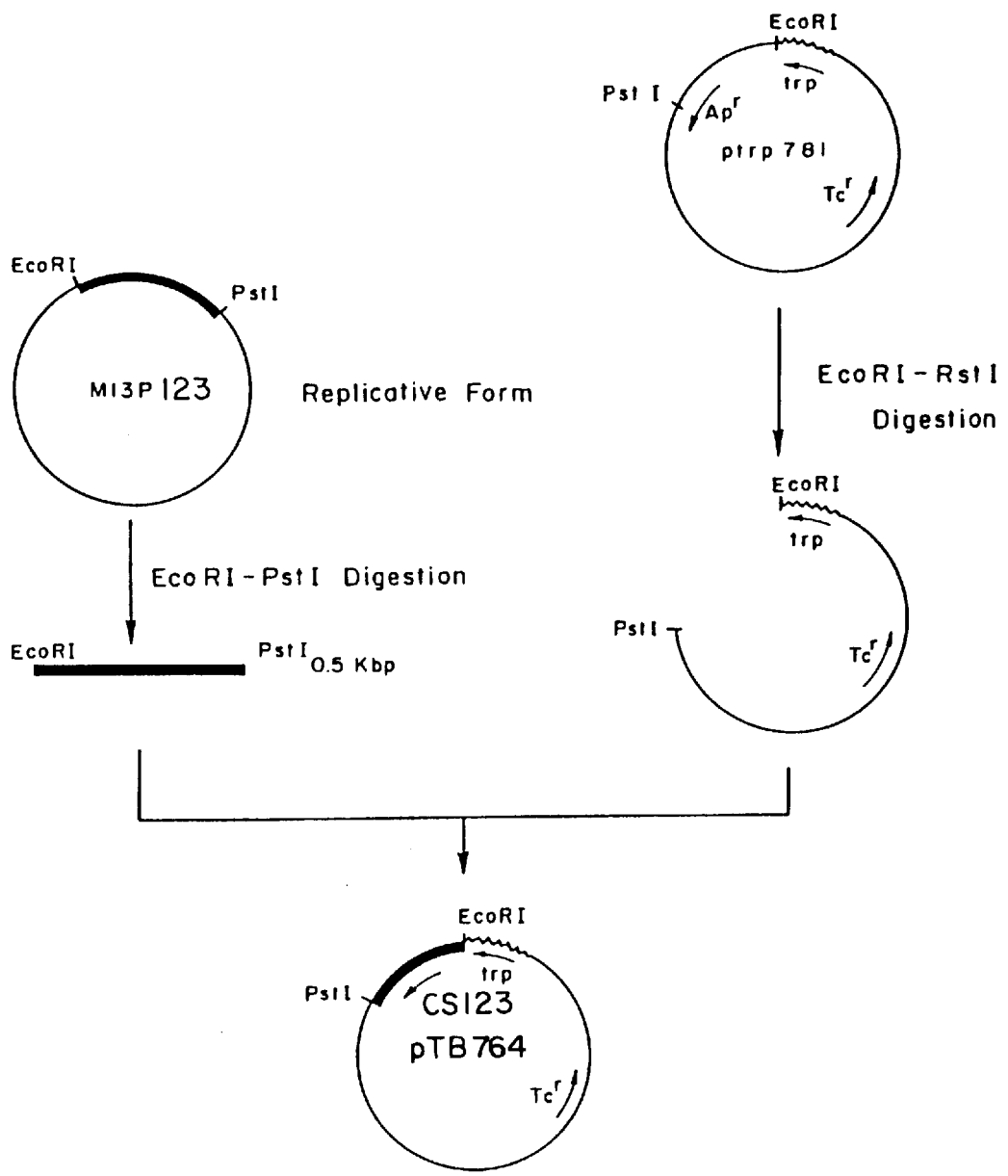
FIG. 14 shows the construction scheme of the plasmid pTB764 in Example 9 (1).

(1) Construction of the Plasmid pTB764 for Human bFGF Mutein Expression:

The M13-P123 replicative form (RF) obtained in Example 8 above was treated in the manner described in Example 2 (1) to construct the plasmid pTB764 for human bFGF mutein expression (FIG. 14).

Using this plasmid pTB764, *Escherichia coli* MM294 was transformed, whereby the strain *Escherichia coli* MM294/pTB764 (IFO 14614, FERM BP-1646) was obtained, which harbors the plasmid pTB764 containing the mutein-encoding gene shown in FIG. 13.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF acitivity of the bacterial cell extract obtained in (2) above, by the method described in Example 2 (3).

The bacterial cell extract from *E. coli* MM294/pTB764 thereby tested exhibited FGF activity.

The mutein CS123, in which Cys at the 26-, 70- and 88-positions in human bFGF had been replaced by Ser, was thus obtained.

EXAMPLE 10

(Screening and Identification of Plaques which were made Mutagenic)

Plates containing mutated M13-P123 phage plaques obtained in Example 8 and 2 plates containing unmutated M13-P123 phage plaques obtained in Example 8 were cooled to 4° C., and the plaque from each plate was transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl (pH 7.5) and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4 ×Denhardt's solution (polyvinyl-pyrrolidone, Ficoll and bovine serum albumin, 1×=0.02%), 0.1% sodium dodecyl sulfate (SDS), 50 mM sodium phosphate-buffered solution having a pH-value of 7.0 and 100μg/ml denatured salmon sperm DNA. Hybridization was carried out at 42° C. for 24 hours with $10^5$ cpm/ml of an oligonucleotide primer. The filters were each washed in a buffer solution for washing containing 0.1% SDS and a reduced amount of SSC at 50° C. for 30 minutes. The filters were then first washed with a buffer solution containing 2×SSC; the control filters, which contained unmutated M13-P123 plaques, were examined for radioactivity using a Geiger counter. While stepwise reducing SSC concentration, the control filters, which contained unmutated M13-P123 plaques, were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-P123 plaques and 100 unmutated control plaques by means of a kinase-treated oligonucleotide probe. None of the control plaques hybridized to the probe, while 3 to 10 of the mutated M13-P123 plaques hybridized to the probe.

One of the mutated M13-P123 plaques was taken, and was inoculated to a JM105 culture medium. From the resulting supernatant an ssDNA was prepared, and from the bacterial cell pelletes a double-stranded (ds) DNA was prepared. Analyses were made of the base sequence using an appropriate oligonucleotide primer and ssDNA.

As a result, it was confirmed that the TGT (Cys-93) codon had been changed to a TCT (Ser) codon.

Of the mutated M13-P123 phages, the phage in which the codons Cys-26, -70, -88 and -93 had become Ser-encoding codons was named M13-P1234.

EXAMPLE 11

(Expression in *Escherichia coli* of Gene Encoding Human bFGF Mutein)

Figure 16:
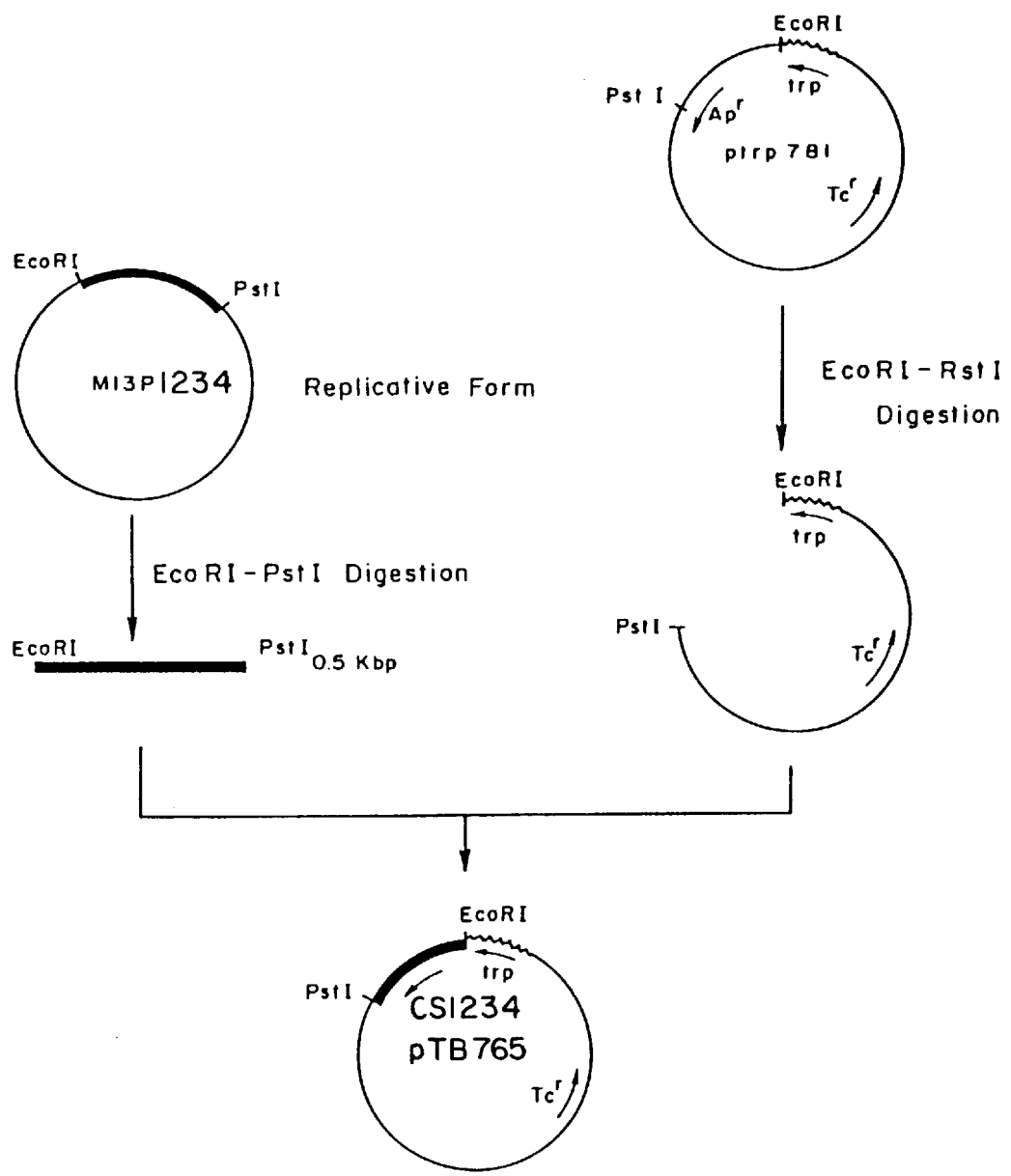
FIG. 16 shows the construction scheme of the plasmid pTB765 in Example 11 (1).

(1) Construction of the Plasmid pTB765 for Human bFGF Mutein Expression:

The M13-P1234 replicative form (RF) obtained in Example 10 above was treated in the manner described in Example 2 (1) to construct the plasmid pTB765 for the expression of a human bFGF mutein (FIG. 16).

Using this plasmid pTB765, *Escherichia coli* MM294 was transformed, whreby the strain *Escherichia coli* MM294/pTB765 (IFO 14615, FERM BP-1647) was obtained, which harbors the plasmid pTB765 containing the mutein-encoding gene shown in FIG. 15.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, in the manner described in Example 2 (3).

The bacterial cell extract from *E. coli* MM294/pTB765 thereby tested exhibited FGF activity.

The mutein CS1234, in which Cys at the 26-, 70-, 88- and 93-positions in human bFGF had been replaced by Ser, was thus obtained.

EXAMPLE 12

(Screening and Identification of Plaques which were made Mutagenic)

Plates containing M13-P1 phages mutated by the method of Example 1 using a synthetic oligomer [FIG. 2 (3) or (4)] and 2 plates containing unmutated M13-P1 phage plaques obtained in Example 1 were cooled to 4° C., and the plaque from each plate was transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl (pH 7.5) and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with $10^5$ cpm/ml of an oligonucleotide primer. The filters were each washed in a buffer solution for washing containing 0.1% SDS and a reduced amount of SSC at 50° C. for 30 minutes. The filters were then first washed with a buffer solution containing 2×SSC; the control filters, which contained unmutated M13-P1 plaques, were examined for radioactivity using a Geiger counter. While reducing SSC concentration stepwise, the control filters, which contained unmutated M13-P1 plaques, were washed until no detectable radioactivity remained on the filters. The minimum of the used SSC concentrations was 0.1×SSC. The filters were allowed to dry in air, and radioautographs were taken by 2 to 3 days of exposure at −70° C. Screening was carried out of 10,000 mutated M13-P1 plaques and 100 unmutated control plaques using an oligonucleotide probe treated with kinase in the presence of γ-$^{32}$P-ATP. None of the control plaques hybridized to the probe, while 3 to 10 of the mutated M13-P1 plaques hybridized to the probe.

One of the mutated M13-P1 plaques was taken, and was inoculated to a JM105 culture medium. From the resulting supernatant an ssDNA was prepared, and from the bacterial cell pellets a double-stranded (ds)DNA was prepared. Analyses were made of the base sequences using appropriate oligonucleotide primers and ssDNAs.

As a result, it was respectively confirmed that the TGT (Cys-88) codon had been changed to a TCT (Ser) codon; and the TGT (Cys-93) codon, to a TCT (Ser) codon.

Of the mutated M13-P1 phages, the phage in which the codons Cys-26 and -88 had become Ser-encoding codons was named M13-P13; and the phage in which the codons Cys-26 and -93 had become Ser-encoding codons, M13-P14.

EXAMPLE 13

(Screening and Identification of Plaques made Mutagenic)

Plates containing M13-P14 phage plaques mutated by the method of Example 1 using a synthetic oligomer [FIG. 2 (2) or (3)] and 2 plates containing unmutated M13-P14 phage plaques were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl (pH 7.5) and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 100 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with $10^5$ cpm/ml of an oligonucleotide primer. Each filter was washed in a buffer solution for washing containing 0.1% SDS and a reduced amount of SSC at 50° C. for 30 minutes. The filters were then first washed with a buffer solution containing 2×SSC; the control filters, which contained unmutated M13-P14 plaques, were examined for radioactivity using a Geiger counter. While reducing SSC concentration stepwise, the control filters, which contained unmutated M13-P14 plaques, were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-P14 plaques and 100 unmutated control plaques by means of an oligonucleotide probe treated with kinase in the presence of γ-$^{32}$P-ATP. None of the control plaques hybridized to the probe, while 3 to 10 of the mutated M13-P14 plaques hybridized to the probe.

One of the mutated M13-P14 plaques was taken, and was inoculated to a JM105 culture medium. From the resulting supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the TGT (Cys-70) codon had been changed to a TCT (Ser) codon; and the TGT (Cys-93) codon, to a TCT (Ser) codon.

Of the mutated M13-P14 phages, the phage in which the codons Cys-26, -70 and -93 had become Ser-encoding codons was named M13-P124; and the phage in which the codons Cys-26, -88 and -93 had become Ser-encoding codons, M13-P134.

EXAMPLE 14

(Screening and Identification of Plaques made Mutagenic)

Plates containing M13-P3 phage plaques mutated by the method of Example 1 using a synthetic oligomer [FIG. 2 (4)] and 2 plates containing unmutated M13-P3 phage plaques obtained in Example 1 were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them for 5 more minutes on filter papers immersed in 0.5M Tris-HCl having a pH-value of 7.5 and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with 10$^5$ cpm/ml of an oligonucleotide primer. The filters were each washed in a buffer solution for washing containing 0.1% SDS and a reduced amount of SSC at 50° C. for 30 minutes. The filters were then first washed with a buffer solution containing 2×SSC; the control filters, which contained unmutated M13-P3 plaques, were examined for radioactivity using a Geiger counter. While stepwise reducing SSC concentration, the control filters, which contained unmutated M13-P3 plaques, were washed until no detectable radioactivity remained on the filters. The minimum of the used SSC concentrations was 0.1×SSC. The filters were allowed to dry in air, and autoradiographs were taken by 2 to 3 days on exposure at −70° C. Screening was carried out of 10,000 mutated M13-P3 plaques and 100 unmutated control plaques by means of an oligonucleotide primer treated with kinase in the presence of γ-$^{32}$P-ATP. None of the control plaques hybridized to the probe, while 3 to 10 of the mutated M13-P3 plaques hybridized to the probe.

One of the mutated M13-P3 plaques was taken, and inoculated to a JM105 culture medium. From the resulting supernatant an ssDNA was prepared, and from the bacterial cell pellets a double-stranded (ds) DNA was prepared. Analyses were made of the base sequences using an appropriate oligonucleotide primer and ssDNA.

As a result, it was confirmed that the TGT (Cys-93) codon had been changed to a TCT (Ser) codon.

Of the mutated M13-P3 phages, the phage in which the codons Cys-88 and -93 had become Ser-encoding codons was named M13-P34.

EXAMPLE 15

(Expression in *Escherichia coli* of Gene which Encodes Human bFGF Mutein)

Figure 18:
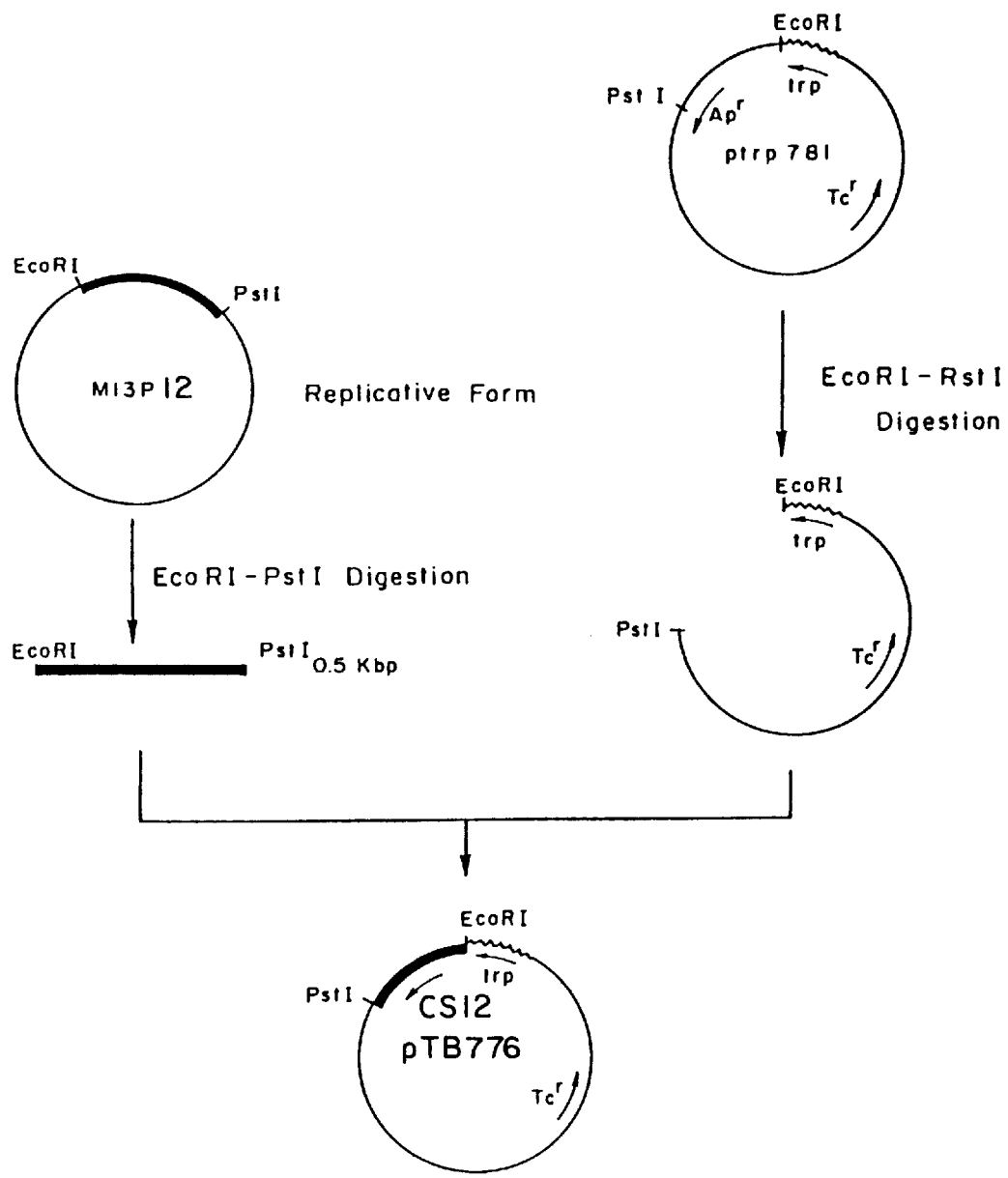
FIG. 18 shows the construction scheme of the plasmid pTB776 in Example 15 (1).

(1) Construction of the Plasmid pTB776 for Human bFGF Mutein Expression:

The M13-P12 replicative form (RF) obtained in Example 6 above was treated in the manner described in Example 2 (1) to construct the plasmid pTB776 for human bFGF mutein (FIG. 18).

Using this plasmid pTB776, *Escherichia coli* MM294 was transformed, whereby the strain *Escherichia coli* MM294/pTB776 was obtained, which harbors the plasmid pTB776 containing the mutein-encoding gene shown in FIG. 17.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB776 thereby tested exhibited FGF activity.

The mutein CS12, in which Cys at the 26- and 70-positions of human bFGF had been replaced by Ser, was thus obtained.

EXAMPLE 16

(Expression in *Escherichia coli* of Gene which Encodes Human bFGF Mutein)

Figure 20:
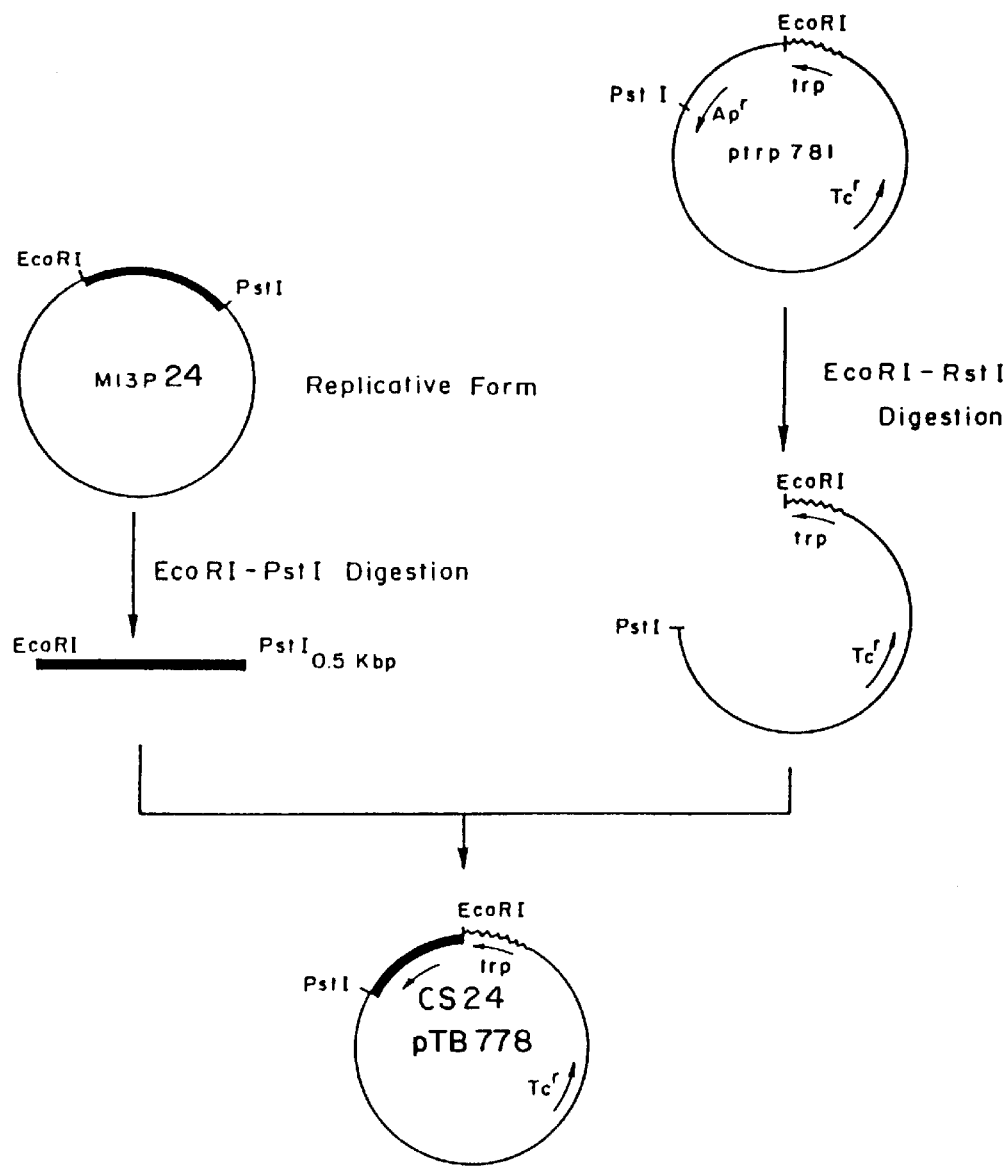
FIG. 20 shows the construction scheme of the plasmid pTB778 in Example 16 (1).

(1) Construction of the Plasmid pTB778 for Human bFGF Mutein Expression:

The M13-P24 replicative form (RF) obtained in Example 6 above was treated in the manner described in Example 2 (1) to construct the plasmid pTB778 for human bFGF mutein expression (FIG. 20).

Using this plasmid pTB778, *Escherichia coli* MM294 was transformed, whereby the strain *Escherichia coli* MM294/pTB778 was obtained, which contains the plasmid pTB778 containing the mutein-encoding gene shown in FIG. 19.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract of *E. coli* MM294/pTB778 thereby tested exhibited FGF activity.

The mutein CS24, in which Cys at the 70- and 93-positions of human bFGF had been replaced by Ser, was thus obtained.

EXAMPLE 17

(Expression in *Escherichia coli* of Gene which Encodes Human bFGF Mutein)

Figure 22:
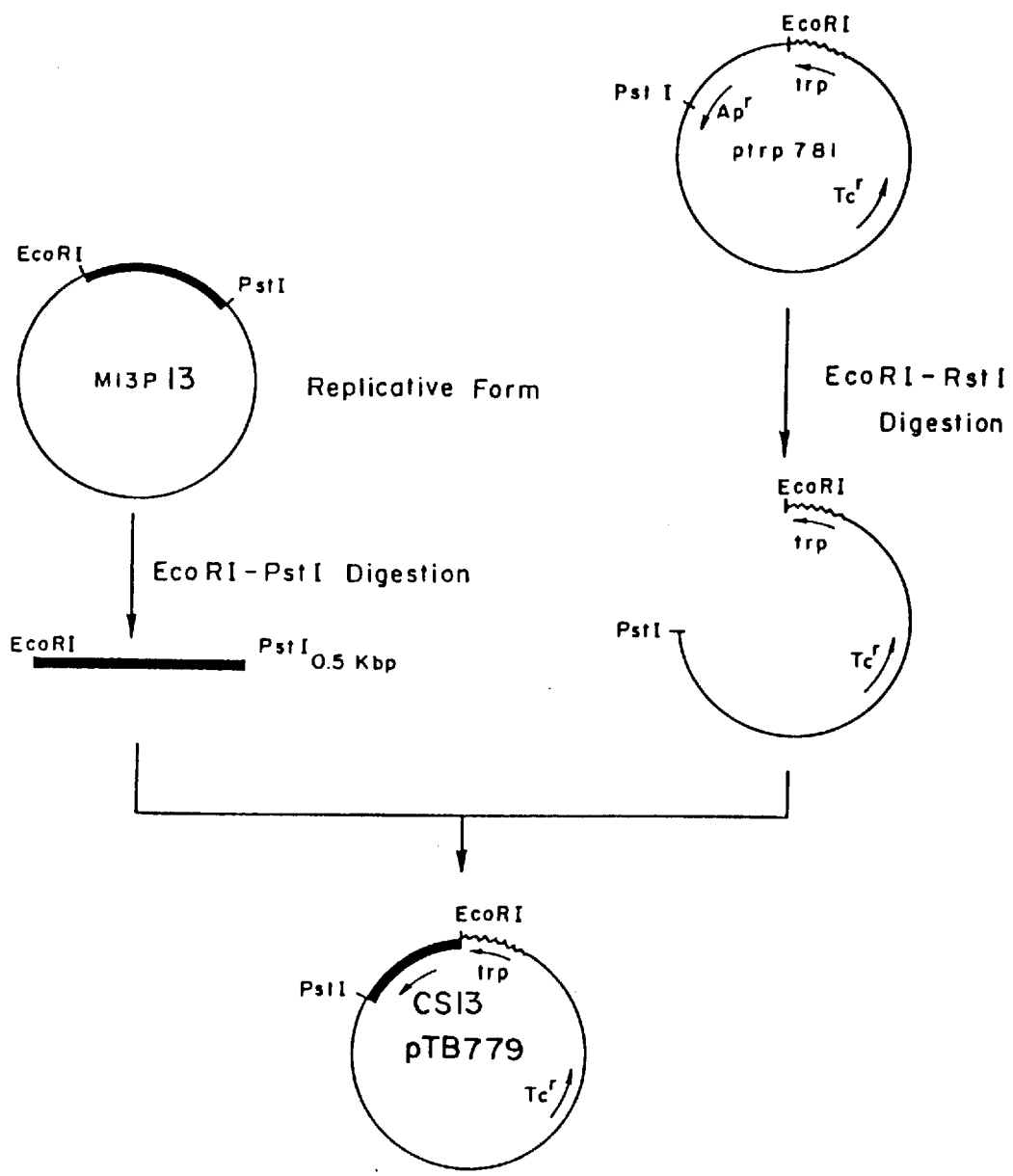
FIG. 22 shows the construction scheme of the plasmid pTB779 in Example 17 (1).

(1) Construction of the Plasmid pTB779 for Human bFGF Mutein Expression:

The M13-P13 replicative form (RF) obtained in Example 12 above was treated in the manner described in Example 2 (1) to construct the plasmid pTB779 for human bFGF mutein expression (FIG. 22).

Using this plasmid pTB779, *Escherichia coli* MM294 was transformed, whereby the strain *Escherichia coli* MM294/pTB779 was obtained, which harbors the plasmid pTB779 containing the mutein-encoding gene shown in FIG. 21.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract of *E. coli* MM294/pTB779 thereby tested exhibited FGF activity.

The mutein CS13, in which Cys at the 26- and 88-positions of human bFGF had been replaced by Ser, was thus obtained.

EXAMPLE 18

(Expression in *Escherichia coli* of Gene which Encodes Human bFGF Mutein)

Figure 24:
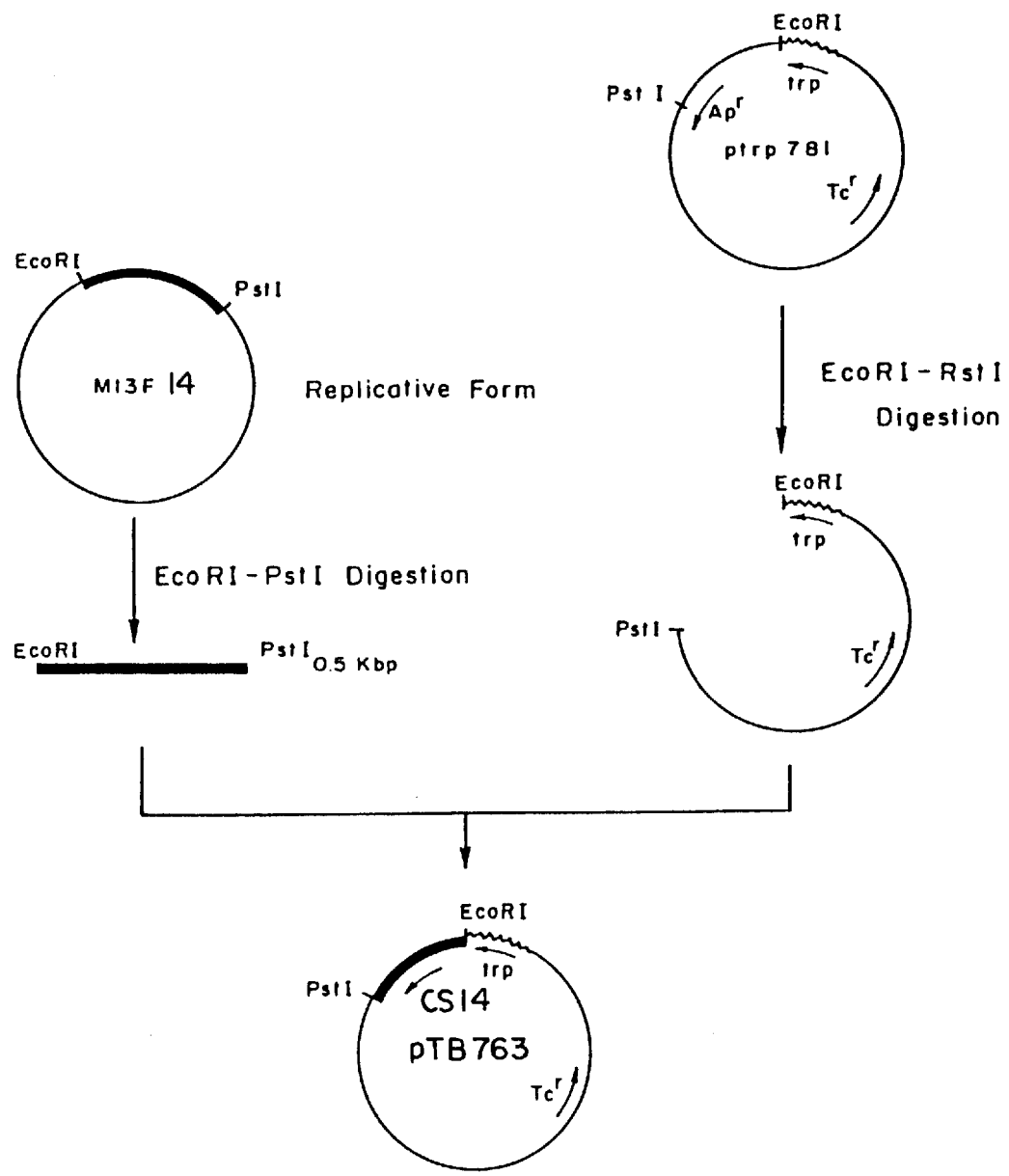
FIG. 24 shows the construction scheme of the plasmid pTB763 in Example 18 (1).

(1) Construction of the Plasmid pTB763 for Human bFGF Mutein Expression:

The M13-P14 replicative form (RF) obtained in Example 12 above was treated in the manner described in Example 2 (1) to construct the plasmid pTB763 for human bFGF mutein expression (FIG. 24).

Using this plasmid pTB763, *Escherichia coli* MM294 was transformed, whereby the strain *Escherichia coli* MM294/pTB763 was obtained, which harbors the plasmid pTB763 containing the mutein-encoding gene shown in FIG. 23.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract of *E. coli* MM294/pTB763 thereby tested exhibited FGF activity.

The mutein CS14, in which Cys at the 26- and 93-positions of human bFGF had been replaced by Ser, was thus obtained.

EXAMPLE 19

(Expression in *Escherichia coli* of Gene which Encodes Human bFGF Mutein)

Figure 26:
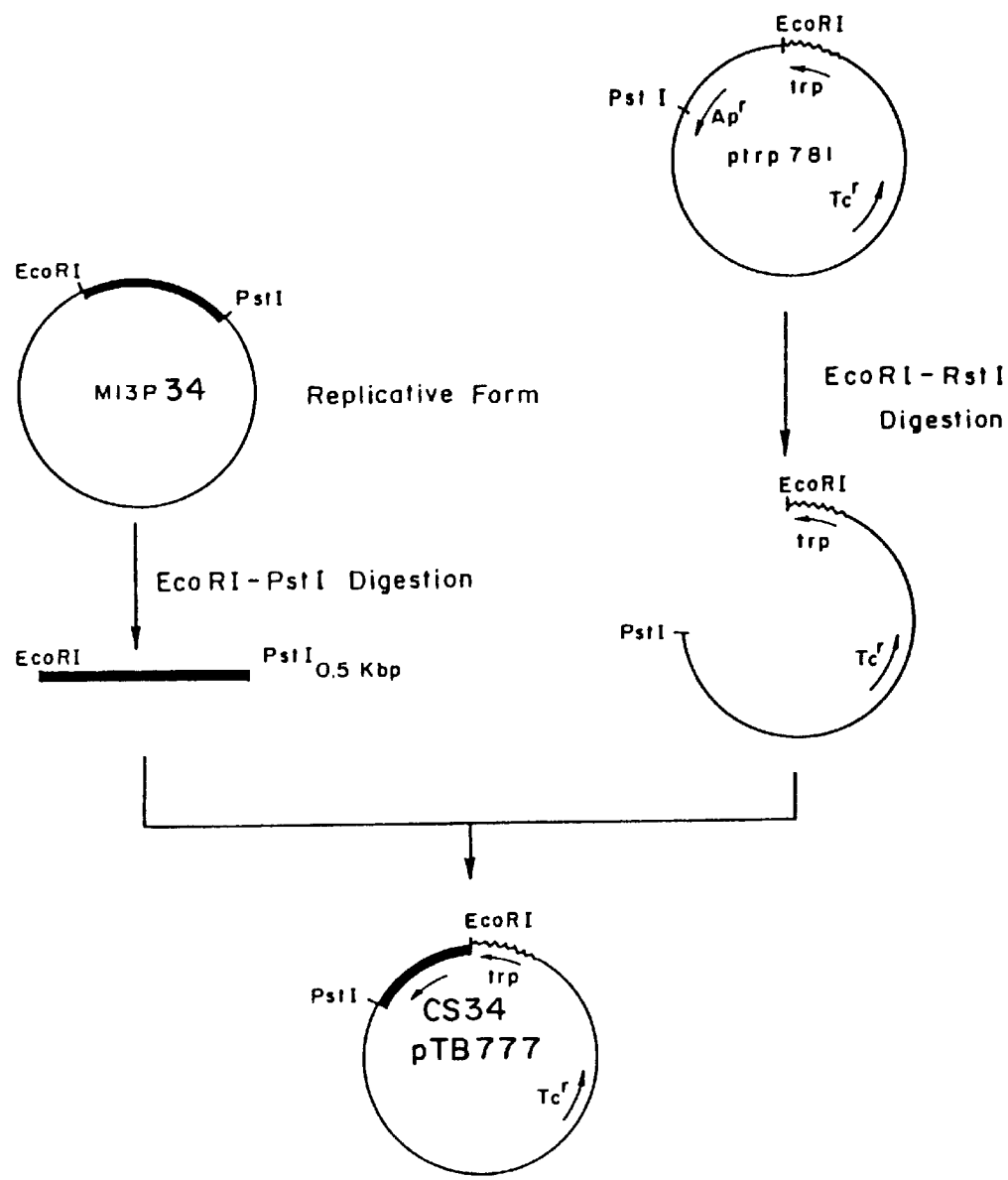
FIG. 26 shows the construction scheme of the plasmid pTB777 in Example 19 (1).

(1) Construction of the Plasmid pTB777 for Human bFGF Mutein Expression:

The M13-P34 replicative form (RF) obtained in Example 14 above was treated in the manner described in Example 2 (1) to construct the plasmid pTB777 for human bFGF mutein expression (FIG. 26).

Using this plasmid pTB777, *Escherichia coli* MM294 was transformed, whereby the strain *Escherichia coli* MM294/pTB777 was obtained, which harbors the plasmid pTB777 containing the mutein-encoding gene shown in FIG. 25.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract of *E. coli* MM294/pTB777 thereby tested exhibited FGF activity.

The mutein CS34, in which Cys at the 88- and 93-positions of human bFGF had been replaced by Ser, was thus obtained.

EXAMPLE 20

(Expression in *Escherichia coli* of Gene which Encodes Human bFGF Mutein)

Figure 28:
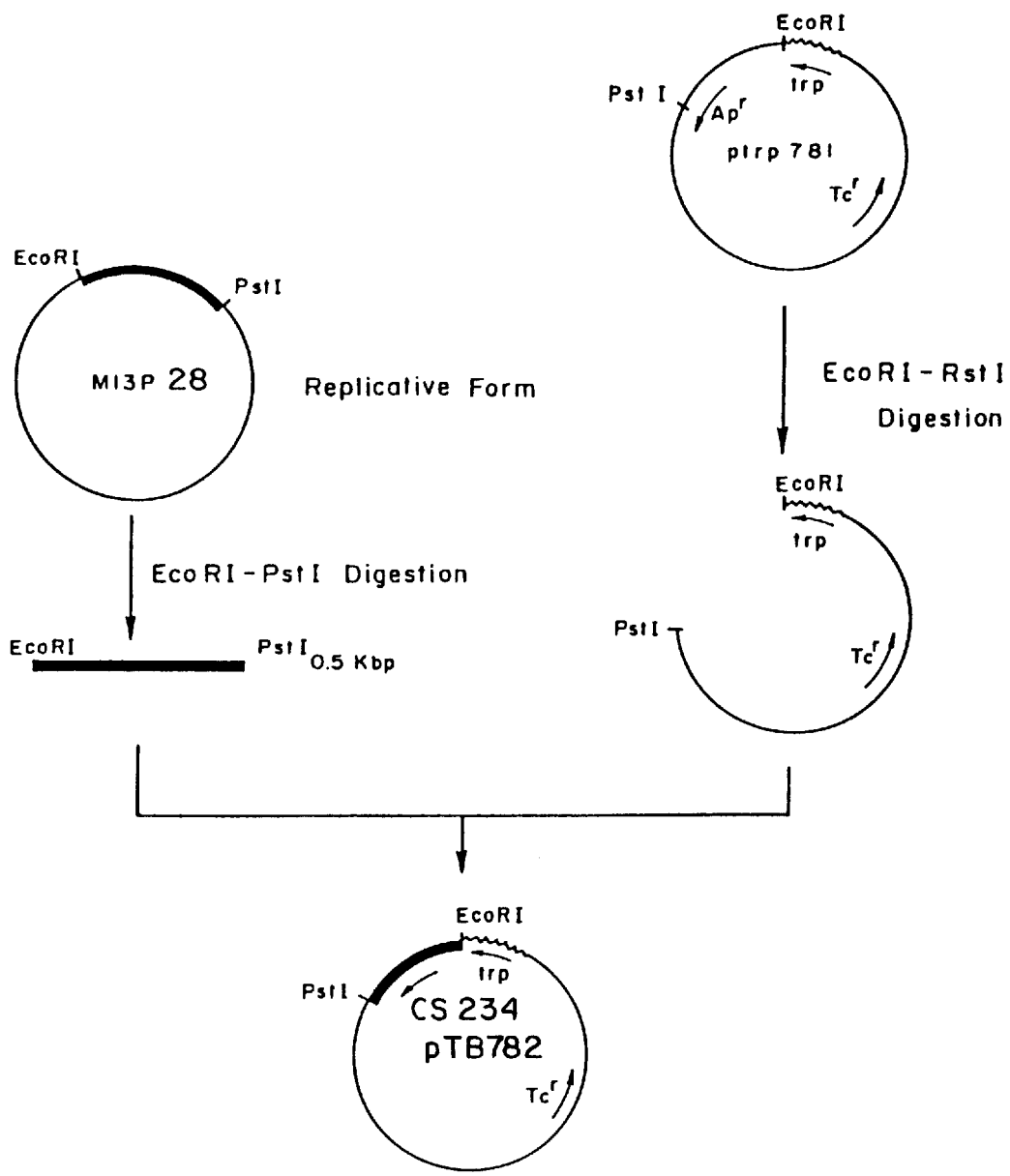
FIG. 28 shows the construction scheme of the plasmid pTB782 in Example 16 (1).

(1) Construction of the Plasmid pTB782 for Human bFGF Mutein Expression:

The M13-P234 replicative form (RF) obtained in Example 8 above was treated in the manner described in Example 2 (1) to construct the plasmid pTB782 for human bFGF mutein expression (FIG. 28).

Using this plasmid pTB782, *Escherichia coli* MM294 was transformed, whereby the strain *Escherichia coli* MM294/pTB782 was obtained, which harbors the plasmid pTB782 containing the mutein-encoding gene shown in FIG. 27.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract of *E. coli* MM294/pTB782 thereby tested exhibited FGF activity.

The mutein CS234, in which Cys at the 70-, 88- and 93-positions of human bFGF had been replaced by Ser, was thus obtained.

EXAMPLE 21

(Expression in *Escherichia coli* of Gene which Encodes Human bFGF Mutein)

Figure 30:
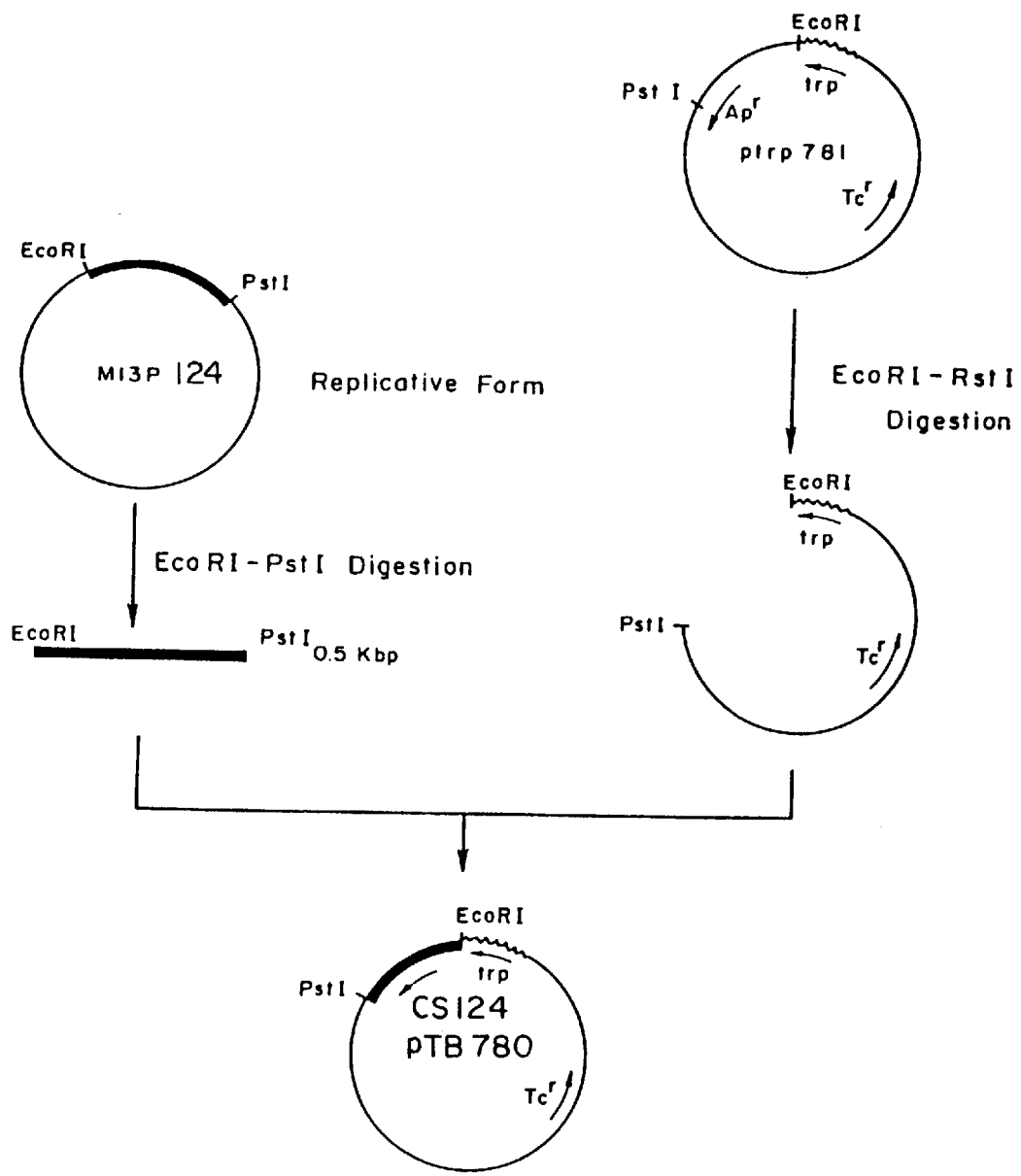
FIG. 30 shows the construction scheme of the plasmid pTB780 in Example 21 (1).

(1) Construction of the Plasmid pTB780 for Human bFGF Mutein Expression:

The M13-P124 replicative form (RF) obtained in Example 13 above was treated in the manner described in Example 2 (1) to construct the plasmid pTB780 for human bFGF mutein expression (FIG. 30).

Using this plasmid pTB780, *Escherichia coli* MM294 was transformed, whereby the strain *Escherichia coli* MM294/pTB780 was obtained, which harbors the plasmid pTB780 containing the mutein-encoding gene shown in FIG. 29.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract of *E. coli* MM294/pTB780 thereby tested exhibited FGF activity.

The mutein CS124, in which Cys at the 26-, 70- and 93-positions of human bFGF had been replaced by Ser, was thus obtained.

EXAMPLE 22

(Expression in *Escherichia coli* of Gene which Encodes Human bFGF)

(1) Construction of the Plasmid pTB781 for Human bFGF Mutein Expression:

The M13-P134 replicative form (RF) obtained Example 13 above was treated in the manner described in Example 2 (1) to construct the plasmid pTB781 for human bFGF mutein expression (FIG. 31).

Figure 32:
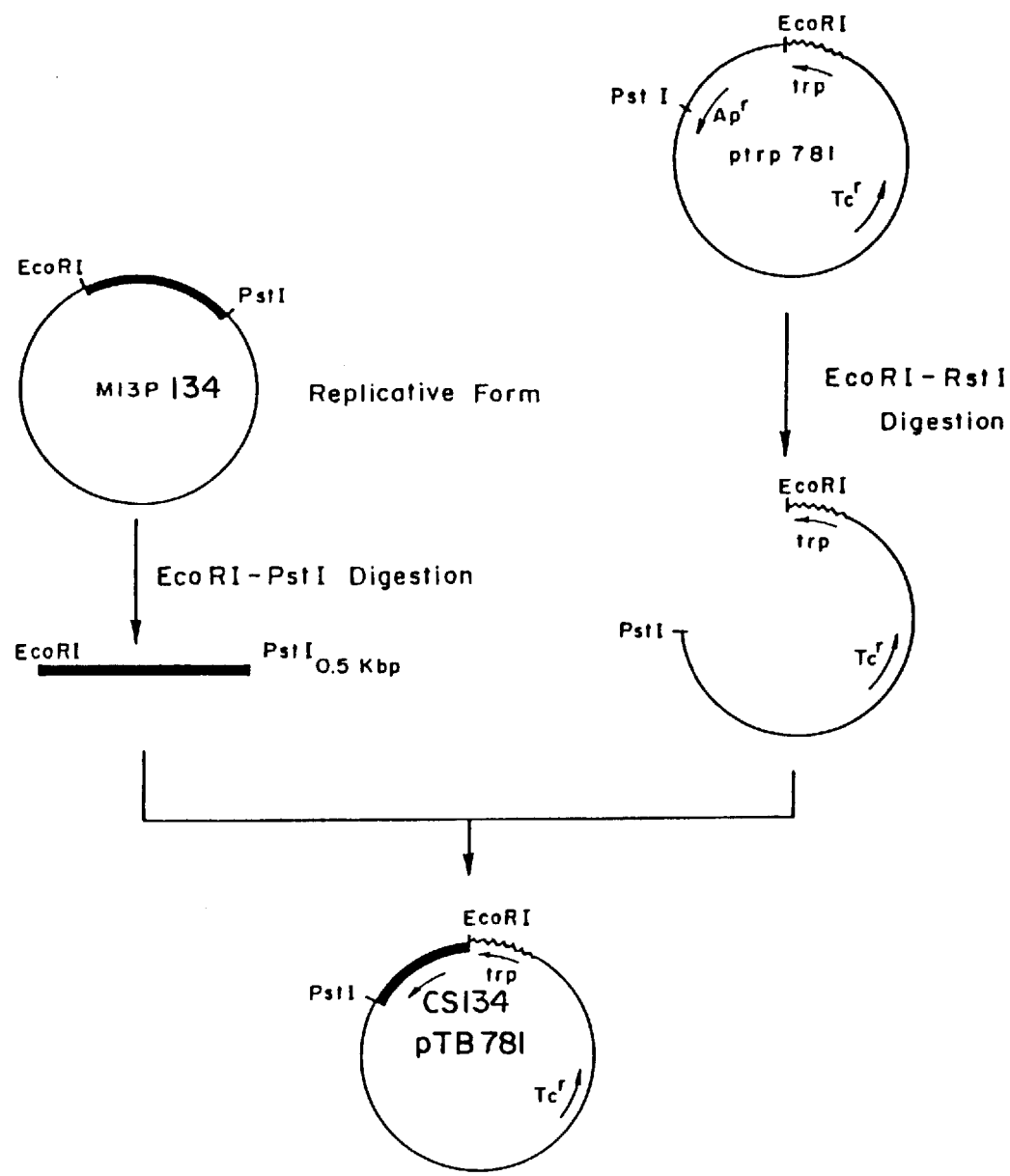
FIG. 32 shows the construction scheme of the plasmid pTB781 in Example 22 (1).

Using this plasmid pTB781, *Escherichia coli* MM294 was transformed, whereby the strain *Escherichia coli* MM294/pTB781 was obtained, which harbors the plasmid pTB781 containing the mutein-encoding gene shown in FIG. 32.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract of *E. coli* MM294/pTB781 thereby tested exhibited FGF activity.

The mutein CS134, in which Cys at the 26-, 88- and 93-positions of human bFGF had been replaced by Ser, was thus obtained.

EXAMPLE 23

(Mutein Productivities)

Determinations were made of the FGF activities of bacterial cell extracts containing respective muteins in accordance with the method of Reference example 2 (2), whereby the mutein productivities of respective transformants were calculated. The values thus obtained are shown in Table 3.

TABLE 3

| Plasmid | Mutein | Productivity (mg-ptFGF/1 culture) |
| --- | --- | --- |
| pTB739 | CS1 | 0.3 |
| pTB742 | CS2 | 10.6 |
| pTB743 | CS3 | 13.3 |
| pTB744 | CS4 | 0.8 |
| pTB776 | CS12 | 0.2 |
| pTB779 | CS13 | 0.1 |
| pTB763 | CS14 | 0.5 |
| pTB762 | CS23 | 25.8 |
| pTB778 | CS24 | 0.3 |
| pTB777 | CS34 | 0.5 |
| pTB764 | CS123 | 0.3 |
| pTB780 | CS124 | 0.4 |
| pTB781 | CS134 | 0.2 |
| pTB782 | CS234 | 1.4 |
| pTB765 | CS1234 | 0.1 |
| pTB669 | rhbFGF | 6.0 |
| ptrp781 | — | 0.0 |

EXAMPLE 24

(Purification of hbFGF Mutein)

Transformants producing respective muteins were cultured by the method described in Reference example 2, whereby bacterial cell extracts were prepared. 25 ml of each extract (prepared from 500 ml of the culture medium) was passed through a column ($\phi$2×10 cm) of DEAE cellulose (DE52, Wattman, Inc., United Kingdom) equilibrated with a solution containing 20 mM Tris-HCl having a pH-value of 7.4 and 0.2M NaCl, whereby the nucleic acid constituents in the extract were removed. The effluent from the column and the washings resulting from the washing of the column with a solution containing 20 mM Tris-HCl having a pH-value of 7.4 and 0.2M NaCl were combined and collected (DEAE effluent fraction, 60 ml).

This fraction was subjected to high performance liquid chromatography using a high performance liquid chromatograph (Gilson, Inc., France) loaded with a Shodex AF-pak HR-894 heparin column (8 mm ID×5 cm, produced by Showa Denko, Japan). After washing the column with a 20 mM Tris-HCl solution having a pH-value of 7.4, and then with a solution containing 20 mM Tris-HCl having a pH-value of 7.4 and 0.5M NaCl, linear gradient elution was carried out with the NaCl gradient of from 0.5M to 2M (60 ml volume, 1.0 ml/min. flow rate) in a buffer containing 20 mM Tris-HCl having a pH-value of 7.4.

Figure 33:
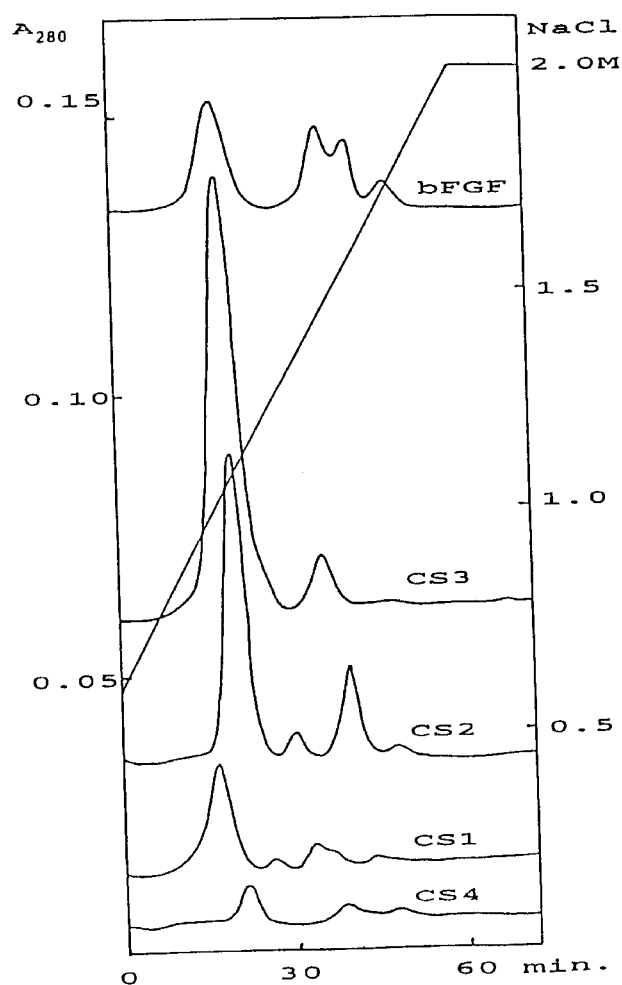
FIGS. 33 to 35 show the high performance liquid chromatography elution patterns of the muteins obtained in Example 24.
Figure 34:
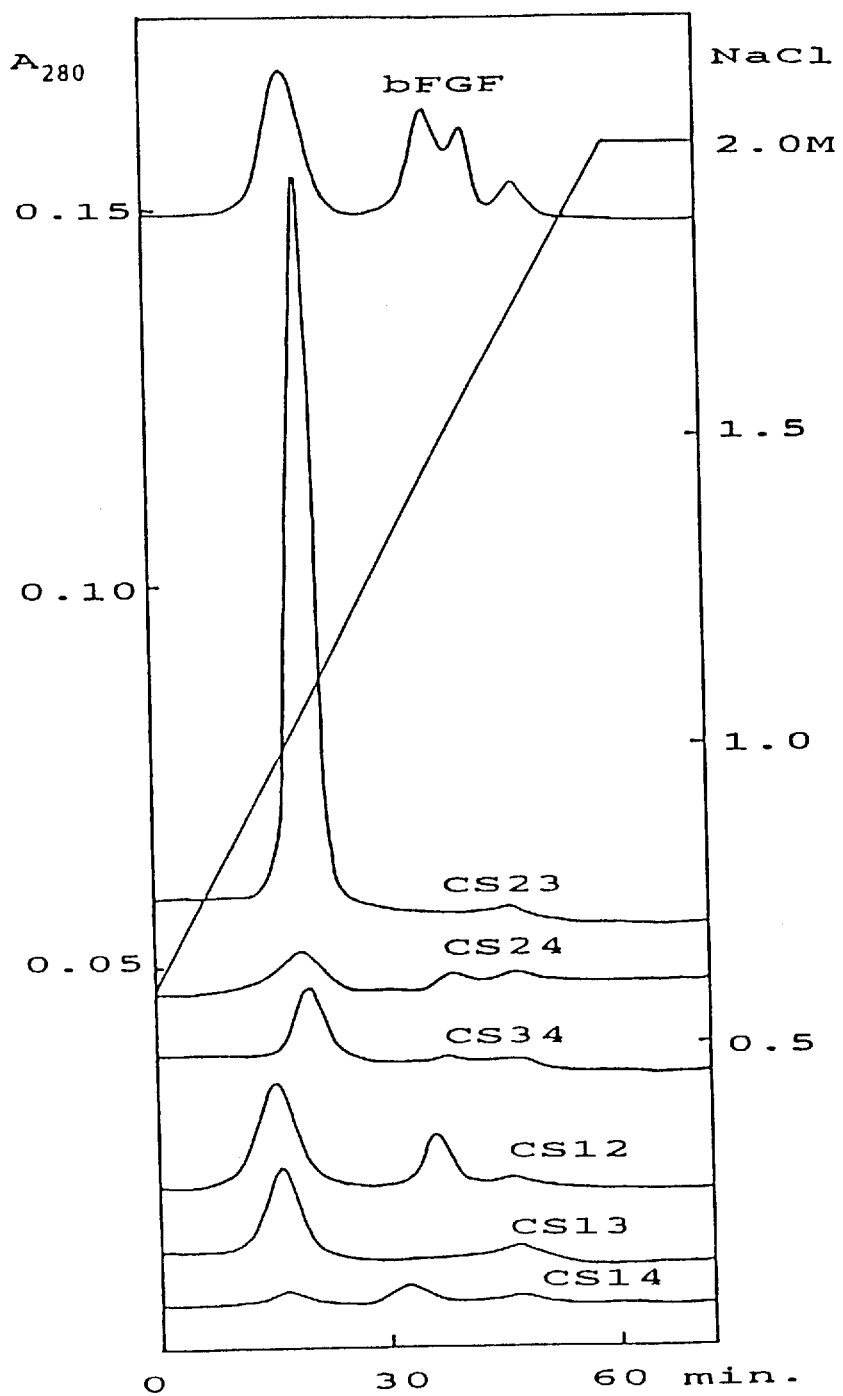
Figure 35:
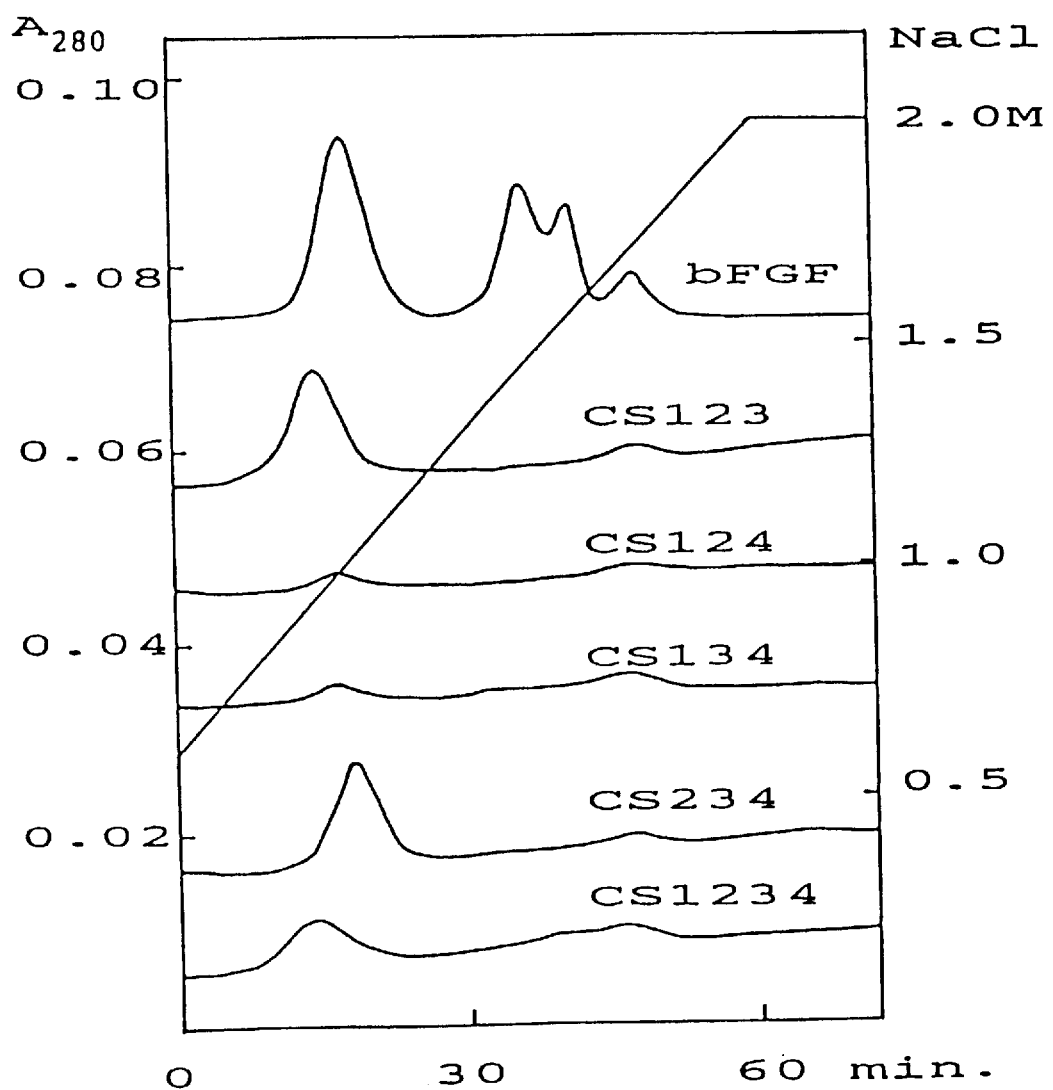

The elution patterns of respective muteins are shown in FIGS. 33 to 35. In these figures, the ordinates represent absorptions for $OD_{280}$ and NaCl concentrations in the gradient. The abscissas represent times, gradient elution being initiated on the time-0 point. Peak fractions were collected, and their FGF activities were investigated. The post-purification specific activities thereof are shown in Table 4.

TABLE 4

| Mutein | Specific Activity (mg-ptFGF/mg protein) |
| --- | --- |
| CS1 | 0.4 |
| CS2 | 0.9 |
| CS3 | 1.0 |
| CS4 | 1.0 |
| CS12 | 0.5 |
| CS13 | 0.5 |
| CS14 | 0.3 |
| CS23 | 1.1 |
| CS24 | 0.8 |
| CS34 | 0.5 |
| CS123 | 0.4 |
| CS124 | 0.1 |
| CS134 | 0.5 |
| CS234 | 0.9 |
| CS1234 | 0.1 |
| rhbFGF | 1.0 |

In Table 4, the specific activities are shown on the basis of the FGF activity of bovine brain-derived FGF (purity, not less than 95%) produced by Takara Shuzo Co., Ltd.

In all muteins, the peak corresponding to Peak I of bFGF was eluted at an elution time between 15 and 25 minutes. This can also be detected as a single band at the position of about 17,000 molecular weight in 17.25% SDS polyacrylamide gel electrophoresis.

EXAMPLE 25

(Oxidation of FGF Muteins)

Each mutein eluted from a heparin HPLC column and bFGF were separately twice dialyzed at 4° C. for 3 hours to a 1,000-fold amount by volume of distilled water, and this was followed by lyophilization. 200 $\mu$g (protein basis) of each dry standard sample was dissolved in 200 $\mu$l of an oxidation reaction liquid [50 mM Tris-HCl (pH 8.5)/0.2M NaCl/1 mg/ml BSA/20 mM H$_2$O$_2$], and oxidation was carried out at 37° C. for 30 minutes.

Figure 36:
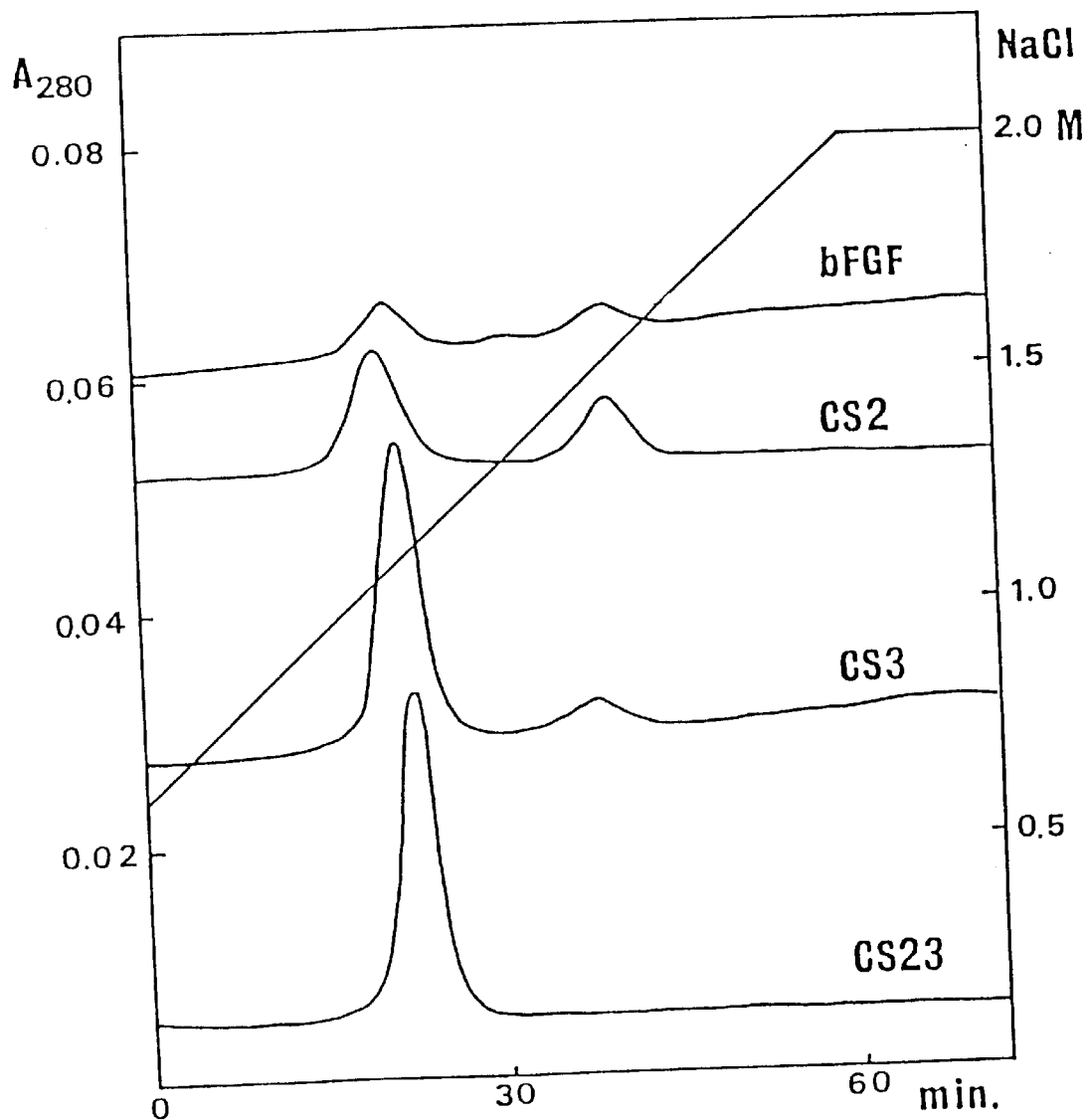
FIG. 36 shows the high performance liquid chromatography elution patterns of the mutein oxides obtained in Example 25.

The solution was then passed through a heparin HPLC column, and the pattern which appeared in elution with the salt gradient between 0.6M and 2M was examined. The obtained elution patterns are shown in FIG. 36. In bFGF, the peaks were generally low; while in CS2, CS3 and CS23, the peak corresponding to Peak I was high; the peak rise was noticeable specifically in CS3 and CS23.

This suggests that CS3 and CS23 are stable to oxidation. In addition, in all cases of CS2, CS3 and CS23, the protein eluted as the peak exhibited FGF activity.

EXAMPLE 26

(Reduction of FGF Muteins)

200 μg (protein basis) of each lyophilized standard sample obtained in the same manner as in Example 25 was dissolved in 200 μl of a reduction reaction liquid [50 mM Tris-HCl (pH 8.5)/0.2M NaCl/1 mg/ml BSA/20 mM dithiothreitol (DTT)], and reduction was carried out at 37° C. for 30 minutes.

Figure 37:
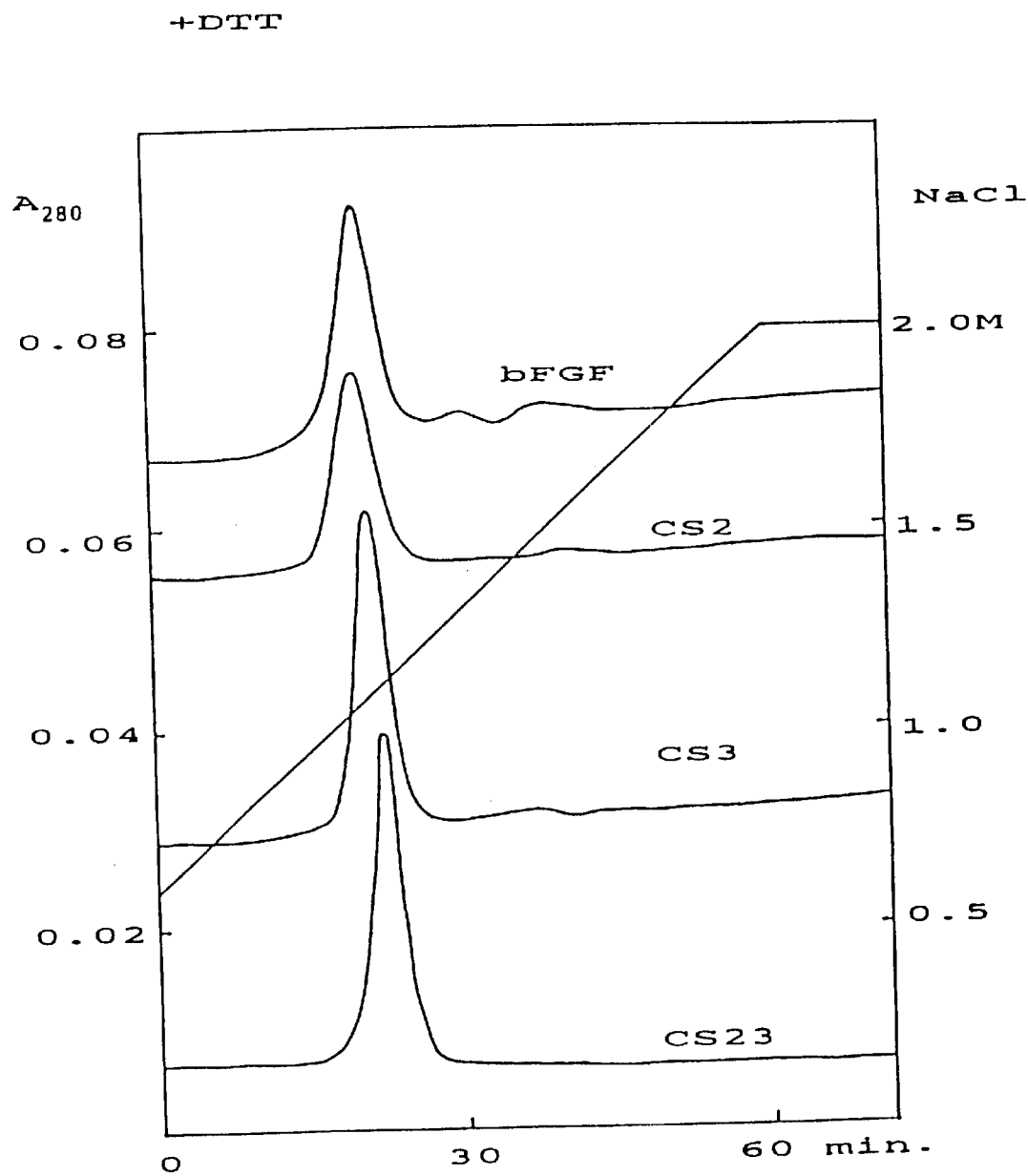
FIG. 37 shows the high performance liquid chromatography elution patterns of the mutein reduction products obtained in Example 26.

The solution was then passed through a heparin HPLC column, and the pattern which appeared in elution with the salt gradient between 0.6M and 2M was examined. The obtained elution patterns are shown in FIG. 37. In bFGF and CS2, the peak corresponding to Peak I was noticeable, and it was suggested that the other peaks (Peaks II to IV) are attributable to oxidation. It was also suggested that, in CS3 and CS23, the peak is not affected by oxidation. That is, this supports the stability referred to in Example 25. The bFGF and muteins eluted as these peaks were found to possess FGF activity.

EXAMPLE 27

(Production of Recombinant DNAs having Mutein-Encoding Base Sequence)

(1) Cloning of M13 Vector for Human bFGF Gene:

The plasmid pTB669 obtained in Reference example 2 was digested with the restriction enzymes EcoRI and BamHI. Phage vector M13mp8 [J. Messing, Methods in Enzymology, 101, 20–78 (1983)] replicative form (RF) DNA was mixed with a human bFGF DNA fragment derived from pTB669, previously digested with EcoRI and BamHI. The mixture was then subjected to ligation using T4 DNA ligase. The resulting ligated DNA was transformed into infectable cells of the strain *Escherichia coli* JM105; the transformant cells were spread over a plate whose indicator species was Xgal [J. Messing et al., Nucleic Acids Research, 9, 309–321 (1981)]; the plaque containing the recombinant phage (white plaque) was picked up; the base sequence of the recombinated region was determined by the dideoxynucleotide synthesis chain termination method [J. Messing et al., Nucleic Acids Research, 9, 309 (1981)], whereby it was confirmed that the human bFGF DNA had been accurately inserted.

From this M13-PO clone was purified a single-stranded phage DNA, which was used as a template for site-directed mutagenesis using a synthetic oligonucleotide.

(2) Site-Specific Mutagenesis:

In the presence of 0.1 mM adenosine triphosphate (ATP), 50 mM hydroxymethylaminomethane hydrochloride (Tris-HCl) having a pH-value of 8.0, 10 mM MgCl$_2$, 5 mM dithiothreitol (DTT) and 9 units of T4 kinase, in a total amount of 50 μl, 40 picomoles of the synthetic oligonucleotide:

5'-CGGGCATGAATTCGCCGCT-3'

[primer for producing in the base sequence a recognition site for the restriction enzyme EcoRI, and subsequently changing Pro-14 to Met (see FIG. 38 (2))] was treated with T4 kinase at 37° C. for 1 hour. This kinase-treated primer (12 picomoles) was heated at 67° C. for 5 minutes, and at 42° C. for 25 minutes, in 50 μl of a mixture containing 50 mM NaCl, 1.0 mM Tris-HCl having a pH-value of 8.0, 10 mM MgCl$_2$ and 10 mM β-mercaptoethanol, whereby it was hybridized to 5 μg of the single-stranded (ss) M13-PO DNA. The annealed mixture was then cooled on ice, and was added to 50 μl of a reaction mixture containing 0.5 mM deoxynucleotide triphosphate (dNTP), 80 mM Tris-HCl having a pH-value of 7.4, 8 mM MgCl$_2$, 100 mM NaCl, 9 units of DNA polymerase I Klenow fragment, 0.5 mM ATP and 2 units of T4 DNA ligase, and reaction was carried out at 37° C. for 3 hours, and at 25° C. for 2 hours, whereafter the reaction was stopped by adding 2 μl of 0.2 mM EDTA. The reaction product was used to transform infectable JM 105 cells; the transformant cells were allowed to grow overnight, whereafter an ssDNA was isolated from the culture medium supernatant. Using this ssDNA as a template for the 2nd cycle of primer elongation, gel-purified RF-type DNA was transformed into infectable JM 105 cells; the resulting transformant cells were spread over an agar plate, and were cultured overnight to obtain phage plaques.

(3) Site-Directed Mutagenesis:

The procedure of the above term (2) was repeated but the synthetic oligonucleotide primer used was: 5'-CGCCCATGGTGCCATCCTC-3' which produces in the base sequence a recognition site for the restriction enzyme NcoI, and concurrently changes Gly-9 to Thr and Ser-10 to Met, respectively. [See FIG. 38 (1).]

(4) Site-Directed Mutagenesis:

The procedure of the above term (2) was repeated but the synthetic oligonucleotide primer used was: 5'-TAACACCTTAAGAAGCCAG-3' which produces in the base sequence a recognition site for the restriction enzyme AflII, and concurrently changes the Lys-87-encoding codon to a termination codon. [See FIG. 38 (3).]

(5) Site-Directed Mutagenesis:

The procedure of the above term (2) was repeated but the synthetic oligonucleotide primer used was: 5'-CCGGACTCCGTTAACTCGG-3' which produces in the base sequence a recognition site for the restriction enzyme HpaI, and concurrently changes Asp42 to Asn. [See FIG. 38 (4).]

(6) Site-Directed Mutagenesis:

The procedure of the above term (2) was repeated but the synthetic oligonucleotide primer used was: 5'-CTTCTCCTGGACTCCGTCAAC-3' which deletes the recognition site for the restriction enzyme HpaII in the base sequence, and concurrently changes Arg45 to Gln. [See FIG. 38 (5).]

(7) Screening and Identification of Plaques which were Mutagenic:

Plates containing mutated M13-PO plaques [above term (1)] and 2 plates containing unmutated M13-PO phage plaques were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl having a pH-value of 7.5 and 1.5M NaCl. The filters were twice washed on filters immersed in 2×SSC (Standard Sodium Citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 µg/ml denatured salmon sperm DNA. Hybridization was carried out at 42° C. for 24 hours with $10^5$ cpm/ml of an oligonucleotide primer. Each filter was washed at 50° C. for 30 minutes in a buffer solution for washing containing 0.1% SDS and a reduced amount of SSC. The filters were then first washed with a buffer solution containing 2×SSC; the control filters, which contained unmutated M13-PO plaques, were examined for radioactivity using a Geiger counter. While stepwise reducing SSC concentration, the control filters, which contained unmutated M13-PO plaques, were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-PO plaques and 100 unmutated control plaques by means of an oligonucleotide probe treated with $^{32}$P-γ-ATP. None of the control plaques hybridized to the probe, while 3 to 10 of the mutated M13-PO plaques hybridized to the probe.

One of the mutated M13-PO plaques was taken, and was inoculated to a JM105 culture medium. From the resulting supernatant an ssDNA was prepared, and from the bacterial cell pellets a double-stranded (ds) DNA was prepared. Analyses were made of the base sequences using appropriate oligonucleotide primers and ssDNAs.

As a result, it was respectively confirmed that the GGC (Gly-9) codon had been changed to an ACC (Thr) codon and the AGC (Ser-10) codon had been changed to an ATG (Met) codon; the CCG (Pro-14) codon, to an ATG (Met) codon; the AAA (Lys-87) codon, to a TAA (termination) codon; the GAC (Asp-42) codon, to an AAC (Asn-42) codon; and the CGG (Arg-45) codon, to a CAG (Gln-45) codon.

Of the mutated M13-PO phages, the phage in which Gly-9 codon had become a Thr-encoding codon and the Ser-10 codon had become a Met-encoding codon was named M13-PN10 [Its base sequence and the amino acid sequence encoded thereby are shown in FIG. 39.];
the phage in which the Pro-14 codon had become a Met-encoding codon, M13-PN14 [Its base sequence and the amino acid sequence encoded thereby are shown in FIG. 40];
the phage in which the Lys-87 codon had become a termination codon, M13-PC86 [Its base sequence and the amino acid sequence encoded thereby are shown in FIG. 41]:
the phage in which the Asp-42 codon had become an Asn-encoding codon, M13-PDN42 [Its base sequence and the amino acid sequence encoded thereby are shown in FIG. 42]; and,
the phage in which the Arg-45 codon had become a Gln-encoding codon, M13-PRQ45 [Its base sequence and the amino acid sequence encoded thereby are shown in FIG. 43].

EXAMPLE 28

(Production of Recombinant DNAs having Mutein-Encoding Base Sequence)
(1) Site-Specific Mutagenesis:
In the presence of 0.1 mM adenosine triphosphate (ATP), 50 mM hydorxymethylaminomethane hydrochloride (Tris-HCl) having a pH-value of 8.0, 10 mM MgCl$_2$, 5 mM dithiothreitol (DTT) and 9 units of T4 kinase, in a total amount of 50 µl, 40 picomoles of the synthetic oligonucleotide:

5'-CGGACTCCTCTAACTCGGC-3'

[primer for deleting the recognition site for the restriction enzyme HpaI in the base sequence, and subsequently changing Asn-42 to Arg (see FIG. 38 (6)] was treated with T4 kinase at 37° C. for 1 hour. This kinase-treated primer was heated at 67° C. for 5 minutes, and at 42° C. for 25 minutes, in 50 µl of a mixutre containing 50 mM NaCl, 1.0 mM Tris-HCl having a pH-value of 8.0, 10 mM MgCl$_2$ and 10 mM β-mercaptoethanol, whereby it was hybridized to 5 µg of the single-stranded (ss) M3-PDN 42 DNA. The annealed mixture was then cooled on ice, and was added to 50 µl of a reaction mixture containing 0.5 mM deoxynucleotide triphosphate (dNTP), 80 mM Tris-HCl having a pH-value of 7.4, 8 mM MgCl$_2$, 100 mM NaCl, 9 units of DNA polymerase I Klenow fragment, 0.5 mM ATP and 2 units of T4 DNA ligase, and reaction was carried out at 37° C. for 3 hours, and at 25° C. for 2 hours, whereafter the reaction was stopped by adding 2 µl of EDTA. The reaction product was used to transform infectable JM 105 cells; the transformant cells were allowed to grow overnight, whereafter an ssDNA was isolated from the culture medium supernatant. Using this ssDNA as a template for the 2nd cycle of primer elongation, gel-purified RF-type DNA was transformed into infectable JM 105 cells; the resulting transformant cells were spread over an agar plate, and were cultured overnight to obtain phage plaques.

(2) Screening and Identification of Plaques made Mutagenic:
Plates containing M13-PDN42 phage plaques mutated by the method of Example 26 using a synthetic oligomer [FIG. 38 (6)] and 2 plates containing unmutated M13-PDN42 phage plaques obtained in Example 26 were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl having a pH-value of 7.5 and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC) having a pH-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 µg/ml denatured salmon sperm DNA. Hybridization was carried out at 42° C. for 24 hours with $10^5$ cpm/ml of an oligonucleotide primer. Each filter was washed in a buffer solution containing 0.1% SDS and a reduced amount of SSC at 50° C. for 30 minutes. The filters were then first washed with a buffer solution containing 2×SSC; the control filters, which contained unmutated M13-PDN42 plaques were examined for radioactivity using a Geiger counter. While stepwise reducing SSC concentration, the control filters, which contained unmutated M13-PDN42 plaques, were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-PDN42 plaques and 100 unmutated control plaques by means of an oligonucleotide probe treated with kinase in the presence of $^{32}$P-γ-ATP. None of the control plaques hybridized to the probe, while 3 to 10 of the mutated M13-PDN42 plaques hybridized to the probe.

One of the mutated M13-PDN42 plaques was taken, and was inoculated to a JM105 culture medium. From the resulting supernatant an ssDNA was prepared, and from the bacterial cell pellets a double-stranded (ds)DNA was prepared. Analyses were made of the base sequence using an appropriate oligonucleotide primer and ssDNA.

As a result, it was confirmed that the AAC (Asn-42) codon had been changed to an AGA (Arg) codon.

Of the mutated M13-PDN42 phages, the phage in which the Asn-42 codon had become an Arg-encoding codon was named M13-PNR42. Its base sequence and the amino acid sequence encoded thereby are shown in FIG. 44.

EXAMPLE 29

(Stabilities of the Muteins CS2, CS3 and CS23)

Figure 45:
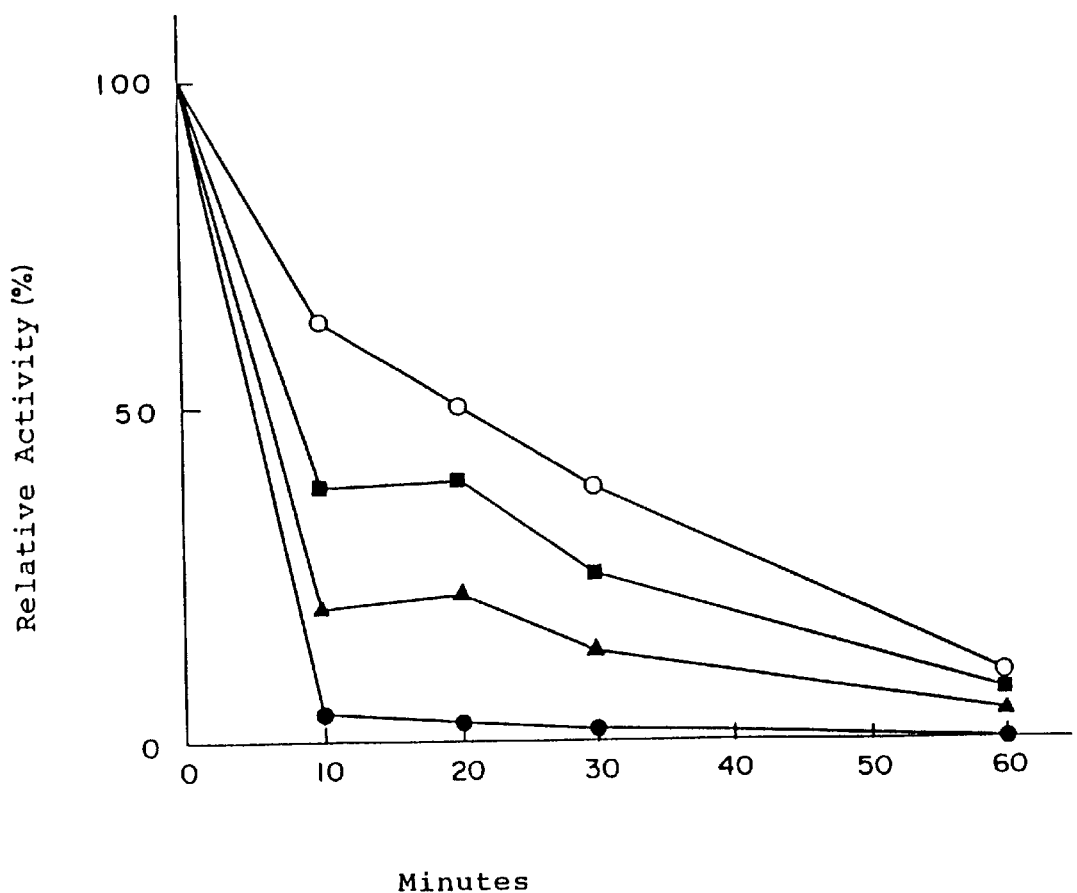
FIG. 45 shows the stability of the human bFGF muteins CS2, CS3 and CS23, obtained in Example 29.

Examinations were made of the stabilities under acid conditions of human bFGF purified by heparin HPLC and the muteins CS2, CS3 and CS23 (those obtained in Example 24) as follows: The muteins and human bFGF, in solution in 50 mM Na-acetate (pH 4.0) adjusted to 1 μg/ml concentration, were separately incubated at 37° C. Incubation time was varied between 0 and 1 hour at intervals of 10 minutes, and activities were determined for respective incubation times using the mouse BALB/c3T3 cell system (mentioned above). Activities for respective incubation times were calculated in percent ratio based on the activities of non-incubated standard samples, taken as 100%, and were plotted to obtain the graphs shown in FIG. 45. In FIG. 45, —●—, —▲—, —■— and —O— respectively indicate the results from human bFGF, the mutein CS2, the mutein CS3 and the mutein CS23. Human bFGF almost completely inactivated itself within 10 minutes, while the muteins remained active for longer periods in the ascending order of CS2, CS3 and CS23. The mutein CS23 maintained about 50% activity even 20 minutes later. As a result, these muteins proved to have greater stability than that of human bFGF.

EXAMPLE 30

(Human Umbilical Cord Vascular Endothelial Cell Proliferation Promoting Activities of Muteins)

Determinations were made of the vascular endothelial cell proliferation promoting activities of human bFGF purified by heparin HPLC and the muteins CS2, CS3 and CS23 (those obtained in Example 24). The procedure used for the determinations is as follows: Human vascular endothelial cells were obtained from human umbilical cord vein by perfusion using a trypsin solution, and were maintained by subculture using liquid medium prepared by adding 2.5% fetal bovine serum and 2.0 ng/ml human bFGF to GIT medium (produced by Daigo Nutritive Chemicals, Ltd., Japan). To a 96-well cultivation plate (Nunc, 1-67008) 100 μl of a suspension of 2×10³ human vascular endothelial cells was seeded, and this was followed by cultivation in a constant temperature chamber filled with carbon dioxide. Next day, FGF in such amount that final concentration was 2 ng/ml and 100 μl of a medium containing samples at various concentrations were added. After 3 days of cultivation, the medium containing the sample was aspirated, and 100 μl of a 1 mg/1 ml MTT solution (prepared by dissolving 3-(4,5-dimethyl-2-thiazolyl)-2,5-diphenyl-2H-tetrazolium bromide in the medium) was added, and this was followed by incubation for 4 hours. 100 μl of a 10% SDS solution (aqueous solution of sodium dodecyl sulfate) was then added, and incubation was carried out for 5 to 6 hours to solubilize the cells and MTT pigment, whereafter $OD_{590}$ value was determined by means of a spectrophotometer. Calculations were made of the cell proliferation rates for respective sample concentrations in percent ratio based on the maximum proliferation rate obtained with 8.0 ng/ml human bFGF, taken as 100%, and determinations were made of the specific activities by comparing the concentrations which resulted in 50% proliferation rate with the concentration of standard FGF sample. The specific activities thus determined are shown in Table 5.

TABLE 5

| FGF | Specific Activity |
| --- | --- |
| CS2 | 1.6 |
| CS3 | 3.0 |
| CS23 | 2.5 |
| Human bFGF | 1.0 |

Based on these results, it was recognized that the muteins are higher in specific activity than human bFGF.

EXAMPLE 31

(Angioneogenesis Potencies of Muteins, Determined by the CAM Method)

Investigations were made of the angioneogenesis potencies in vivo of human bFGF purified by heparin HPLC and the muteins CS2, CS3 and CS23 (those obtained in Example 24). The procedure was by CAM (Chorio-allantoic membrane) assay. A slightly modified technique of Auerbach's method [Developmental Biology, 41, 391 (1974)] was used for CAM assay. After 3 days of incubation at 37° C. in an incubator, fertilized fowl eggs had their shells removed, and were further incubated at 37° C. for 1 more week using a Napco carbon dioxide incubator 6300 ($CO_2$:0%, $H_2O$: saturated). An aqueous solution of each protein was spotted over polypropylene disks having a diameter of 6 mm so that each protein was present in amounts of 6.25, 12.5, 25.0 and 50.0 ng. After air-drying in clean bench, the disks were incubated at 37° C. for 3 more days while kept standing on fowl chorio-allantoic membrane, and observations were made of angiogenesis states by means of a stereoscopic microscope. The obtained results are shown in Table 6. NB: A total of 18 eggs for each sample were used, and the figures in the table represent in percent ratio the numbers of eggs in which angiogenesis was noted.

TABLE 6

| | Angiogenesis Potency (%) | | | |
| --- | --- | --- | --- | --- |
| FGF | 50.0 | 25.0 | 12.5 | 6.25 ng |
| CS2 | 77.8 | 44.4 | 22.2 | 0.0 |
| CS3 | 72.2 | 61.1 | 16.7 | 0.0 |
| CS23 | 72.2 | 55.6 | 22.2 | 0.0 |
| Human bFGF | 94.4 | 50.0 | 33.3 | 0.0 |
| Carrier | 11.1 | 5.6 | 11.1 | 0.0 |

From Table 6, it is obvious that the bFGF muteins possess angiogenesis potencies which are nearly equivalent to that of the control human bFGF.

EXAMPLE 32

(Expression in *Escherichia coli* of Gene which Encodes Human bFGF Mutein)

Figure 46:
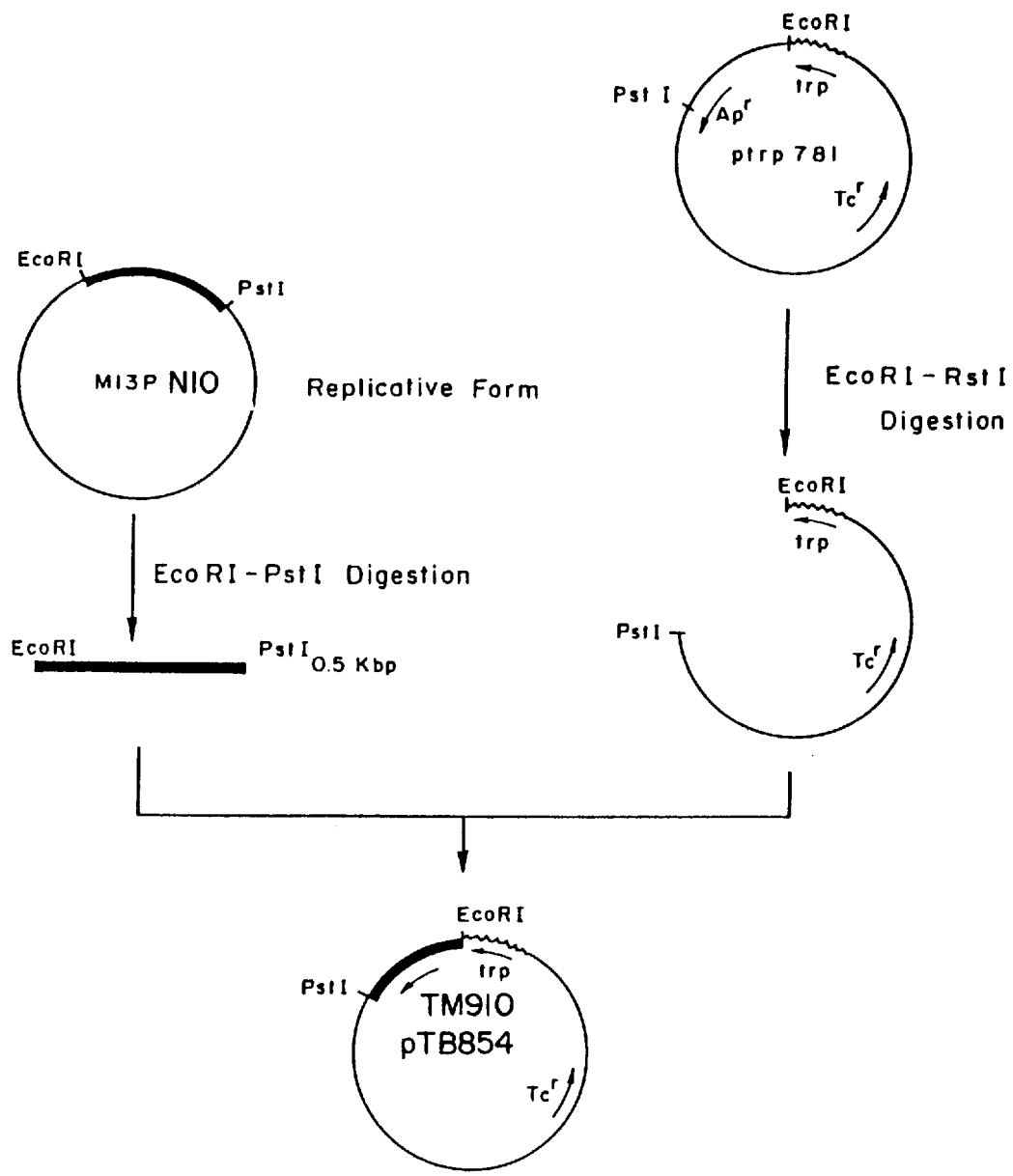
FIG. 46 shows the construction scheme of the plasmid pTB854 in Example 32.

(1) Construction of the Plasmid pTB854 for Human bFGF Mutein Expression:

The M13-PN10 replicative form (RF) obtained in Example 27 above was treated in the manner described in Example 2 (1) to construct the plasmid pTB854 for human bFGF mutein (FIG. 46).

Using this plasmid pTB854, *Escherichia coli* MM294 was transformed, whereby the strain *Escherichia coli* MM294/pTB854 was obtained, which harbors the plasmid pTB854 containing the mutein-encoding gene shown in FIG. 39.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB854 thereby tested exhibited FGF activity.

The mutein TM910, in which Gly at the 9-position and Ser at the 10-position of human bFGF had been replaced by Thr and Met, respectively, was thus obtained.

EXAMPLE 33

(Expression in *Escherichia coli* of Gene which Encodes Human bFGF Mutein)

Figure 47:
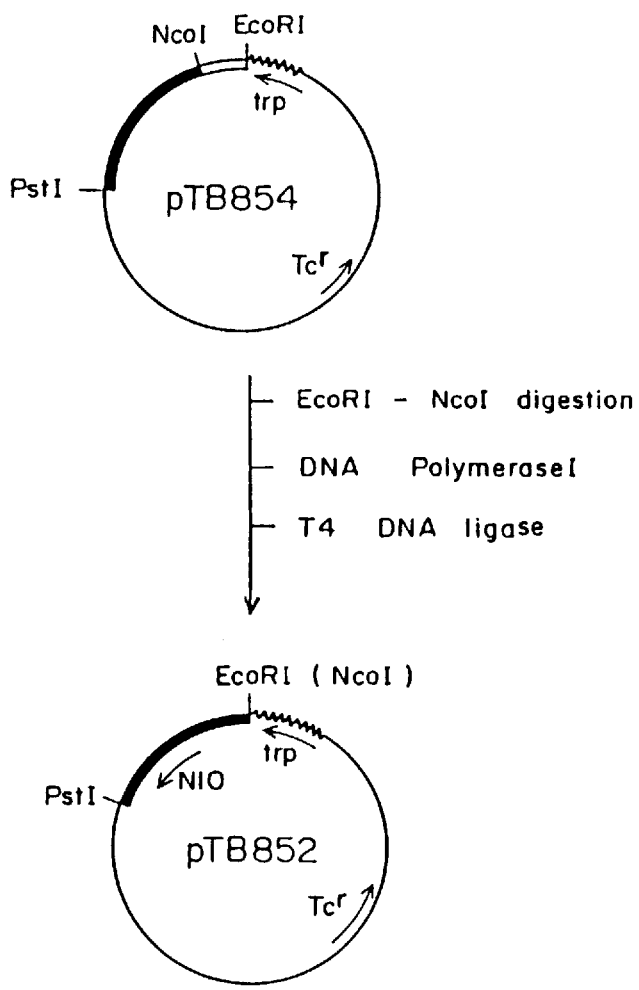
FIG. 47 shows the construction scheme of the plasmid pTB852 in Example 33.

(1) Construction of Plasmid pTB852 for Human bFGF Mutein Expression:

The DNA of the plasmid pTB854 which was obtained in the above Example 32 was cleaved with restriction enzymes EcoRI and NcoI so as to remove the DNA fragment which encodes the 10 amino acid residues of N terminus of the human bFGF. The single stranded portion of the remaining DNA fragment was sealed to blunt end by the use of *Escherichia coli* DNA polimerase I in the presence of dATP, dCTP, dGTP, dTTP, and was ligated by employing T4DNA ligation reaction to construct the plasmid pTB852 for human bFGF mutein (FIG. 47).

Using this plasmid 852, *Escherichia coli* MM294 was transformed, whereby the strain *Escherichia coli* MM294/pTB852, which harboring the plasmid pTB852 having the mutein-encoding gene shown in FIG. 48.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB852 thereby tested exhibited FGF activity. The mutein N10, in which the amino acid sequence of from Pro at the 2-position to Ser at the 10-position of human bFGF had been deleted, was thus obtained.

EXAMPLE 34

(Expression in *Escherichia coli* of Gene which Encodes Human bFGF Mutein)

Figure 49:
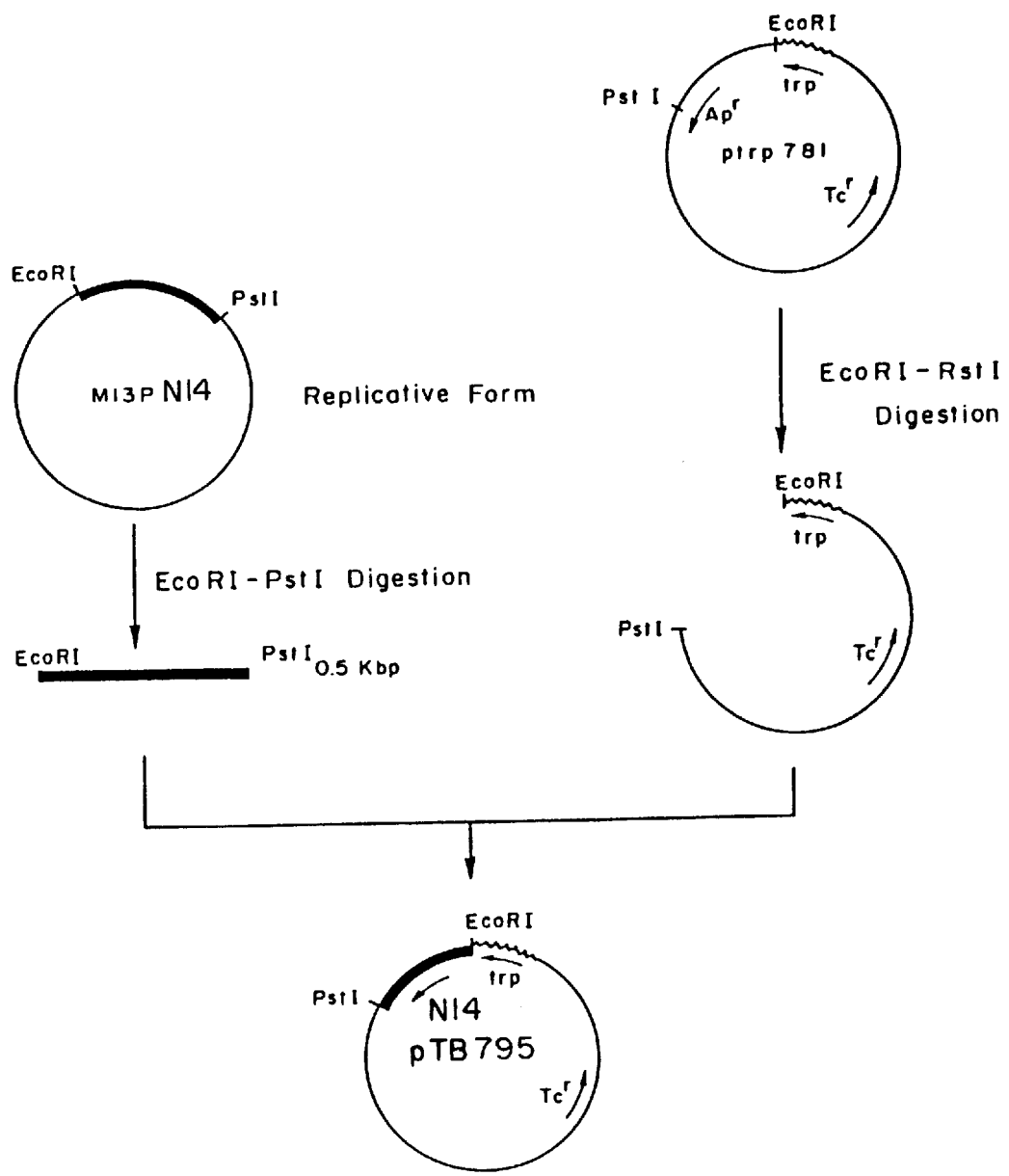
FIG. 49 shows the construction scheme of the plasmid pTB795 in Example 34.

(1) Construction of the Plasmid pTB795 for Human bFGF Mutein Expression:

The M13-PN14 replicative form (RF) obtained in Example 27 above was treated in the manner described in Example 2 (1) to construct the plasmid pTB795 for human bFGF mutein (FIG. 49).

Using this plasmid pTB795, *Escherichia coli* MM294 was transformed, whereby the strain *Escherichia coli* MM294/pTB795 (IFO 14700, FERM BP-1660) was obtained, which contains the plasmid pTB795 containing the mutein-encoding gene shown in FIG. 40.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB795 thereby tested exhibited FGF activity. The mutein N14, in which the amino acid sequence of from Pro at the 2-position to Pro at the 14-position of human bFGF had been deleted, was thus obtained.

EXAMPLE 35

(Expression in *Escherichia coli* of Gene which Encodes Human bFGF Mutein)

Figure 50:
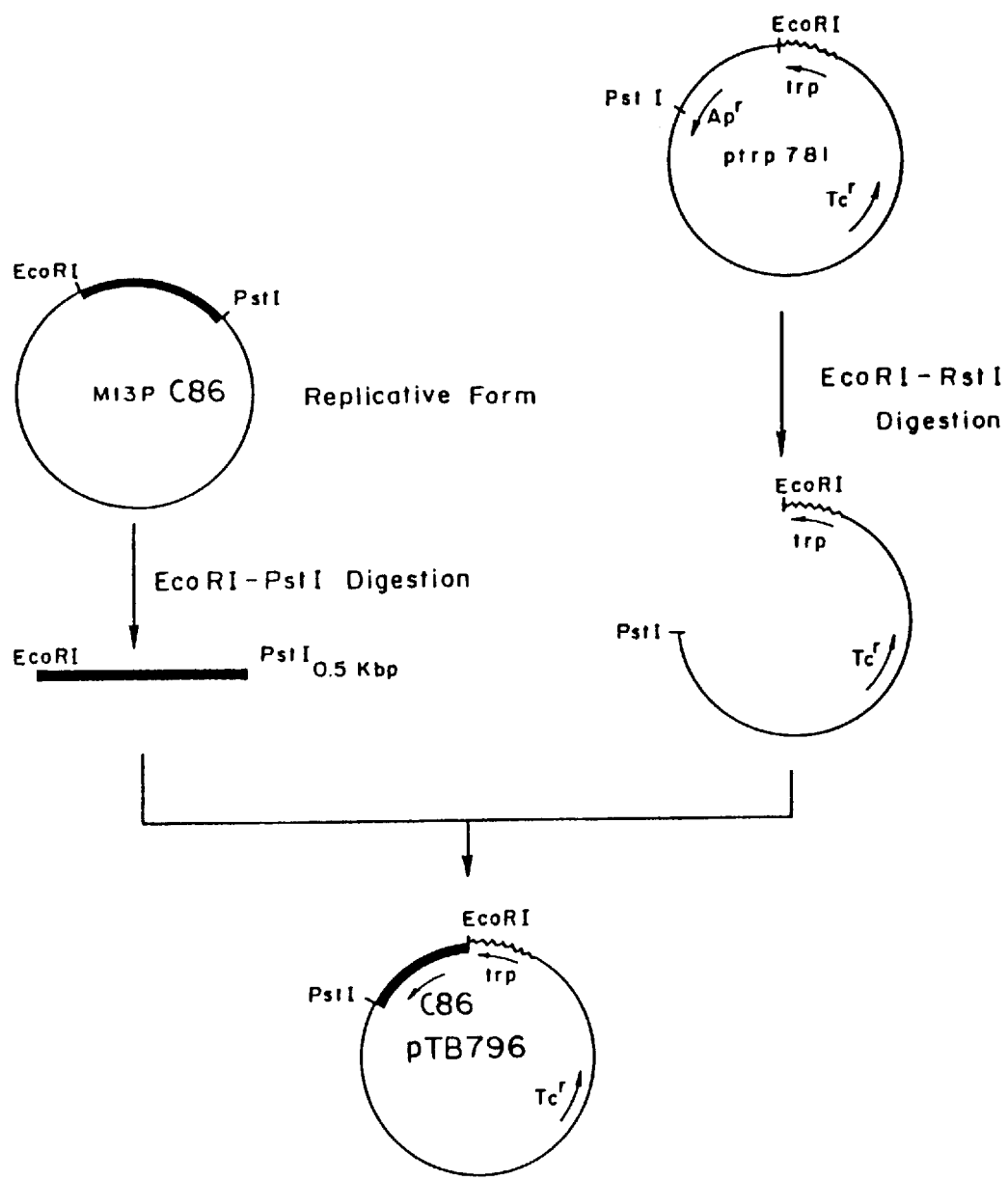
FIG. 50 shows the construction scheme of the plasmid pTB796 in Example 35.

(1) Construction of the Plasmid pTB796 for Human bFGF Mutein Expression:

The M13-PC86 replicative form (RF) obtained in Example 27 above was treated in the manner described in Example 2 (1) to construct the plasmid pTB796 for human bFGF mutein (FIG. 50).

Using this plasmid pTB796, *Escherichia coli* MM294 was transformed, whereby the strain *Escherichia coli* MM294/pTB796 (IFO 14701, FERM BP-1661) was obtained, which contains the plasmid pTB796 containing the mutein-encoding gene shown in FIG. 41.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

The cell extract obtained in the above (2) was subjected to an enzyme immunoassay (EIA), sandwich method, using monoclonal antibody as shown below (a) to (j).

As a result, it is confirmed that bFGF mutein C86 is present in the cell extract. The mutein C86, in which the amino acid sequence of from Lys at the 87-position to Ser at the 147-position had been deleted, was thus obtained.

Said EIA using monoclonal antibody was carried out by the following method:

(a) Immunization:

BALB/c mice (female, 4-week old) had the antigen human bFGF (as obtained in Reference Example 2) in solution in 0.4 ml of Freund's complete adjuvant (Difco Laboratories, USA) injected intraperitoneally. Three weeks later, 10 μg of the antigen hbFGF in solution in 0.4 ml of Freund's incomplete adjuvant was intraperitoneally administered. 3 weeks later, the same additional immunization was carried out, and, two weeks later, 10 μg of human bFGF in solution in physiological saline was intraperitoneally inoculated.

(b) Cell Fusion:

From the immunized mice mentioned in said (a), the spleen was excised 4 days after final antigen challenge to thereby obtain cells to be used for cell fusion. These cells were suspended in a medium prepared by mixing together Isokov medium and Ham F-12 medium in a ratio of 1:1 (hereinafter referred to as IH medium).

The mouse myeloma cell P3-X63-Ag 8UI was subcultured in RPMI 1640 medium containing 10% fetal bovine serum under an atmosphere of 5% carbon dioxide and 95% air.

Cell fusion was conducted in accordance with the method established by Köhler and Milstein [Köhler, G. and Milstein, C.: Nature, 256, 495 (1975)]. $2.9 \times 10^7$ cells of the above myeloma cell line and $1.5 \times 10^8$ immunized lymphocytes obtained by the above-mentioned method were mixed together and centrifuged, and 45% polyethylene glycol 6000 (hereinafter referred to as PEG 6000) in solution in 0.3 ml of IH medium was dropwise added. The PEG 6000 solution was preheated to 37° C., and was gradually added. Five minutes later, the 37° C.-preheated IH medium was added at a rate of 0.5 ml per minute to make 10 ml. The solution was then centrifuged at room temperature at 600 rpm for 15 minutes, and the supernatant was removed. This cell precipitate was suspended in 200 ml of IH medium containing 20% calf serum, and this suspension was transferred to a 24-well microplate (Linbro) in an amount of 2 ml per well. One day later, IH medium (containing 20% calf serum) supplemented with HAT ($1 \times 10^{-4}$M hipoxanthine, $4 \times 10^{-7}$M aminopterin, $1.6 \times 10^{-5}$M thymidine) (hereinafter referred to as HAT medium) was added to the microplate in an amount of 1 ml per well, and, a further three days later, one half amount of the medium was replaced with HAT medium. The cells thus grown are hybrid cells.

(c) Search for Antibody-Producing Cells:

Previously, the hybrid cell culture supernatant was added in an amount of 100 μl per well to a 96-well microtiter plate made of polystyrene which had had human bFGF immobilized thereto, and incubation was carried out at room temperature for 2 hours. The incubation supernatant was removed, and, after washing, the horse radish peroxidase (HRP)-labeled anti-mouse IgG goat antibody (Miles Laboratories) was added as the secondary antibody, and incubation was carried out at room temperature for 2 hours. The secondary antibody was removed, and, after thoroughly washing the wells, coloring reaction was carried out in the presence of added reaction substrate (EIA method). By this method potent valency was observed in 3 wells.

(d) Cloning of Hybrid Cells:

Cells in each of these three cells were sown to 0.5 cell per well to a 96-well microtiter plate which had had $10^4$ cells/well mouse thymocytes as vegetative cells sown thereon, and cloning was carried out. As a result, three clones, namely the mouse hybridoma HbF52 (IFO 50143) and the mouse hybridoma HbF78 (IFO 50144) were obtained.

(e) Ascitization of Hybrid Cells:

$2 \times 10^6$ cells of each of the mouse hybridoma HbF52 or the mouse hybridoma HbF78 was inoculated to mice which had had mineral oil previously administered intraperitoneally. Ten days later, ascites in an amount of 2 ml was collected from each mouse, whereby the monoclonal antibody MoAb52 and the monoclonal antibody MoAb78 were respectively obtained.

(f) Thus obtained monoclonal antibody MoAb 78 was subjected to purification from ascites fluid in accordance with the method of Stachelin et al. The Journal of Biological Chemistry, 256, 9750 (1981). Thus obtained antibody was concentrated to more than 2 mg/ml, and subjected to dialysis in 0.2M sodium phosphate buffer (pH 7.0). To thus obtained 1.4 ml solution of MoAb 78 (concentration 2.8 mg/ml), 50 μl of S-acetylmercaptosuccinic anhydride (Aldrich Co., U.S.A) dissolved in N, N'-dimethylformamide was added so as to reach the concentration of 11.5 mg/ml. The air in the reaction vessel is replaced by nitrogen gas. The vessel was sealed, and subjected to stirring so as to cause the reaction of introducing SH group. The unreacted S-acetylmercaptosuccinic acid anhydride was inactivated by the treatment for 10 minutes with 130 μl of 0.2M Tris.HCl (pH 7.0), 13 μl of 0.2M EDTA and 130 μl of 2M hydroxyamine (pH 7.0). The MoAb 78 was recovered by gel filtration using a column packed with Sephadex G-25 (diameter 1 cm×80 cm, Farmacia, Sweden) (flow rate: 20 ml/hour).

(g) 10 mg of horse radish peroxidase (HRP, Behringer Manheim, Grade I, West Germany) was dissolved in 1.4 ml of 0.1M phosphate buffer (pH 6.8). On the other hand, 14 mg of N-hydroxysuccinimide ester of N-(4-corboxy cyclohexyl methyl) maleimide was dissolved in 335 μl of DMF, and 100 μl of thus obtained solution was added to the HRP solution above mentioned. The air in the reaction vessel was replaced by nitrogen gas, and the vessel was sealed. After 1 hour reaction at room temperature, proteins of the portion of HRP introduced with maleimide group were recovered by gel filtration using a colomn packed with Sephadex G-25 as in the above (f).

(h) 6 ml of the portion of the monoclonal antibody MoAb 78 introduced with SH group obtained in the above (f) and 2 ml of the portion of HRP introduced with maleimide group obtained in the above (g) were mixed, and the mixture was concentrated to 1 ml using collodion bag (Sartorius, West Germany) under reduced pressure at 4° C. for 20 hours. After the reaction, the unreacted HRP introduced with SH group was removed with the use of Ultrogel AcA44 (LKB Co., diameter 1 cm×80 cm, Sweden) column (flow rate: 10 ml/hour). In the eluates, the fraction containing 2.4 HRP/antibody has the most high HRP number per antibody molecule. The product thus obtained was employed in the EIA in the following item (i).

(i) The monooclonal antibody MoAb 52 obtained in the above (e) was purified by the manner described in the above (f). The monoclonal antibody MoAb 52 was diluted with PBS so as to be 10 μg/ml or 20 μg/ml, and the diluent was poured into Immunoplate (Nunc. Denmark) so as to be 100 μl/well. The plate was kept standing at 4° C. overnight to adsorbe the monoclonal antibody MoAb 52 to the plate. After removing the antibody which is not adsorbed, the plate was washed with PBS thrice, PBS containing 0.01% merthiolate and 1% bovine serum albumin (BSA) was added to the plate at 200 μl/well, and the plate was kept standing at 4° C. overnight.

j) The cell extract containing bFGF mutein C86 obtained in the above (2) was diluted with PBS containing 0.1% BSA. From the plate obtained in the above (i), BSA solution was removed, the plate was washed with PBS four times, and the diluted bFGF mutein C86 was added to the plate so as to be 100 μl/well to adsorbe to the plate at 4° C. overnight. The unreacted mutein C86 was removed, and the plate was washed with PBS four times. The monoclonal antibody conjugated with HRP obtained in the above (h) was diluted with PBS containing 0.1% BSA to 1/300, and the diluent was added to the plate so as to be 100 μl/well. The reaction was carried out for 4 hours at room temperature. After removing the antibody, the plate was washed with PBS for 6 times, substrate for oxidase (Bio. Rad Co. U.S.A) was added to the plate so as to be 100 μl/well. Quantification was accomplished by absorbance measurements at 415 nm, and it was confirmed that a small amount of the mutein C86 was produced.

EXAMPLE 36

(Expression in *Escherichia coli* of Gene which Encodes Human bFGF Mutein)

Figure 51:
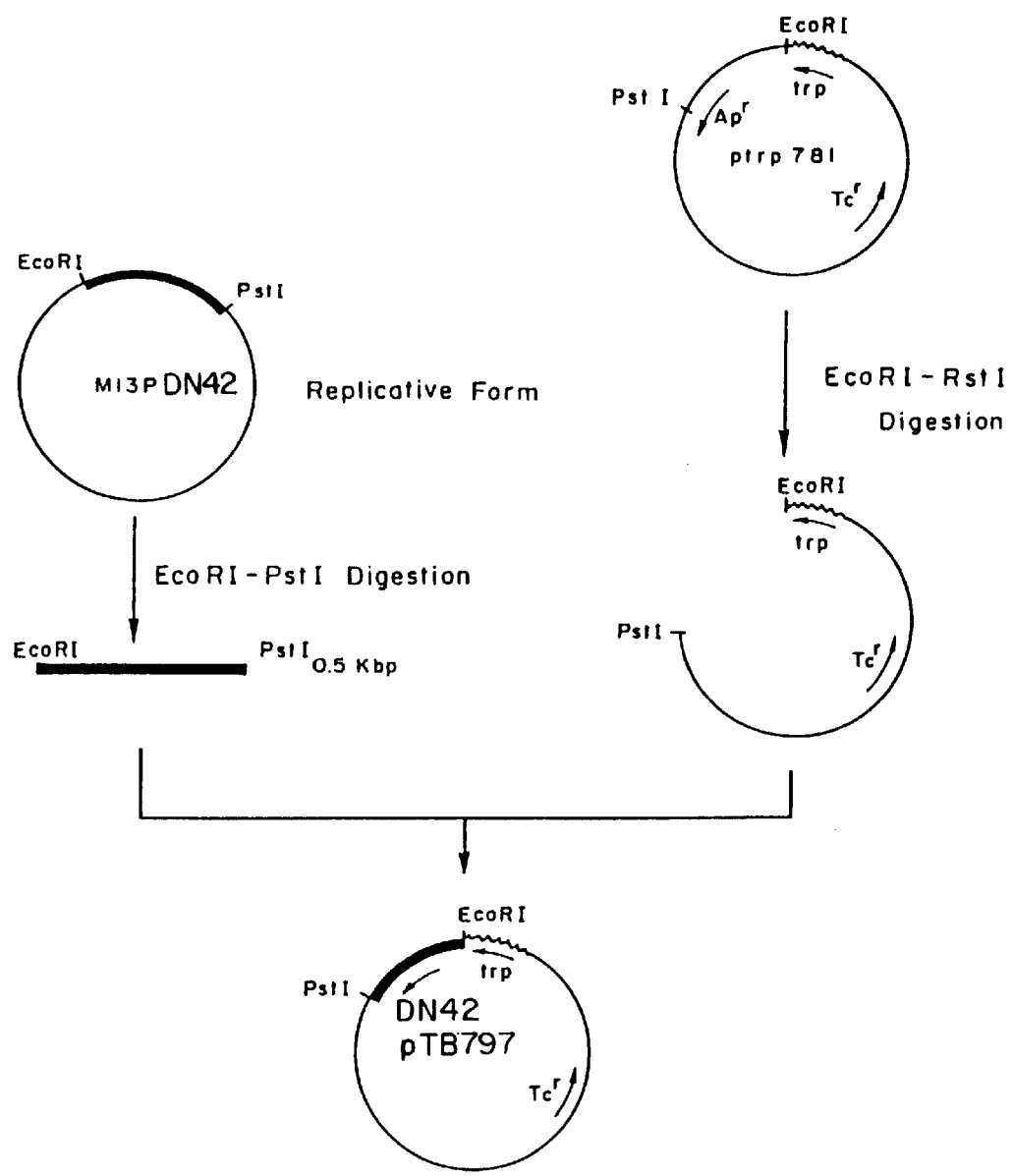
FIG. 51 shows the construction scheme of the plasmid pTB797 in Example 36.

(1) Construction of the Plasmid pTB797 for Human bFGF Mutein Expression:

The M13-PDN42 replicative form (RF) obtained in Example 27 above was treated in the manner described in Example 2 (1) to construct the plasmid pTB797 for human bFGF mutein (FIG. 51).

Using this plasmid pTB797, *Escherichia coli* MM294 was transformed, whereby the strain *Escherichia coli* MM294/pTB797 (IFO 14702, FERM BP-1662) was obtained, which harbors the plasmid pTB797 containing the mutein-encoding gene shown in FIG. 42.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB797 thereby tested exhibited FGF activity. The mutein DN42, in which Asp at the 42-position of human bFGF had been replaced by Asn, was thus obtained.

EXAMPLE 37

(Expression in *Escherichia coli* of Gene which Encodes Human bFGF Mutein)

Figure 52:
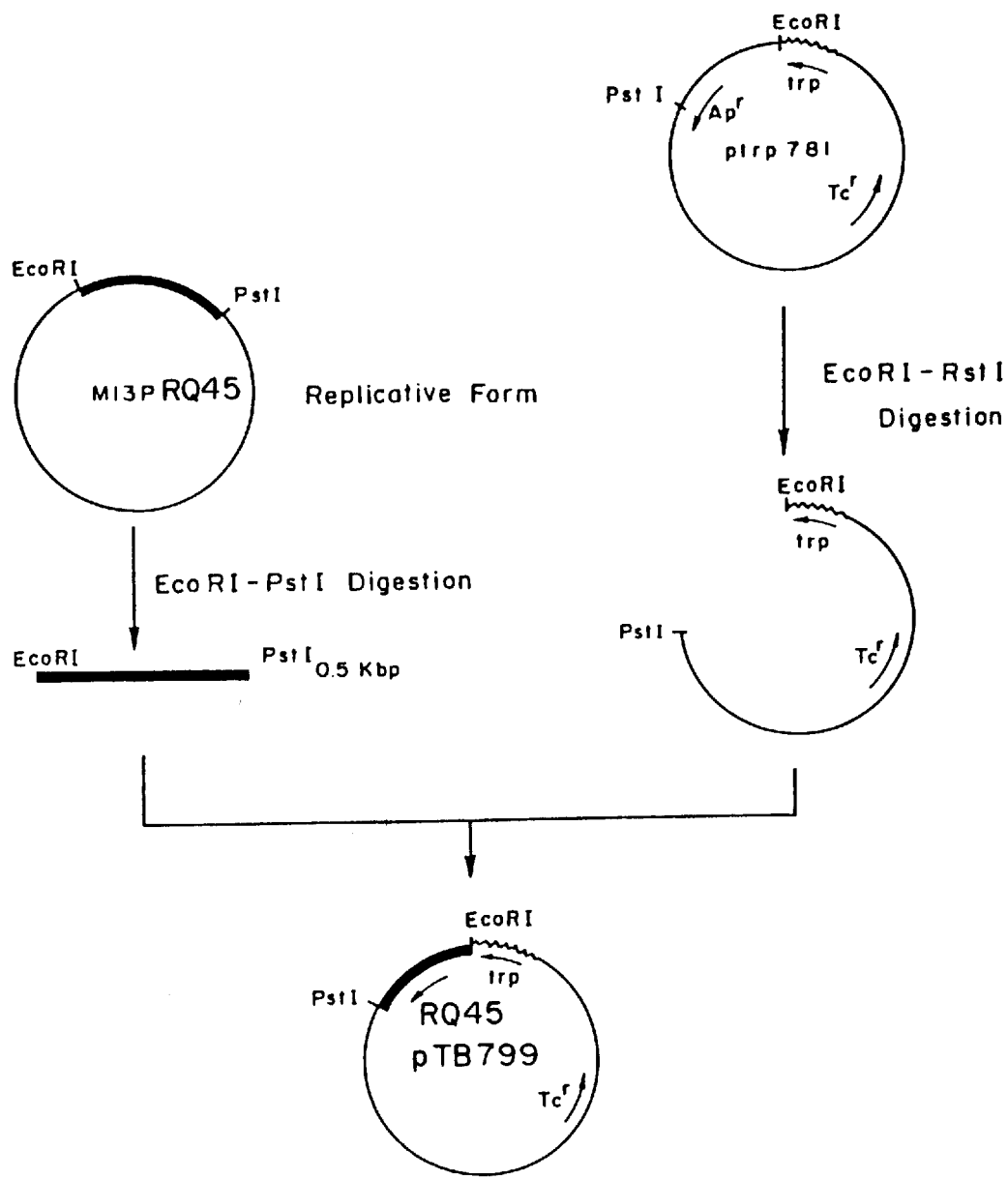
FIG. 52 shows the construction scheme of the plasmid pTB799 in Example 37.

(1) Construction of the Plasmid pTB799 for Human bFGF Mutein Expression:

The M13-PRQ45 replicative form (RF) obtained in Example 27 above was treated in the same manner as in Example 2 (1) to construct the plasmid pTB799 for human bFGF mutein (FIG. 52).

Using this plasmid pTB799, *Escherichia coli* MM294 was transformed, whereby the strain *Escherichia coli* MM294/pTB799 was obtained, which harbors the plasmid pTB799 containing the mutein-encoding gene shown in FIG. 43.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB799 thereby tested exhibited FGF activity. The mutein RQ45, in which Arg at the 45-position of human bFGF had been replaced by Gln, was thus obtained.

EXAMPLE 38

(Expression in *Escherichia coli* of Gene which Encodes Human bFGF Mutein)

Figure 53:
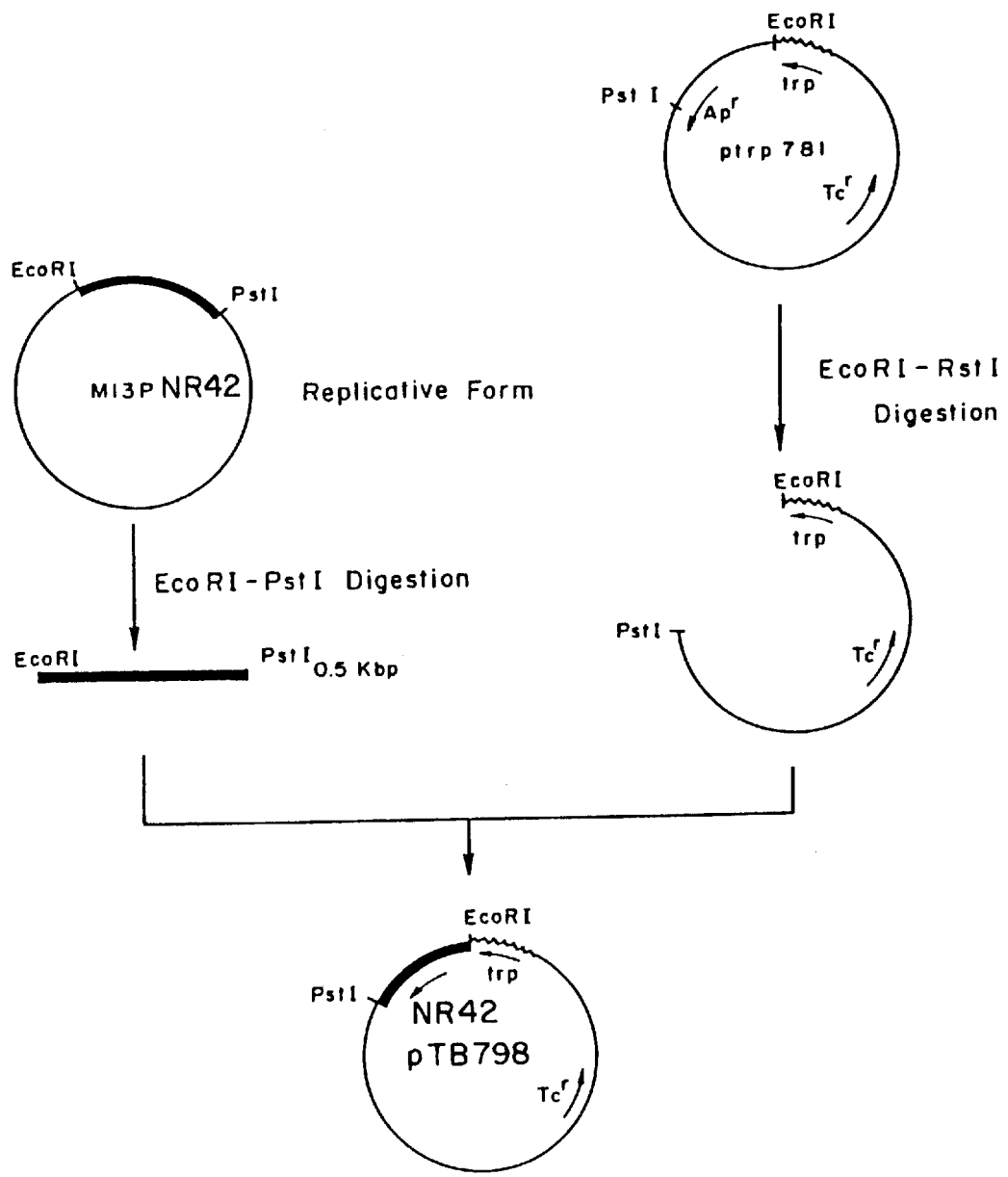
FIG. 53 shows the construction scheme of the plasmid pTB798 in Example 38.

(1) Construction of the Plasmid pTB798 for Human bFGF Mutein Expression:

The M13-PNR42 replicative form (RF) obtained in Example 28 above was treated in the manner described in Example 2 (1) to construct the plasmid pTB798 for human bFGF mutein (FIG. 53).

Using this plasmid pTB798, *Escherichia coli* MM294 was transformed, whereby the strain *Escherichia coli* MM294/pTB798 was obtained, which harbors the plasmid pTB798 containing the mutein-encoding gene shown in FIG. 44.

(2) Preparation of Bacterial Cell Extract:

The above-mentioned transformant was cultured by the method described in Example 2 (2) to give a supernatant, which was then used as a bacterial cell extract.

(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB798 thereby tested exhibited FGF activity. The mutein NR42, in which Asp at the 42-position of human bFGF had been replaced by Arg, was thus obtained.

EXAMPLE 39

(Production of Recombinant DNAs having Mutein-Encoding Base Sequence)

(1) Site-Specific Mutagenesis:

In the presence of 0.1 mM adenosine triphosphate (ATP), 50 mM hydroxymethylaminomethane hydrochloride (Tris-HCl) having a pH-value of 8.0, 10 mM $MgCl_2$, 5 mM dithiothreitol (DTT) and 9 units of T4 kinase, in a total amount of 50 μl, 40 picomoles of the synthetic oligonucleotide:

5'-TCTTCTCCAGGGATCCGTT-3'

[primer for adding the recognition site for the restriction enzyme BamHI in the base sequence and subsequently changing Val-44 to Ser and Arg 45 to Leu (see FIG. 38 (7))] was treated with T4 kinase at 37° C. for 1 hour. This kinase-treated primer was heated at 67° C. for 5 minutes, and at 42° C. for 25 minutes, in 50 μl of a mixture containing 50 mM NaCl, 1.0 mM Tris-HCl having a pH-value of 8.0, 10 mM $MgCl_2$ and 10 mM β-mercaptoethanol, whereby it was hybridized to 5 μg of the single-stranded (ss) M3-PDN 42 DNA. The annealed mixture was then cooled on ice, and was added to 50 μl of a reaction mixture containing 0.5 mM deoxynucleotide triphosphate (dNTP), 80 mM Tris-HCl having a pH-value of 7.4, 8 mM $MgCl_2$, 100 mM NaCl, 9 units of DNA polymerase I Klenow fragment, 0.5 mM ATP and 2 units of T4 DNA ligase, and reaction was carried out at 37° C. for 3 hours, and at 25° C. for 2 hours, whereafter the reaction was stopped by adding 2 μl of EDTA. The reaction product was used to transform infectable JM 105 cells; the transformant cells were allowed to grow overnight, whereafter an ssDNA was isolated from the culture medium supernatant. Using this ssDNA as a template for the 2nd cycle of primer elongation, gel-purified RF-type DNA was transformed into infectable JM 105 cells; the resulting transformant cells were spread over an agar plate, and were cultured overnight to obtain phage plaques.

(2) Screening and Identification of Plaques made Mutagenic:

Plates containing M13-PDN42 phage plaques mutated by the method of Example 27 using said synthetic oligomer (oligonucleotide) [FIG. 38 (7)] and 2 plates containing unmutated M13-PDN42 phage plaques obtained in Example 26 were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl having a pH-value of 7.5 and 1.5M NaCl. The filters were twice washed on filters immersed in 2×SSC (standard sodium citrate) in the same manner, and were allowed to dry, and this was followed by drying at 80° C. for 2 hours in a vacuum oven. The overlapped filters were subjected to prehybridization at 55° C. for 4 hours with 10 ml/filter of a DNA hybridization buffer solution (5×SSC)

having a pH-value of 7.0 containing 4 ×Denhardt's solution (polyvinylpyrrolidone, Ficoll and bovine serum albumin, 1×=0.02%), 0.1% sodium dodecyl sulfate (SDS), 50 mM sodium phosphate-buffered solution having a pH-value of 7.0 and 100 μg/ml denatured salmon sperm DNA. Hybridization was carried out at 42° C. for 24 hours with $10^5$ cpm/ml of an oligonucleotide primer. Each filter was washed in a buffer solution containing 0.1% SDS and a reduced amount of SSC at 50° C. for 30 minutes. The filters were then first washed with a buffer solution containing 2×SSC; the control filters, which contained unmutated M13-PDN42 plaques were examined for radioactivity using a Geiger counter. While stepwise reducing SSC concentration, the control filters, which contained unmutated M13-PDN42 plaques, were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-PDN42 plaques and 100 unmutated control plaques by means of an oligonucleotide probe treated with kinase in the presence of $^{32}$P-γ-ATP. None of the control plaques hybridized to the probe, while 3 to 10 of the mutated M13-PDN42 plaques hybridized to the probe.

One of the mutated M13-PDN42 plaques was taken, and was inoculated to a JM105 culture medium. From the resulting supernatant an ssDNA was prepared, and from the bacterial cell pellets a double-stranded (ds)DNA was prepared. Analyses were made of the base sequence using an appropriate oligonucleotide primer and ssDNA.

As a result, it was confirmed that the GTC (Val-44) codon and CGG (Arg-45) codon had been changed to TCC (Ser) codon and CTG (Leu) codon, respectively.

Figure 55:
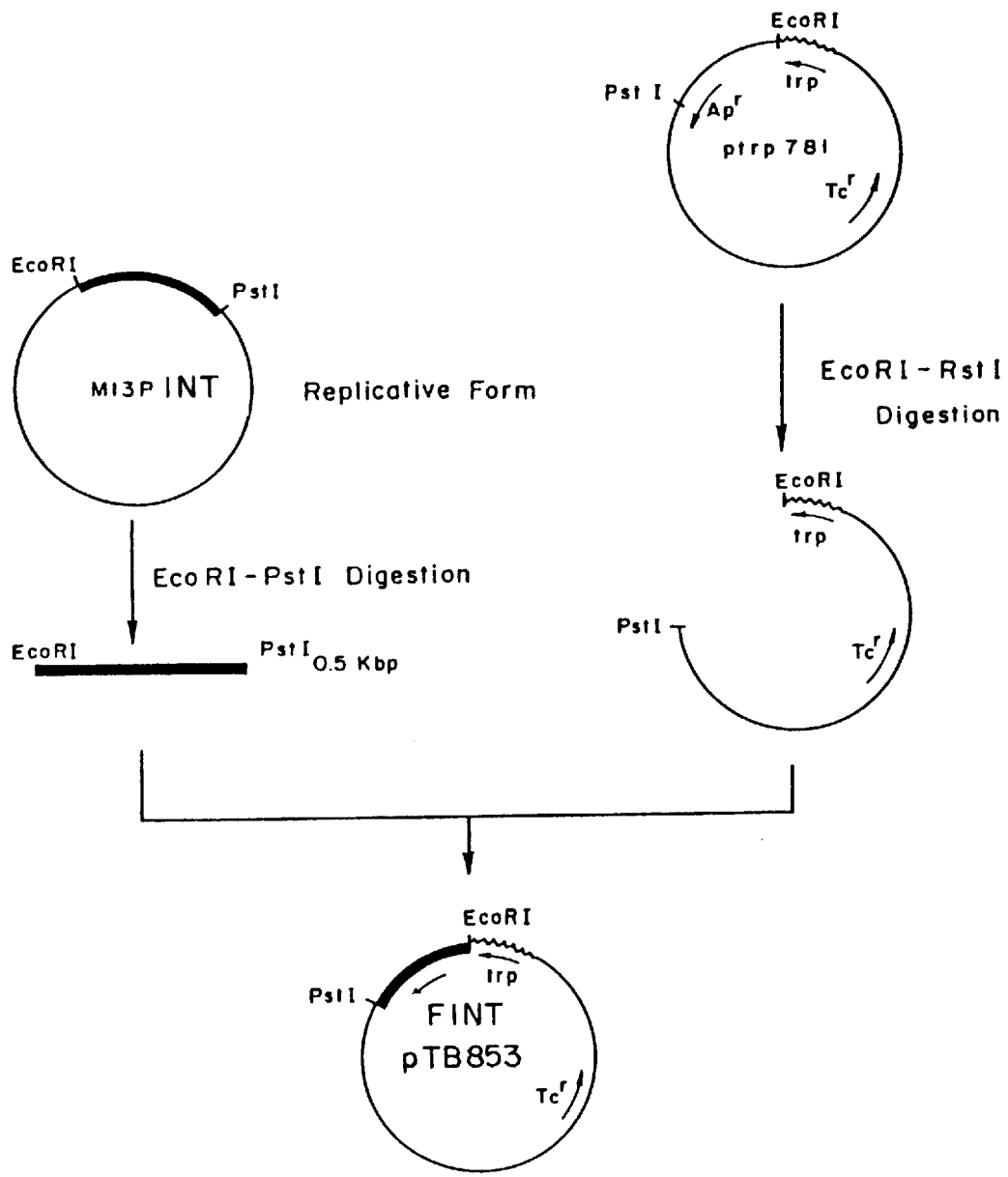
FIG. 55 shows the construction scheme of the plasmid pTB853 in Example 39.

Of the mutated M13-PDN42 phages, the phage in which Val-44 codon and Arg-45 codon had become Ser-encoding codon and Leu-encoding codon, respectively was named M13-PINT. Its base sequence and the amino acid sequence encoded thereby are shown in FIG. 54.
(3) Construction of the Plasmid pTB853 for Human bFGF Mutein Expression:

The M13-PINT replicative form (RF) obtained in the above (2) was treated in the manner described in Example 2 (1) to construct the plasmid pTB853 for human bFGF mutein (FIG. 55).

Using this plasmid pTB853, *Escherichia coli* MM294 was transformed, whereby the strain *Escherichia coli* MM294/pTB853 was obtained, which contains the plasmid pTB853 containing the mutein-encoding gene shown in FIG. 54.
(4) Preparation of Bacterial Cell Extract:

The above-mentioned transformant was cultured by the method described in Example 2 (2) to give a supernatant, which was then used as a bacterial cell extract.
(5) Human bFGF Activity of the Bacterial Cell Extract:

A determination was made of the human bFGF activity of the bacterial cell extract obtained in (4) above, by the method described in Example 2 (3).

The bacterial cell extract from *E. coli* MM294/pTB853 thereby tested exhibited FGF activity. The mutein FINT, in which Asp at 42-position, Val at 44-position and Arg at 45-position or human bFGF had been replaced by Asn, Ser and Leu, respectively, was thus obtained.

EXAMPLE 40

Figure 56:
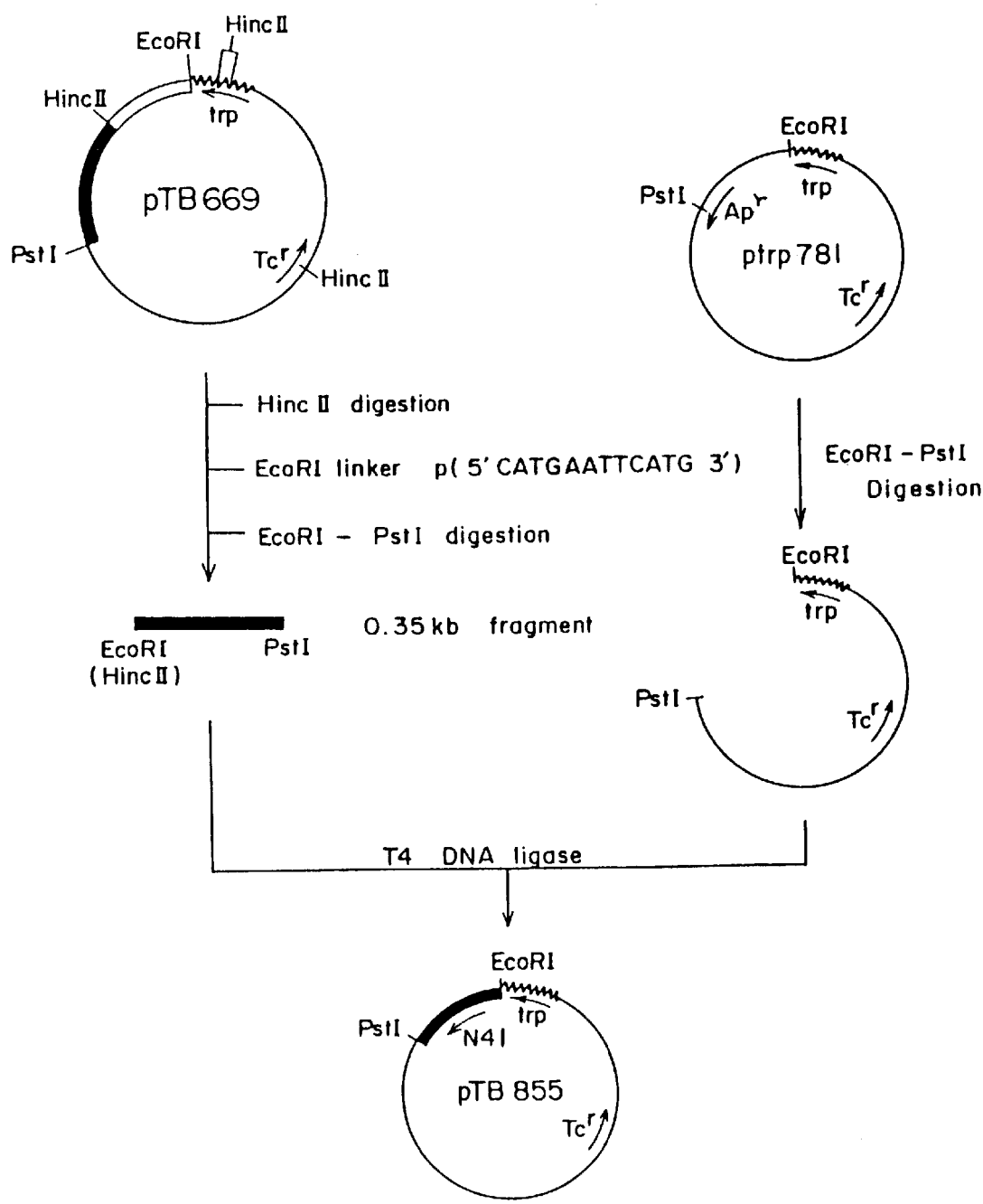
FIG. 56 shows the construction scheme of the plasmid pTB855 in Example 40.

(Expression in *Escherichia coli* of Gene which Encodes Human bFGF Mutein)
(1) Construction of the Plasmid pTB855 for Human bFGF Mutein Expression:

The DNA of the plasmid pTB669 which was obtained in the above mentioned Reference Example 2 was cleaved with a restriction enzyme HincII, and it was ligated with EcoRI linker p(5' CATGAATTCATG 3') under T4 DNA ligase reaction. Thus obtained DNA was further cleaved with a restriction enzymes EcoRI and PstI to recover a DNA fragment of about 0.35 kb. This DNA fragment was ligated with the about 3.2 kb DNA fragment obtained in Example 2 (1), the fragment being obtained by cleaving the plasmid ptrp781 with EcoRI-PstI, to obtain the plasmid pTB855 for human bFGF mutein expression was constructed (FIG. 56).

Using this plasmid 855, *Escherichia coli* MM294 was transformed, whereby the strain *Escherichia coli* MM294/pTB855, which contains the plasmid pTB855 having the mutein-encoding gene shown in FIG. 57.
(2) Preparation of Bacterial Cell Extract:

The above-mentioned transformant was cultured by the method described in Example 2 (2) to give a supernatant, which was then used as a bacterial cell extract.
(3) Human bFGF Activity of the Bacterial Cell Extract:

A determination was made of the human bFGF activity of the bacterial cell extract obtained in (2) above, by the method described in Example 2 (3).

The bacterial cell extract from *E. coli* MM294/pTB855 thereby tested exhibited FGF activity. The mutein N41, in which the amino acid sequence of from Pro at the 2-position to Val at the 41-position of human bFGF had been deleted, was thus obtained.

EXAMPLE 41

Figure 58:
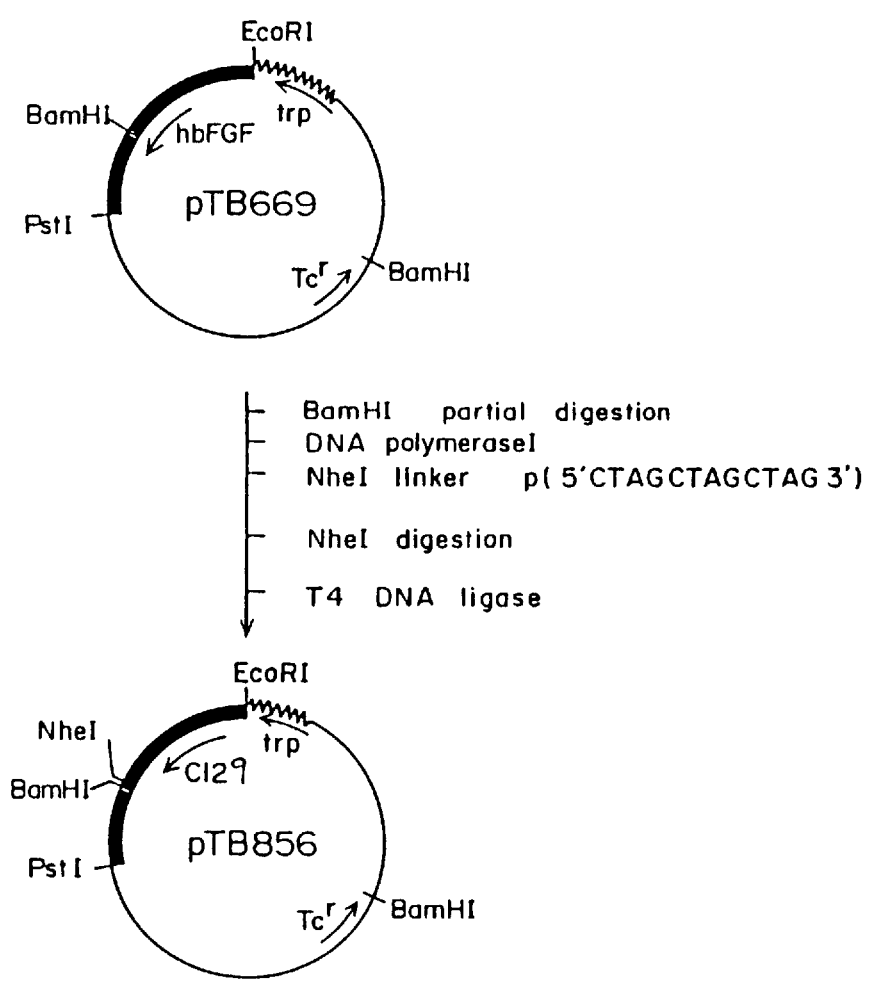
FIG. 58 shows the construction scheme of the plasmid pTB856 in Example 41.

(Expression in *Escherichia coli* of Gene which Encodes Human bFGF Mutein)
(1) Construction of the Plasmid pTB856 for Human bFGF Mutein Expression:

The DNA of the plasmid pTB669 which was obtained in the above mentioned Reference Example 2 was partly cleaved with a restriction enzyme BamHI so as to obtain BamHI recognition site in the bFGF gene. The site was further cleaved with *Escherichia coli* DNA polymerase I in the presence of dATP, dCTP, dGTP, dTTP to give blunt end. This DNA is ligated with NheI linker p(5'CTAGCTAGCTAG3') under T4 DNA ligase reaction. After treating with the restriction enzyme NheI and ligating the cleaved site under T4 DNA ligase reaction, the plasmid pTB856 for human bFGF mutein expression was constructed (FIG. 58).

Using this plasmid pTB856, *Escherichia coli* MM294 was transformed, whereby the strain *Escherichia coli* MM294/pTB856 which contains the plasmid pTB856 having the mutein-encoding gene shown in FIG. 59.
(2) Preparation of Bacterial Cell Extract:

The above-mentioned transformant was cultured by the method as in Example 2 (2) to give a supernatant, which was then used as a bacterial cell extract.
(3) The cell extract obtained in the above (2) was subjected to an enzyme immunoassay (EIA), sandwich method, as the manner described in Example 35 (3). As a result, it is confirmed that bFGF mutein is present in the cell extract. The mutein C129, in which the amino acid sequence of from Lys at the 130-position to Ser at the 147-position had been deleted, was thus obtained.

EXAMPLE 42

(Expression in Animal Cell of Gene which Encodes Human bFGF Mutein)
(1) Construction of the Plasmids pTB831, pTB833 and pTB835 for Human bFGF Mutein Expression:

The plasmid pTB762, which was obtained in Example 7 above mentioned, was cleaved with the restriction enzymes EcoRI-BamHI to obtain a 0.38 kb DNA fragment containing a coding region which encodes human bFGF mutein CS23, in which Cys at the 70-position and at the 88-position had been replaced by Ser.

On the other hand, the plasmid pTB504 [Example 1 (ii) of Japanese Patent Laid-open No. 62-175182 which corresponds to European Patent Publication No. 225, 701] was cleaved with the restriction enzyme ClaI-EcoRI to obtain a 1.7 kb DNA fragment containing murine leukemia virus (MuLV) LTR region, SV40 early promoter, splice junction and human interleukin-2 (IL-2) leader sequence.

Furthermore, the plasmid pTB627, which was obtained in Reference Example 1, was cleaved with the restriction enzyme ClaI-EcoRI to give 2 kb DNA fragment, and the plasmid pTB389 was cleaved with the restriction enzyme ClaI-EcoRI to give 2.6 kb DNA fragment. Thus obtained 2 kb DNA fragment and 2.6 kb DNA fragment was ligated to give the plasmid pTB675, which encodes human bFGF. The above plasmid pTB389 was obtained by converting each of the PstI cleavage site at the 5'-terminal region and the BamHI cleavage site at the 3'-terminal region of the interleukin-2 gene region of plasmid pTB106 (disclosed in Japanese Patent Laid-open No. 61-63282 which corresponds to European Patent Publication No. 172, 619) to EcoRI, to remove the interleukin-2 gene region. Then, the plasmid pTB675 was cleaved with the restriction enzymes ClaI-BamHI to give 3.4 kb DNA fragment which contains a coding region for amino acids at C-terminus of human bFGF, a non-coding region, ampicilline resistant gene originated from plasmid pBR322, and replication origin in *Escherichia coli*.

Figure 60:
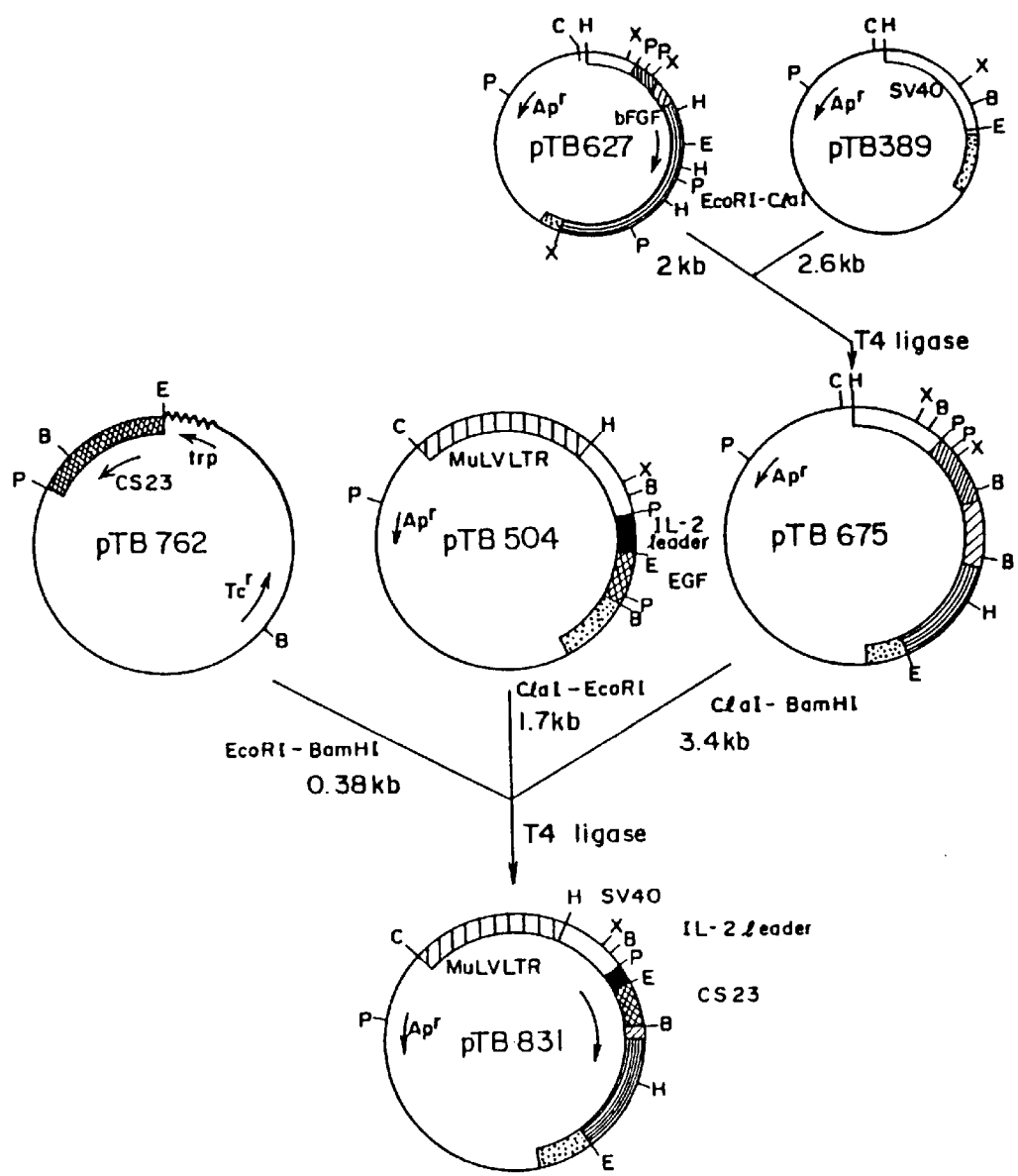
FIG. 60 shows the construction scheme of the plasmid pTB831 in Example 42.

The above three DNA fragments (i.e. 0.38 kb DNA fragment, 1.7 kb DNA fragment and 3.4 kb DNA fragment) were ligated by the use of T4 DNA ligase to give the plasmid pTB831 (FIG. 60).

Similarly, the plasmid pTB763 obtained in Example 18, which encodes the human bFGF mutein CS14 (in which Cys at the 26- and 93-positions of human bFGF had been replaced by Ser.) or the plasmid pTB765 obtained in Example 11, which encodes the human bFGF mutein CS 1234 (in which Cys at the 26-, 70-, 88- and 93-positions of human bFGF had been replaced by Ser.) was used instead of the plasmid pTB762 in the above procedure, whereby the plasmid pTB833 and the plasmid pTB835, respectively, were constructed.

(2) Expression in Animal Cells:

Monkey COS7 cells were seeded into tissue culture dishes of 6 cm diameter with DMEM medium containing 10% fetal calf serum, and after 24 hours the culture medium was replaced by a new one. After 4 hours, 10 μg DNA of the plasmid pTB831, pTB833 or pTB835 was transfected to the COS7 cells in accordance with calcium phosphate method [Graham et al. Virology, 52, 456 (1973)]. The next day the culture medium was replaced by DMEM medium containing 1% fetal calf serum. After 48 hours cultivation, cultured broth including cells was collected and cells were recovered. The cells were washed with PBS twice, and then suspended in PBS. The suspension was treated with ultrasonic treatment in a short time, and then subjected to centrifugation for 15 minutes at 15,000 rpm to give supernatant.

A determination of human bFGF activity was made on the cultured broth of COS7 cells infected with the plasmid and on the extract from the cells, by the method described in Example 2 (3). The results thus obtained are shown in Table 7.

TABLE 7

| Plasmid | Mutein | FGF Activity (ng/dish) | |
|---|---|---|---|
| | | Cultured broth | Extract from cells |
| pTB831 | CS23 | 115 | 420 |
| pTB833 | CS14 | 0.2 | 35 |
| pTB835 | CS1234 | 1.1 | 20 |
| — | | <0.02 | 1 |

EXAMPLE 43

(Human bFGF cDNA Deletion Reaction, Construction of Mutant, and Construction of Human bFGF Mutein Expression Plasmid)

From plasmid pTB669, obtained in Reference Example 2(1) described above, a portion corresponding to human bFGF cDNA was isolated using restriction enzymes EcoRI and BglII, and inserted into plasmid pTB891 [plasmid obtained by converting the Hind III site (multicloning site) of pUC118 (Vieira, J. and Messing J., Methods in Enzymology) (purchased by Takara Shuzo Co., Ltd., Japan) to a BglII site using BglII linker (CAGATCTG) (produced by Takara Shuzo Co., Ltd).] at the EcoRI-BamHI site to construct plasmid pTB904. Plasmid pTB904 thus obtained was cleaved with two restriction enzymes, namely XbaI and PstI, and subjected to ExoIII nuclease reaction and mungbean nuclease reaction using a kilo-sequence deletion kit (produced by Takara Shuzo Co., Ltd). The plasmid was then ligated with an NheI stop linker (produced by New England Biolabs U.S.A). and used to transform *Escherichia coli* MV1184 (see FIG. 61).

The mutants thus obtained were screened by DNA base sequencing; mutants having any modified portion which codes for the C-terminal of human bFGF were selected. These plasmid mutants were named pTB905 through 911. Their bFGF cDNA portion and bFGF mutein coded for thereby are shown in FIGS. 62 through 68, respectively. Plasmid pTB905 encodes rhbFGF mutein C101, which lacks amino acids at 102- to 147-positions of human bFGF (see FIG. 62). Plasmid pTB906 encodes rhbFGF mutein C105, which lacks amino acids at 106- to 147-positions of human bFGF (see FIG. 63). Plasmid pTB907 encodes rhbFGF mutein C114, which lacks amino acids at 115- to 147-positions of human bFGF (see FIG. 64). Plasmid pTB908 encodes rhbFGF mutein C118, which lacks amino acids at 119- to 147 positions of human bFGF (see FIG. 65). Plasmid pTB909 encodes rhbFGF mutein C123, which lacks amino acids at 124- to 147-positions of human bFGF (see FIG. 66). Plasmid pTB910 encodes rhbFGF mutein C129, which lacks amino acids at 130- to 147-positions of human bFGF (see FIG. 67). Plasmid pTB911 encodes rhbFGF mutein C137, which lacks amino acids at 139- to 147-positions of human bFGF and which has serine as the replacement for isoleucine at 138-position (see FIG. 68). Plasmids pTB905 through 911 were each cleaved with EcoRI-BglII, and the bFGF cDNA (modified) portion was isolated.

Figure 69:
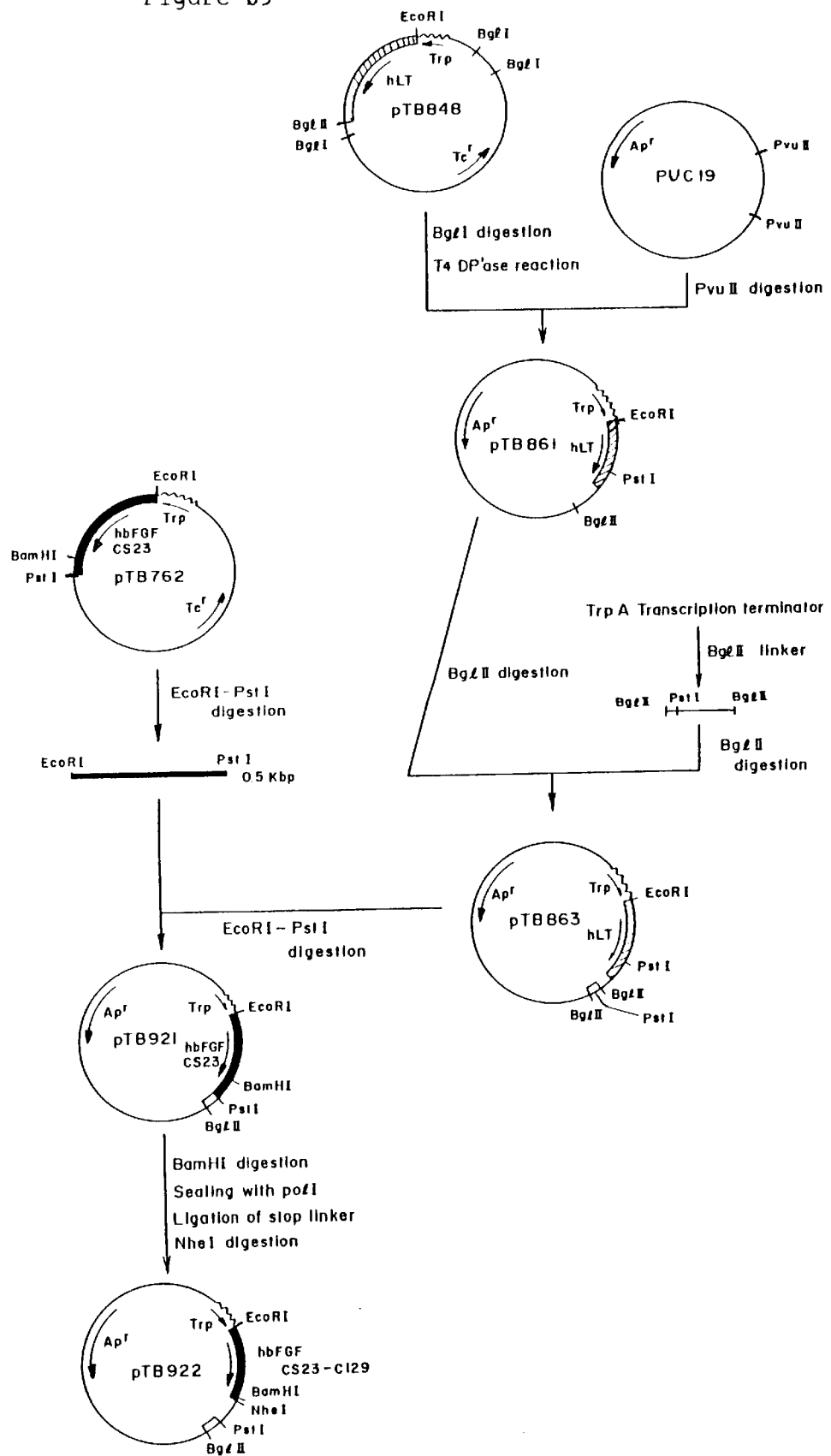
FIG. 69 shows the construction scheme of plasmid pTB861 obtained in Example 1 and plasmid pTB922 obtained in Example 44.
Figure 70:
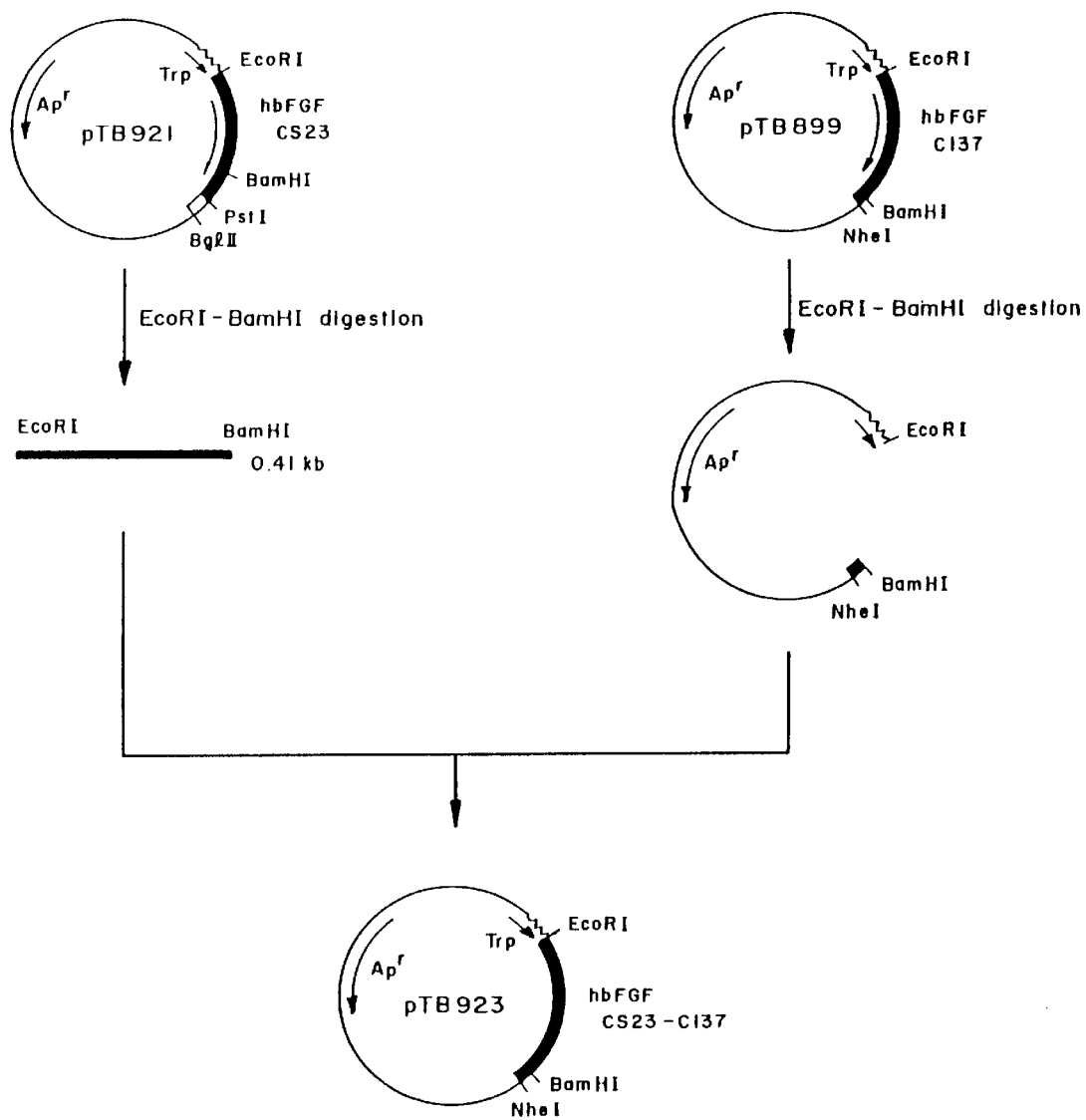
FIG. 70 shows the construction scheme of plasmid pTB923 obtained in Example 45.

A 1.2 kbp BglI DNA fragment containing the region which codes for lymphotoxin was cleaved off from plasmid pTB848, obtained as in Example 6 given in European Patent Publication No. 272, 894. The BglI fragment was subjected to T4 DNA polymerase reaction to make both ends blunt, after which it was inserted into plasmid pUC19 [Yanisch-Perron, C. et al., Gene, 33, 103–119 (1985); Messing, J., Methods in Enzymology, 101, 20–78 (1983)] (produced by Pharmacia, Sweden) at the PvuII site to construct plasmid pTB861 (FIG. 69).

Figure 61:
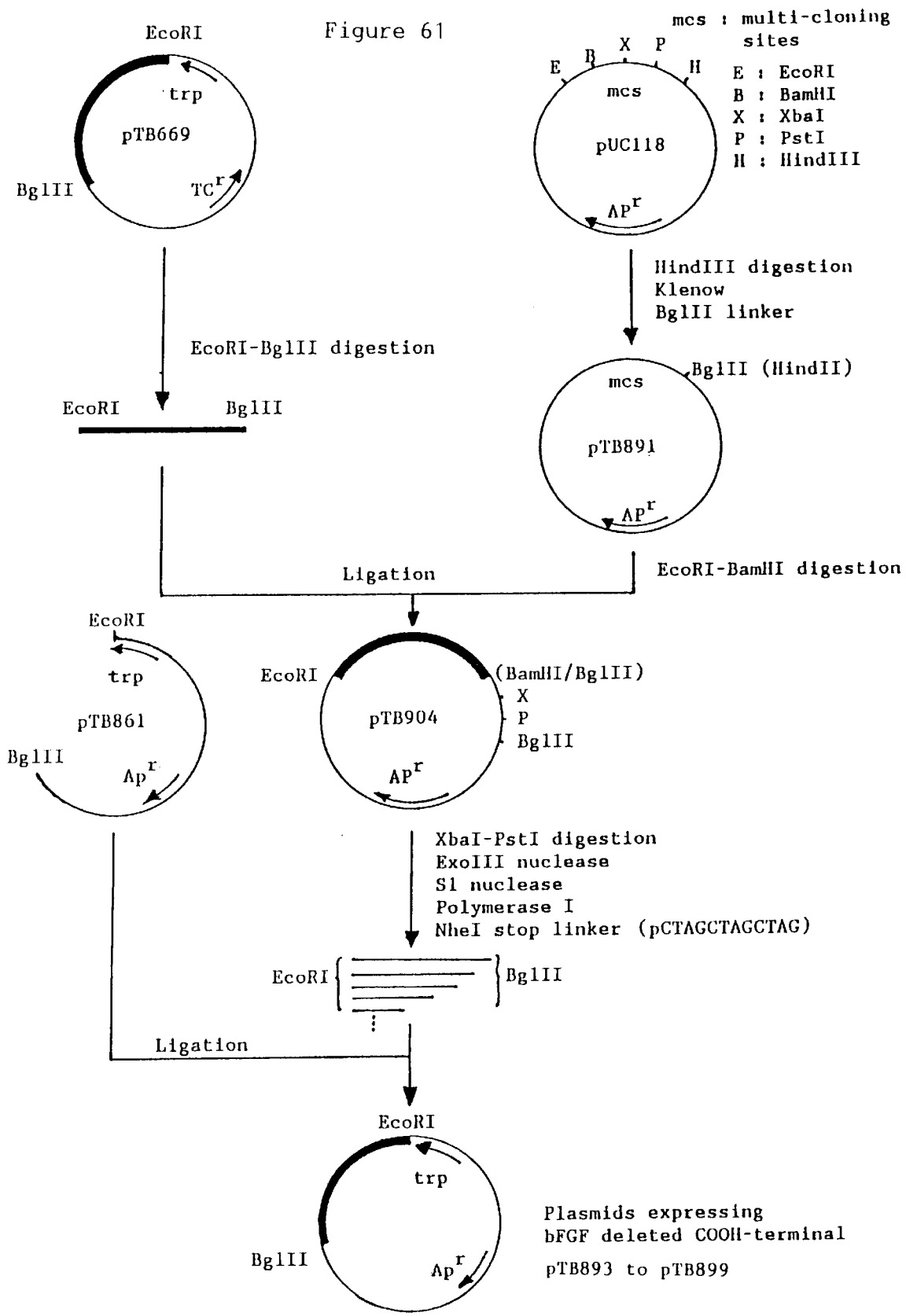
FIG. 61 shows the construction scheme of plasmids pTB905 through 911 obtained in Example 43.

The human bFGF cDNA (modified) portions obtained above were each inserted into the expression vector cleaved with EcoRI-BamHI from plasmid pTB861 obtained above to respectively yield plasmids pTB893, pTB894, pTB895, pTB896, pTB897, pTB898, and pTB899 (FIG. 61). Using these plasmids, E. coli MM294 was transformed to respectively yield the strains: E. coli MM294/pTB893 (IFO 14772, FERM BP-2009), which harbors plasmid pTB893 containing the gene encoding rhbFGF mutein C102, which lacks amino acids at 102- to 147-positions of human bFGF; E. coli MM294/pTB894, which harbors plasmid pTB894 containing the gene encoding rhbFGF mutein C105, which lacks amino acids at 106- to 147-positions of human bFGF; E. coli MM294/pTB895, which harbors plasmid pTB895 containing the gene encoding rhbFGF mutein C114, which lacks amino acids at 115- to 147-positions of human bFGF; E. coli MM294/pTB896, which harbors plasmid pTB896 containing the gene encoding rhbFGF mutein C118, which lacks amino acids at 119- to 147-positions of human bFGF; E. coli MM294/pTB897, which harbors plasmid pTB897 containing the gene encoding rhbFGF mutein C123, which lacks 124- to 147-positions of human bFGF; E. coli MM294/pTB898 (IFO 14773, FERM BP-2010), which harbors plasmid pTB898 containing the gene encoding rhbFGF mutein C129, which lacks amino acids at 130- to 147-positions of human bFGF; and E. coli MM294/pTB899 (IFO 14774, FERM BP-2011), which harbors plasmid pTB899 containing the gene encoding rhbFGF mutein C137, which lacks amino acids at 139- to 146-positions of human bFGF and which has serine as the replacement for isoleucine at 138-position.

EXAMPLE 44

(1) Construction of the Expression Plasmid

Trp A transcription terminator comprising 28 base pairs (produced by Pharmacia, Sweden)

$$\begin{pmatrix} \text{AGCCCGCCTAATGAGCGGGCTTTTTTT} \\ \text{TCGGGCGGATTACTCGCCCGAAAAAAAA} \end{pmatrix},$$

after being ligated with bglII linker

by T4 DNA Ligase, was digested with BglII and inserted into plasmid pTB861 as produced in Example 43 at the BglII site using T4 DNA ligase to construct plasmid pTB863. Separately, an EcoRI-PstI DNA fragment which codes for rhbFGF mutein CS23 was cleaved off from plasmid pTB762, obtained in Example 7, and was inserted into plasmid pTB863 at the EcoRI-PstI site to construct plasmid pTB921. This plasmid pTB921 was cleaved with BamHI and subjected to E. coli DNA polymerase I (Klenow enzyme) reaction to duplicate the single-strand portion. This DNA fragment was then ligated with translation termination linker

using T4 DNA ligase, after which it was trimmed with NheI and cyclized using T4 DNA ligase to construct plasmid pTB922 (see FIG. 69). This plasmid was used to transform E. coli MM294 to give E. coli MM294/pTB922 (IFO 14775, FERM BP-2012). This expression plasmid pTB922 expresses hbFGF mutein CS23C129, which is of rhbFGF mutein CS23 type and which lacks amino acid residues at 130- to 147-positions from the C-terminal.

(2) Preparation of Cell Extract

The above transformants was cultivated in M9 medium containing 1% glucose, 0.4% casamino acids and 8 μg/ml tetracycline. When the Klett value was about 200, 3-β-indolylacrylic acid was added to 25 μg/ml, and the cultivation was continued for further 4 hours. Thereafter, cells were harvested and suspended in one twentieth volume of 10% sucrose solution in 20 mM Tris-HCl, pH 7.6. To this suspension were added phenylmethylsulfonyl fluoride (PMSF) to 1 mM (final concentration), EDTA to 10 mM, NaCl to 0.1M, spermidine hydrochloride to 10 mM and lysozyme to 100 μg/ml. After allowing to stand at 0° C. for 45 minutes, the whole mixture was sonicated for 30 seconds. The sonication product was centrifuged at 18,000 rpm (Servall centrifuge, SS 34 roter, U.S.A). for 30 minutes to give a supernatant, which was used as the cell extract.

(3) rhbFGF Mutein Detected in Cell Extract rhbFGF mutein CS23C129 in the cell extract was detected by immunological method using monoclonal antibodies against humman bFGF in a manner of Example 35.

EXAMPLE 45

(1) Construction of Expression Plasmid pTB923

Plasmid pTB921 as obtained in Example 3 was digested with EcoRI and BamHI to give a 0.41 kb EcoRI-BamHI fragment, which was then inserted into plasmid pTB899, which expresses rhbFGF mutein C137, which lacks amino acid residues at 139- through 147-positions in the C-terminal and which has serine as the replacement for isoleucine at 138-position, at the EcoRI-BamHI site to construct plasmid pTB923 (see FIG. 12). Using this plasmid, E. coli MM294 was transformed to yield E. coli MM294/pTB923 (IFO 14776, FERM BP-2013).

Plasmid pTB923 expresses hbFGF mutein CS23C137, which is of mutein CS23 type and which lacks amino acid residues at 139- through 147-positions at the C-terminal and which has serine as the replacement for isoleucine at 138-position.

(2) Preparation of Cell Extract

The above transformants was cultivated in M9 medium containing 1% glucose, 0.4% casamino acids and 8 μg/ml tetracycline. When the Klett value was about 200, 3-β-indolylacrylic acid was added to 25 μg/ml, and the cultivation was continued for further 4 hours. Thereafter, cells were harvested and suspended in one twentieth volume of 10% sucrose solution in 20 mM Tris-HCl, pH 7.6. To this suspension were added phenylmethylsulfonyl fluoride (PMSF) to 1 mM (final concentration), EDTA to 10 mM, NaCl to 0.1M, spermidine hydrochloride to 10 mM and lysozyme to 100 μg/ml. After allowing to stand at 0° C. for 45 minutes, the whole mixture was sonicated for 30 seconds. The sonication product was centrifuged at 18,000 rpm (Servall centrifuge, SS 34 roter, U.S.A). for 30 minutes to give a supernatant, which was used as the cell extract.

(3) rhbFGF Mutein Detected in Cell Extract rhbFGF mutein CS23C129 in the cell extract was detected by immunological method using monoclonal antibodies against humman bFGF in the manner of Example 35.

EXAMPLE 46

(Bioactivities of the rhbFGF Mutein C129)

FGF activity of the bacterial cell extract of E. coli MM294/pTB856 obtained in Example 41 (2) was determined by the method described in Example 35 (3). The addition of the bacterial cell extract evidently promoted $^3$H-thymidine uptake of BALB/c3T3 cells in a stationary state.

The preparation purified from the bacterial cell extract by heparin affinity chromatography was also assayed for FGF activity in the manner as mentioned above; the rhbFGF mutein C129 exhibited an activity of 0.02 to 0.1, relative to that of FGF, taken as 1.

The preparation as mentioned above was also examined for effect on the proliferation of BALB/c3T3 cells. BALB/c3T3 cells were seeded to a 24-well plate at $10^4$ cells/well, each well holding a DMEM medium containing 5% FCS. The next day the medium was replaced by a DMEM medium containing 0.6% FCS with the above-mentioned preparation added simultaneously. After a 3-day cultivation, cells were counted using a Coulter counter. The results are shown in Table 8 shown below.

TABLE 8

| | rhb FGF mutein C129 | | | | |
|---|---|---|---|---|---|
| | 0 | 0.2 | 1 | 5 | 25 |
| Cells ($10^4$) | 3.30 | 5.08 | 6.23 | 6.77 | 8.17 |

As seen in the Table 8, rhbFGF mutein C129, at concentrations of 5 to 25 ng/ml, increased the cell count to 2 to 2.5 times the original levels. In addition, although bFGF causes noticeable morphological changes in BALB/c3T3 cells at concentrations of 0.5 to 1.0 ng/ml or more, no morphological logical changes occurred in BALB/c3T3 cells even when rhbFGF mutein C129 was added at 25 ng/ml.

EXAMPLE 47

(Production of Human bFGF Mutein C129 using a T7 Promoter)

(1) The DNA of the plasmid pTB898 obtained in Example 43, which carries the gene which codes for rhbFGF mutein C129, was digested with the restriction enzyme EcoRI; the single-stranded portion was digested by mung bean nuclease treatment to make both ends blunt, after which it was cleaved with the restriction enzyme BglII to give a fragment which codes for rhbFGF mutein C129.

Figure 73:
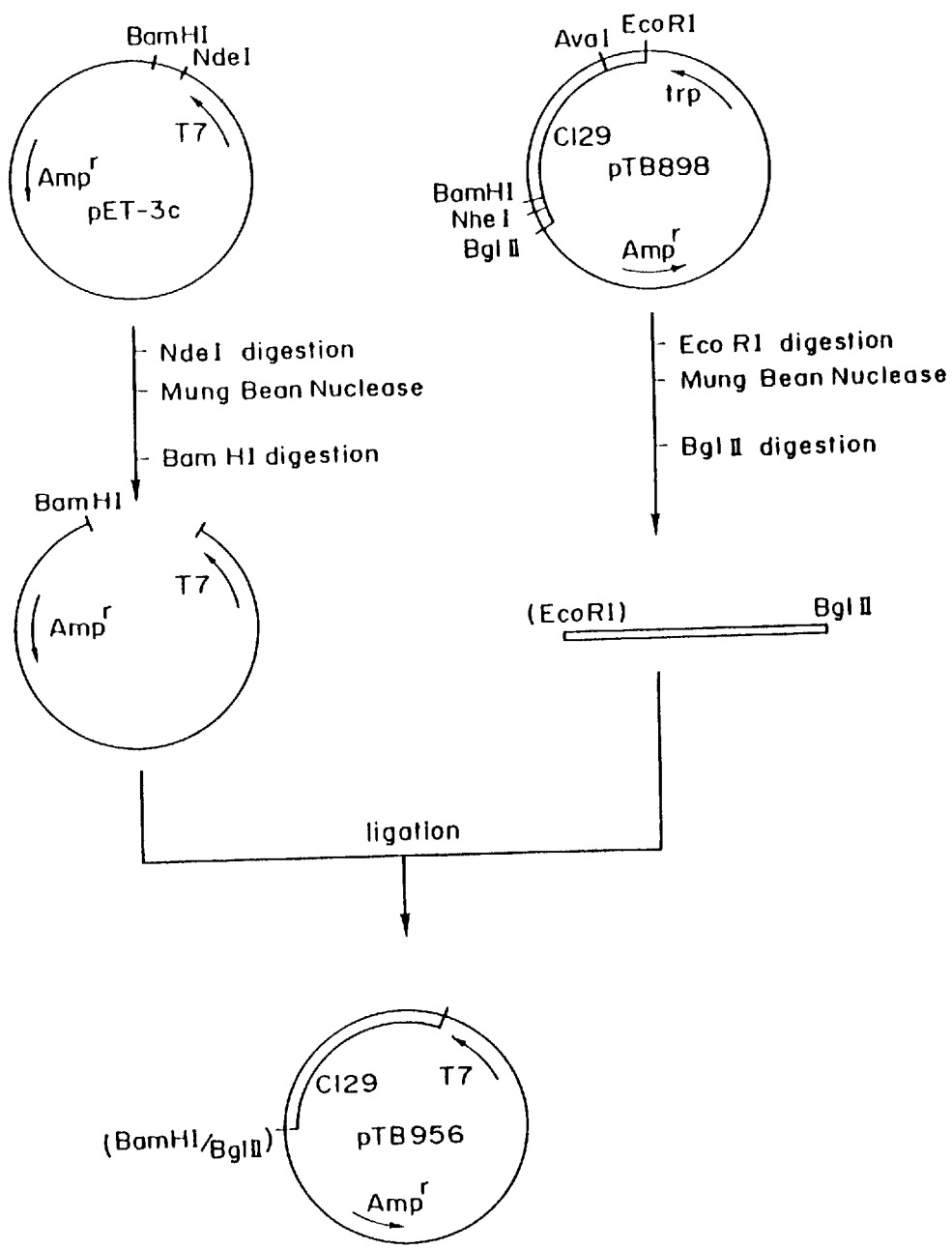
FIG. 73 shows the construction scheme of plasmid pTB956 obtained in Example 47, which encodes rhbFGF mutein C129.

Separately, the DNA of the expression vector pET-3c [described in Alan H. Rosenberg et al., Gene, 56 (1987), pp.125–135], which carried T7 promoter, was digested with the restriction enzyme NdeI; the single-stranded portion was digested by mung bean nuclease treatment to make both ends blunt, after which it was further digested with BamHI. The above-mentioned fragment was inserted into this portion in the presence of T4 DNA ligase to construct the C129 expression plasmid pTB956 (FIG. 73).

This plasmid was used to transform Escherichia coli BL21 (DE3) pLysS [F. William Studler and Barbara A. Moffatt, Journal of Molecular Biology, 189 (1986), pp. 113–130] to give the transformant E. coli BL21 (DE3) pLysS/pTB956 (IFO 14805, FERM BP-2202), which carried the plasmid pTB956 containing the gene which codes for human bFGF mutein C129.

(2) Preparation of Bacterial Cell Extract

The above-mentioned transformant was cultivated in an LB medium containing 10 μg/ml chloramphenicol and 35 μg/ml ampicillin. When Klett value became 180, isopropyl-β-D-thiogalactoside (IPTG) was added to 0.5 mM; cultivation was continued for 3 more hours. After cultivation, cells were harvested and suspended in a 10% sucrose solution containing 20 mM Tris HCl, pH 7.6, which was 1/20th volume of the cultured broth. To this suspension were added phenylmethylsulfonyl fluoride (PMSF) to 1 mM, EDTA to 10 mM, NaCl to 0.1M, spermidine hydrochloride to 10 mM, and lysozyme to 100 μg/ml (every figure shows the final concentration); this mixture was left at 0° C. for 45 minutes, after which it was ultrasonicated for 30 seconds. This solution was then centrifuged at 18,000 rpm (Sorval centrifuge, SS-34 rotor) for 30 minutes to give a supernatant, which was used as a bacterial cell extract.

(3) The bacterial cell extract obtained in (2) above was subjected to enzyme immunoassay (EIA) (sandwich technique) using monoclonal antibodies in the steps (a) through (j) of Example 35. The bacterial cell extract was found to contain FGF. The rhbFGF mutein C129, which lacks the Lys130 and succeeding amino acids, was thus obtained.

EXAMPLE 48

(Production of Human bFGF Mutein CS23C129 using a T7 promoter)

(1) The DNA of the plasmid pTB762 obtained in Example 7, which expresses rhbFGF mutein CS23, was digested with the restriction enzymes AvaI and BamHI to give a region domain containing the Ser70 and Ser88 of CS23.

The DNA of the plasmid pTB956 obtained in Example 47 above was digested with the restriction enzymes AvaI and SalI to yield a fragment containing a T7 promoter. Separately, the DNA of pTB956 was digested with the restriction enzymes SalI and BamHI to give a fragment containing the ampicillin resistance gene.

Figure 74:
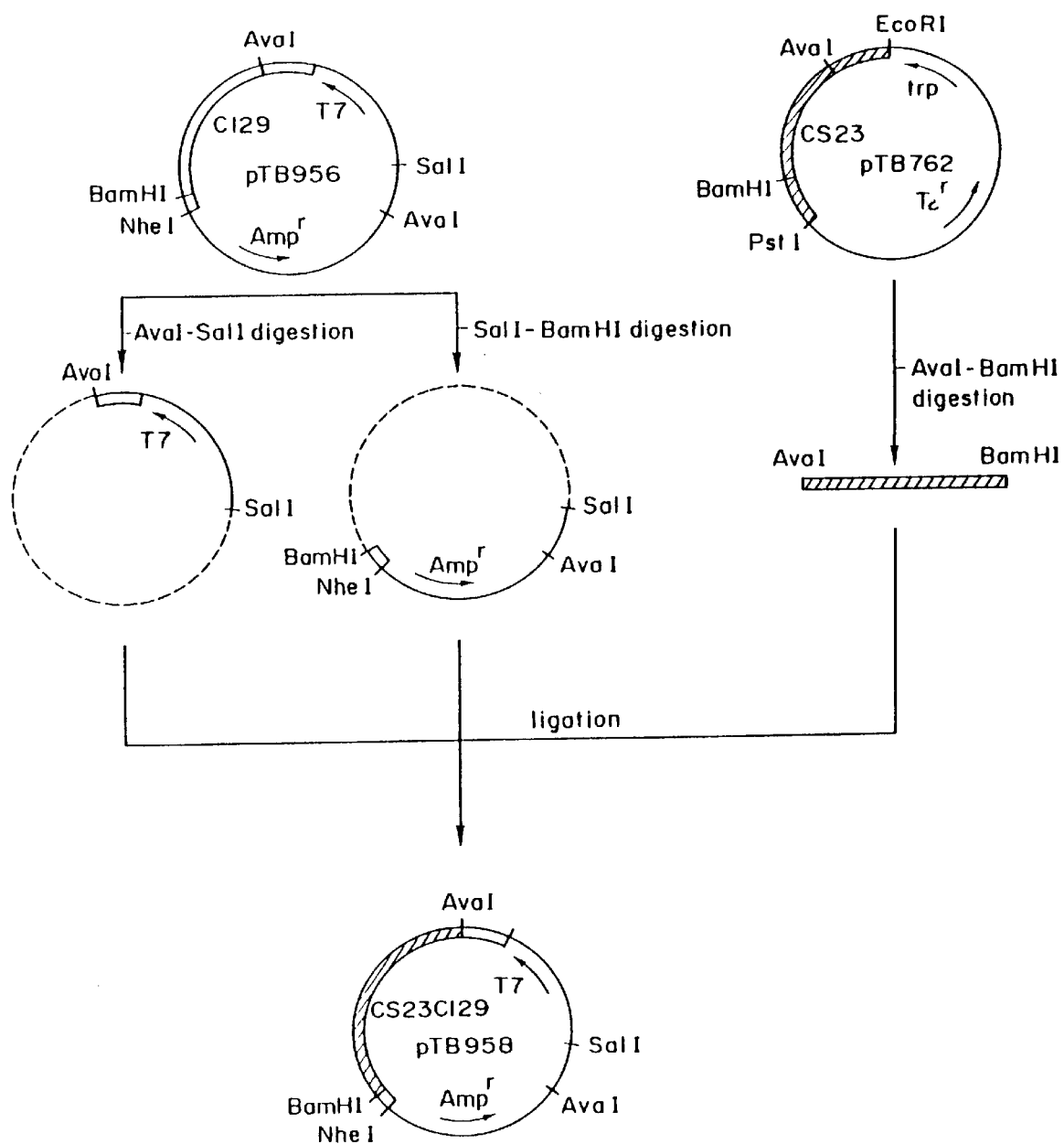
FIG. 74 shows the construction scheme of plasmid pTB958 obtained in Example 48, which encodes rhbFGF mutein CS23C129.

The three DNA fragments thus obtained were ligated together by T4 DNA ligase to construct the rhbFGF mutein CS23C129 expression plasmid pTB958 (FIG. 74).

This plasmid was used to transform Escherichia coli BL21 (DE3) pLysS [F. William Studler and Barbara A. Moffatt, Journal of Molecular Biology, 189 (1986), pp. 113–130] to give the transformant E. coli BL21 (DE3) pLysS/pTB958 (IFO 14806, FERM BP-2203), which carries the plasmid pTB958 containing the gene which codes for bFGF mutein CS23C129.

(2) Preparation of Bacterial Cell Extract

The above-mentioned transformant was cultivated in an LB medium containing 10 μg/ml chloramphenicol and 35 μg/ml ampicillin. When Klett value became 180, isopropyl-β-D-thiogalactoside (IPTG) was added to 0.5 mM; cultivation was continued for 3 more hours. After cultivation, cells were harvested and suspended in a 10% sucrose solution containing 20 mM Tris HCl, pH 7.6, which was 1/20th volume of the cultured broth. To this suspension were added phenylmethylsulfonyl fluoride (PMSF) to 1 mM, EDTA to 10 mM, NaCl to 0.1M, spermidine hydrochloride to 10 mM, and lysozyme to 100 μg/ml (every figure shows the final concentration); this mixture was left at 0° C. for 45 minutes, after which it was ultrasonicated for 30 seconds. This solution was then centrifuged at 18,000 rpm (Sorval centrifuge, SS-34 rotor) for 30 minutes to give a supernatant, which was used as a bacterial cell extract.

(3) The bacterial cell extract obtained in (2) above was subjected to enzyme immunoassay (EIA) (sandwich technique) using monoclonal antibodies in the steps (a) through (j) of Example 35. The bacterial cell extract was found to contain FGF. The rhbFGF mutein C23C129, which lacks the Lys130 and succeeding amino acids, was thus obtained.

The following references, which are referred to for their disclosures at various points in this application, are incorporated herein by reference.

Nature, 249, 123(1974)
National Cancer Institute Monograph, 48, 109(1978)
Proceedings of the National Academy of Sciences of the United States of America (Proc. Natl. Acad. Sci. USA), 82, 6507(1985)
Science, 233, 545(1986)
Biochemical and Biophysical Research Communications (B.B.R.C.), 135, 541(1986)
European Molecular Biology Organization (EMBO) Journal, 5, 2523(1986)
PCT International Publication No. WO/87/01728
FEBS Letters, 213, 189(1987)
Molecular and Cellular Biology, 8, 588 (1988)
Nature, 331, 173 (1988)
Genetic Engineering, Lather, R. F. and Lecog, J. P., Academic Press, pp.31 to 50(1983)
Genetic Engineering: Principles and Methods, Smith, M. and Gillam, S., Plenum Press, 3, pp.1–32(1981)
Gene, 33, 103–119(1985)
Methods in Enzymology, 101, 20–78(1983)
Molecular and General Genetics, 177, 231(1980)
Genetic Engineering, Plenum Press, 3, pp.1–32(1981)
Gene, 2, 95(1977)
Gene, 4, 121(1978)
Gene, 19, 259(1982)
B.B.R.C., 112, 678(1983)
Molecular Cloning, T. Maniatis et al., Cold Spring Harbor Laboratory, p.239(1982)
Proc. Natl. Acad. Sci. USA, 60, 160(1968)
Nucleic Acids Research, 9, 309(1981)
Journal of Molecular Biology, 120, 517(1978)
Journal of Molecular Biology, 41, 459(1969)
Genetics, 39, 440(1954)
Proc. Natl. Acad. Sci. USA, 73, 4174(1976)
Gene, 24, 255(1983)
Journal of Biochemistry, 95, 87(1984)
Proc. Natl. Acad. Sci. USA, 69, 2110(1972)
Gene, 17, 107(1982)
Molecular and General Genetics, 168, 111(1979)
Proc. Natl. Acad. Sci. USA, 75, 1929(1978)
Virology, 52, 456(1973)
Journal of Experiments in Molecular Genetics, 431–433, Cold Spring Harbor Laboratory, New York (1972)
Proc. Natl. Acad. Sci. USA, 77, 4505(1980)
Science, 122, 501(1952)
Virology, 8, 396(1959)
Journal of the American Medical Association, 199, 519 (1967)
Proceedings of the Society for the Biological Medicine, 73, 1(1950)
Molecular and Cellular Biology, 3, 280(1983)
Nucleic Acids Research, 1, 1513(1979)
Proc. Natl. Acad. Sci. USA, 72, 3961(1975)
Molecular Cloning, Cold Spring Harbor Laboratory, p.309 (1982)
Nucleic Acids Research, 11, 3077–3085(1983)
Developmental Biology, 41, 391(1974)
Nature, 256, 495(1975)
Journal of Biological Chemistry, 256, 9750(1981)
Japanese Patent Laid-open No.62-175182
European Patent Publication No.225,701
Japanese Patent Laid-open No.61-63282
European Patent Publication No. 172,619
Gene 56, 125–135 (1987)
Journal of Molecular Biology, 189, 113–130 (1986)

What we claim is:

1. A mutein of basic fibroblast growth factor (bFGF) wherein at least one constituent cysteine of bFGF is replaced by another amino acid so that the mutein has greater stability under acidic conditions than the bFGF in at least one of the following properties:

fibroblast growth promoting activity, growth stimulating activity of capillary endothelial cells or angiogenic activity.

2. A mutein as claimed in claim 1, wherein the bFGF includes the amino acid sequence:

Phe-Phe-Leu-Arg-Ile-His-Pro-Asp-Gly-Arg-Val-Asp-Gly-Val-Arg-Glu-Lys-Ser-Asp-Pro.

3. A mutein as claimed in claim 1, wherein at least one constituent cysteine is replaced by a neutral amino acid.

4. A mutein as claimed in claim 3, wherein the neutral amino acid is selected from the group consisting of glycine, valine, alanine, leucine, isoleucine, tyrosine, phenylalanine, histidine, tryptophan, serine, threonine and methionine.

5. A mutein as claimed in claim 3, wherein the neutral amino acid is serine or threonine.

6. A mutein as claimed in claim 3, wherein the neutral amino acid is serine.

7. A mutein as claimed in claim 1, wherein the bFGF has the formula:

Pro—Ala—Leu—Pro—Glu—Asp—Gly—Gly—Ser—Gly—Ala—Phe—Pro—Pro—Gly—His—Phe—Lys—Asp—Pro—Lys—Arg—Leu—Tyr—Cys—Lys—Asn—Gly—Gly—Phe—Phe—Leu—Arg—Ile—His—Pro—Asp—Gly—Arg—Val—Asp—Gly—Val—Arg—Glu—Lys—Ser—Asp—Pro—His—Ile—Lys—Leu—Gln—Leu—Gln—Ala—Glu—Glu—Arg—Gly—Val—Val—Ser—Ile—Lys—Gly—Val—Cys—Ala—Asn—Arg—Tyr—Leu—Ala—Met—Lys—Glu—Asp—Gly—Arg—Leu—Leu—Ala—Ser—Lys—Cys—Val—Thr—Asp—Glu—Cys—Phe—Phe—Phe—Glu—Arg—Leu—Glu—Ser—Asn—Asn—Tyr—Asn—Thr—Tyr—Arg—Ser—Arg—Lys—Tyr—X—Ser—Trp—Tyr—Val—Ala—Leu—Lys—Arg—Thr—Gly—Gln—Tyr—Lys—Leu—Gly—Y—Lys—Thr—Gly—Pro—Gly—Gln—Lys—Ala—Ile—Leu—Phe—Leu—Pro—Met—Ser—Ala—Lys—Ser, in which X represents Thr or Ser, when X is Thr, Y represents Ser, and when X is Ser, Y represents Pro.

8. A mutein as claimed in claim 1, wherein the mutein is a mutein of human bFGF.

9. A mutein as claimed in claim 1, wherein the mutein is a mutein of bovine or murine bFGF.

10. The mutein of claim 1, which has at least a 20% greater relative activity than bFGF at acidic conditions of pH 4 at 37° C. for 10 minutes with a protein concentration of 1 microgram/ml.

11. The mutein of claim 1, wherein the second and third constituent cysteines of the FGF are each replaced by another amino acid.

12. The mutein of claim 11, where the amino acids are neutral amino acids.

13. The mutein of claim 11, wherein the FGF is human basic FGF.

* * * * *